(12) United States Patent
Kwak et al.

(10) Patent No.: US 8,338,000 B2
(45) Date of Patent: Dec. 25, 2012

(54) ORGANIC LIGHT EMITTING DEVICE

(75) Inventors: Yoon-Hyun Kwak, Yongin (KR); Seok-Hwan Hwang, Yongin (KR); Young-Kook Kim, Yongin (KR); Hye-Jin Jung, Yongin (KR); Jong-Hyuk Lee, Yongin (KR); Jin-O Lim, Yongin (KR); Hyung-Jun Song, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 307 days.

(21) Appl. No.: 12/852,398

(22) Filed: Aug. 6, 2010

(65) Prior Publication Data

US 2011/0031483 A1 Feb. 10, 2011

(30) Foreign Application Priority Data

Aug. 10, 2009 (KR) .................. 10-2009-0073520

(51) Int. Cl.
*H01L 51/54* (2006.01)
*C09K 11/06* (2006.01)
*C07D 209/58* (2006.01)

(52) U.S. Cl. .......... 428/690; 428/917; 313/502; 257/40; 548/420

(58) Field of Classification Search .................. None
See application file for complete search history.

(56) References Cited

U.S. PATENT DOCUMENTS

| 6,835,468 | B2 | 12/2004 | Cho et al. |
| 2004/0170861 | A1 | 9/2004 | Culligan et al. |
| 2006/0154105 | A1 | 7/2006 | Yamamoto et al. |

FOREIGN PATENT DOCUMENTS

| EP | 2 138 551 A2 | 12/2009 |
| JP | 2004-217547 | 8/2004 |
| JP | 2005093159 A | 4/2005 |
| JP | 2008133225 A | 6/2008 |
| KR | 1020060115399 A | 11/2006 |
| KR | 1020080085000 A | 9/2008 |
| KR | 1020080114785 A | 12/2008 |

OTHER PUBLICATIONS

Buu-Hoi, et al. "Carcinogenic Nitrogen Compounds. Part LXXII. The Mohlau-Bischler Reaction as a Preparative Route to 2-Arylindoles" J. Chem. Soc. C, 1971, 2606-2609. Year of publication: 1971.*

Registration Determination Certificate dated Nov. 30, 2011 issued in Korean Priority Application No. 10-2009-0073520, 5 pages.

\* cited by examiner

*Primary Examiner* — Lynda Salvatore
*Assistant Examiner* — Andrew K Bohaty
(74) *Attorney, Agent, or Firm* — Christie, Parker & Hale, LLP

(57) ABSTRACT

Embodiments of the present invention are directed to a heterocyclic compound and an organic light-emitting device including the heterocyclic compound. The organic light-emitting devices using the heterocyclic compounds have high-efficiency, low driving voltage, high luminance and long lifespan.

22 Claims, 1 Drawing Sheet

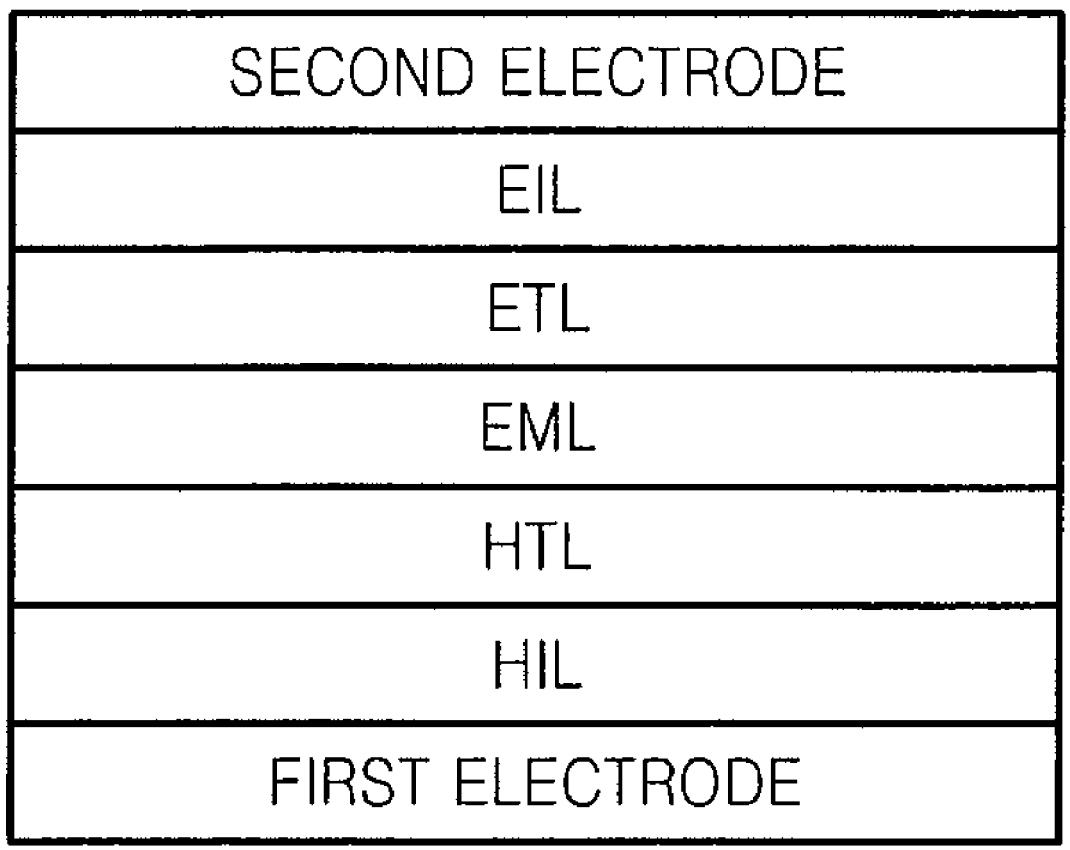

ORGANIC LIGHT EMITTING DEVICE

CROSS-REFERENCE TO RELATED PATENT APPLICATION

This application claims priority to and the benefit of Korean Patent Application No. 10-2009-0073520, filed on Aug. 10, 2009, in the Korean Intellectual Property Office, the entire content of which is incorporated herein by reference.

BACKGROUND OF THE INVENTION

1. Field of the Invention

The present invention relates to a heterocyclic compound and an organic light-emitting device including the heterocyclic compound.

2. Description of the Related Art

Organic light-emitting devices are self-emission type display devices and have wide viewing angles, high contrast ratios, and short response times. Due to these characteristics, organic light-emitting devices are drawing more attention.

Such organic light-emitting devices can be roughly classified into inorganic light-emitting devices which include emission layers containing inorganic compounds, and organic light-emitting devices which include emission layers containing organic compounds. Organic light-emitting devices have higher luminance, lower driving voltages, and shorter response times than inorganic light-emitting devices, and can render multi-colored displays. In addition, organic light-emitting devices produce various colors. Thus, much research into such organic light-emitting devices has been conducted.

Typically, an organic light-emitting device has a stack structure including an anode, a cathode and an organic emission layer between the anode and cathode. However, a hole injection layer and/or a hole transport layer may be further stacked between the anode and the organic emission layer, and/or an electron transport layer may be further stacked between the organic emission layer and the cathode. In other words, an organic light-emitting device may have an anode/hole transport layer/organic emission layer/cathode structure or an anode/hole transport layer/organic emission layer/electron transport layer/cathode structure.

As the material for forming the hole transport layer, polyphenyl compounds or anthracene derivatives can be used. However, organic light-emitting devices including hole injection layers and/or hole transport layers formed of such materials do not have satisfactory life span, efficiency, and power consumption characteristics, thus leaving much room for improvement.

SUMMARY OF THE INVENTION

According to embodiments of the present invention, a heterocyclic compound imparts improved electrical characteristics, charge transporting capabilities and light-emission capabilities.

According to other embodiments of the present invention, an organic light-emitting device includes the heterocyclic compound.

In yet other embodiments of the present invention, a flat panel display device includes the organic light-emitting device.

In still other embodiments of the present invention, an organic light-emitting device comprises at least one layer containing the heterocyclic compound, where the at least one layer is formed using a wet process.

According to embodiments of the present invention, a heterocyclic compound is represented by Formula 1 below:

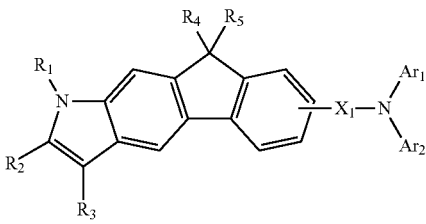

Formula 1

In Formula 1, each of $Ar_1$ and $Ar_2$ is independently selected from substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. $X_1$ is selected from single bonds, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups. Each of $R_1$, $R_2$, and $R_3$ is independently selected from hydrogen, heavy hydrogen, substituted and unsubstituted $C_1$-$C_{50}$ alkyl groups, substituted and unsubstituted $C_1$-$C_{50}$ alkoxy groups, substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. Each of $R_4$ and $R_5$ is independently selected from hydrogen, heavy hydrogen, substituted and unsubstituted $C_1$-$C_{30}$ alkyl groups, substituted and unsubstituted $C_1$-$C_{30}$ alkoxy groups, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups.

The heterocyclic compound may include a compound represented by Formulae 2 through 6:

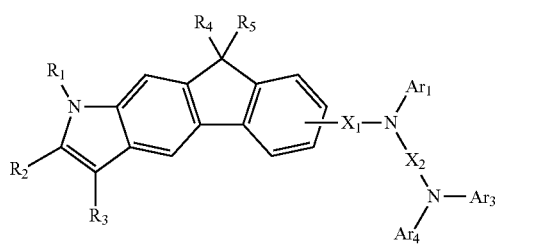

Formula 2

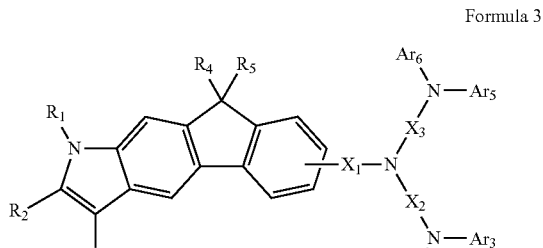

Formula 3

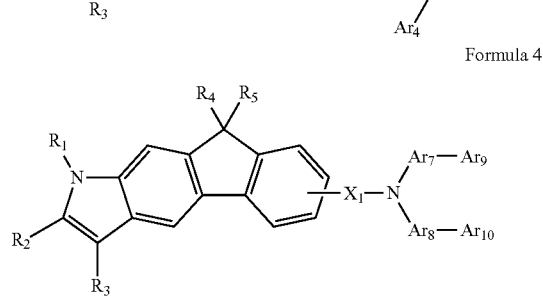

Formula 4

-continued

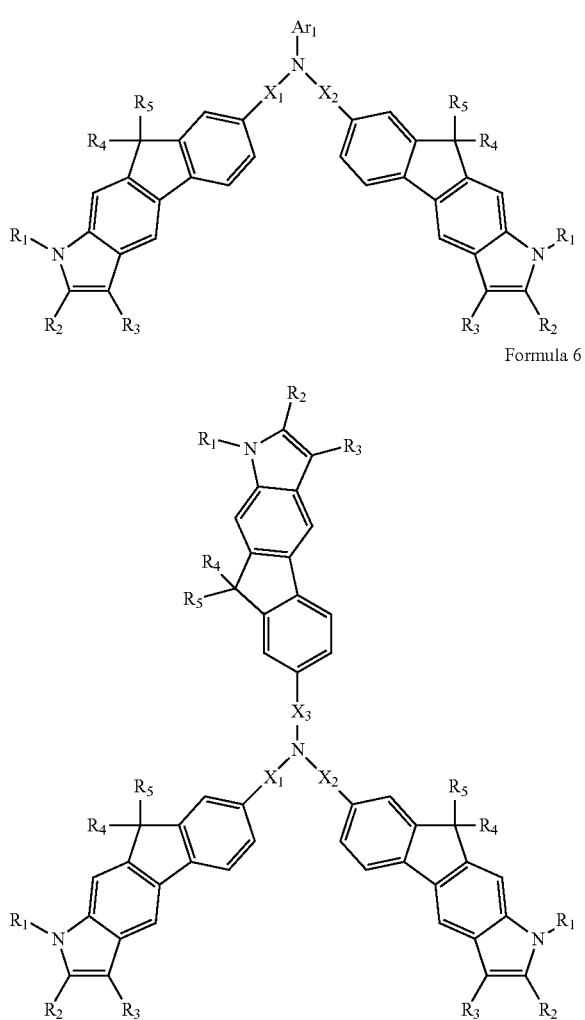

Formula 5

Formula 6

In Formulae 2 through 6, each of $Ar_1$ through $Ar_{10}$ is independently selected from substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. Each of $X_1$ through $X_3$ is independently selected from single bonds, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups. Each of $R_1$, $R_2$, and $R_3$ is independently selected from hydrogen, heavy hydrogen, substituted and unsubstituted $C_1$-$C_{50}$ alkyl groups, substituted and unsubstituted $C_1$-$C_{50}$ alkoxy groups, substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. Each of $R_4$ and $R_5$ is independently selected from hydrogen, heavy hydrogen, substituted and unsubstituted $C_1$-$C_{30}$ alkyl groups, substituted and unsubstituted $C_1$-$C_{30}$ alkoxy groups, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups.

In some embodiments, in Formulae 1 through 6, $Ar_1$, $Ar_2$, $Ar_3$, $Ar_4$, $Ar_5$, $Ar_6$, $Ar_7$, $Ar_8$, $Ar_9$ and $Ar_{10}$ may be identical to each other; $X_1$, $X_2$, and $X_3$ may be identical to each other; $R_2$ and $R_3$ may be identical to each other; or $R_4$ and $R_5$ may be identical to each other.

In some embodiments, $R_1$ through $R_3$ or $X_1$ through $X_3$ may each be independently selected from phenyl groups, naphthyl groups, biphenyl groups, fluorene groups, and phenanthrene groups.

In some embodiments, $R_4$ and $R_5$ may each be a methyl group.

In some embodiments, in Formula 1 above, each of $Ar_3$ through $Ar_{10}$ may be independently selected from unsubstituted monocyclic to tricyclic aryl groups, unsubstituted $C_4$-$C_{30}$ heteroaryl groups, substituted monocyclic to tricyclic aryl groups, and substituted $C_4$-$C_{30}$ heteroaryl groups. Nonlimiting examples of suitable unsubstituted monocyclic to tricyclic aryl groups include phenyl groups, naphthyl groups, biphenyl groups, terphenyl groups, anthracenyl groups, fluorenyl groups and carbazolyl groups. Nonlimiting examples of suitable substituted monocyclic to tricyclic aryl groups include phenyl groups, naphthyl groups, biphenyl groups, terphenyl groups, anthracenyl groups, fluorenyl groups, and carbazolyl groups having at least one substituent selected from $C_1$-$C_5$ alkyl groups, $C_1$-$C_5$ alkoxy groups, cyano groups, amine groups, phenoxy groups, phenyl groups, naphthyl groups and halogen groups. Nonlimiting examples of suitable substituted $C_4$-$C_{30}$ heteroaryl groups include groups with at least one substituent selected from $C_1$-$C_5$ alkyl groups, $C_1$-$C_4$ alkoxy groups, cyano groups, amine groups, phenoxy groups, phenyl groups, naphthyl groups and halogen groups.

The heterocyclic compound of Formula 1 may include one of Compounds 2, 14, 23, 32, 42 and 76 below:

2

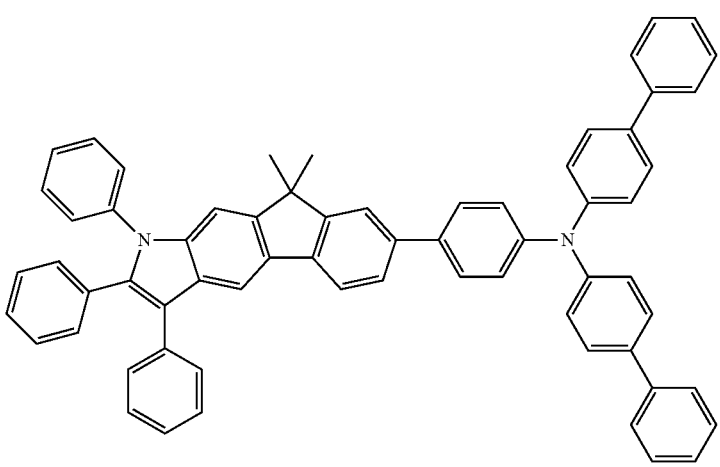

-continued
14
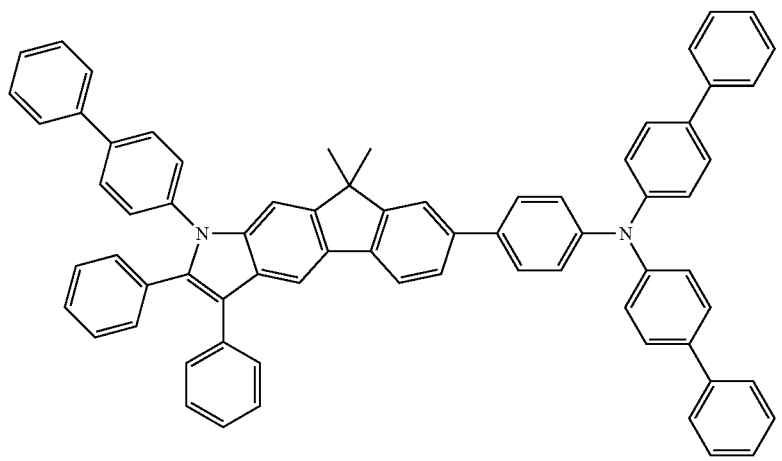
23
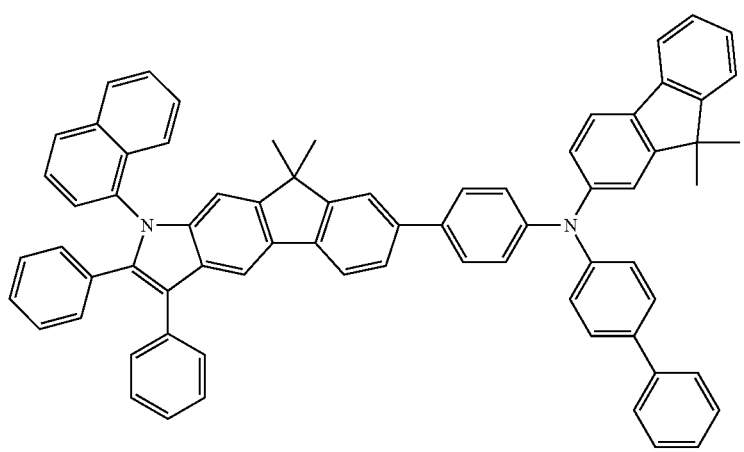
32
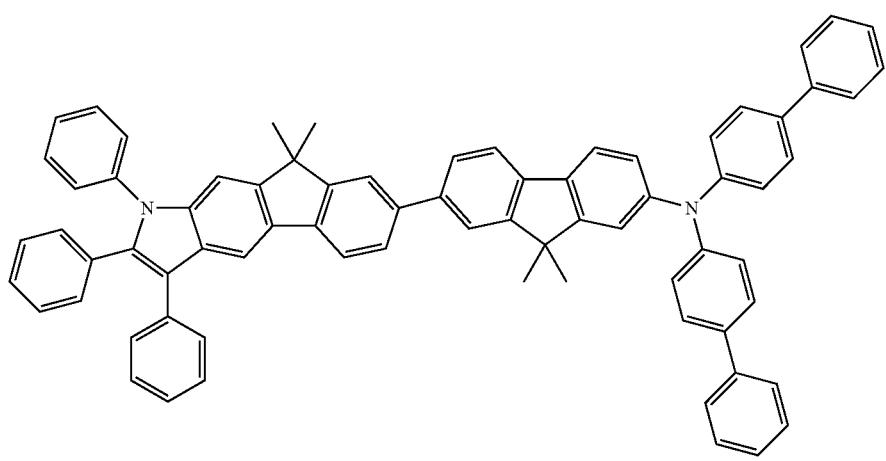

-continued

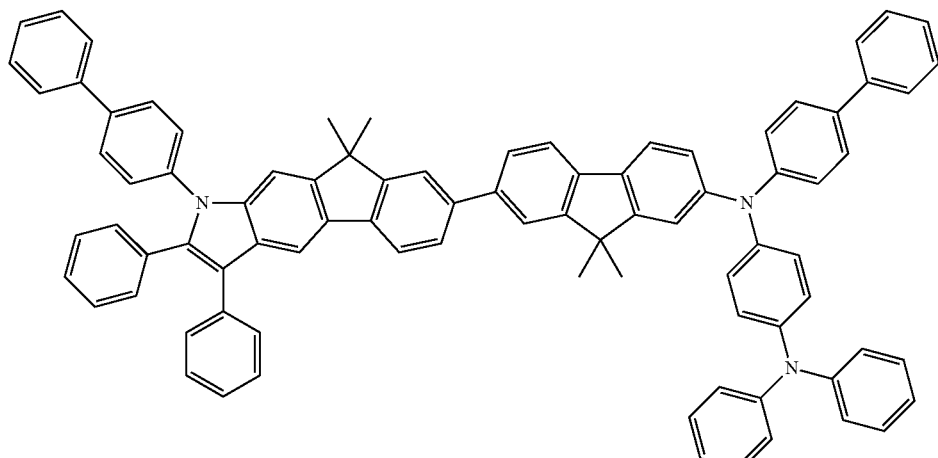
42

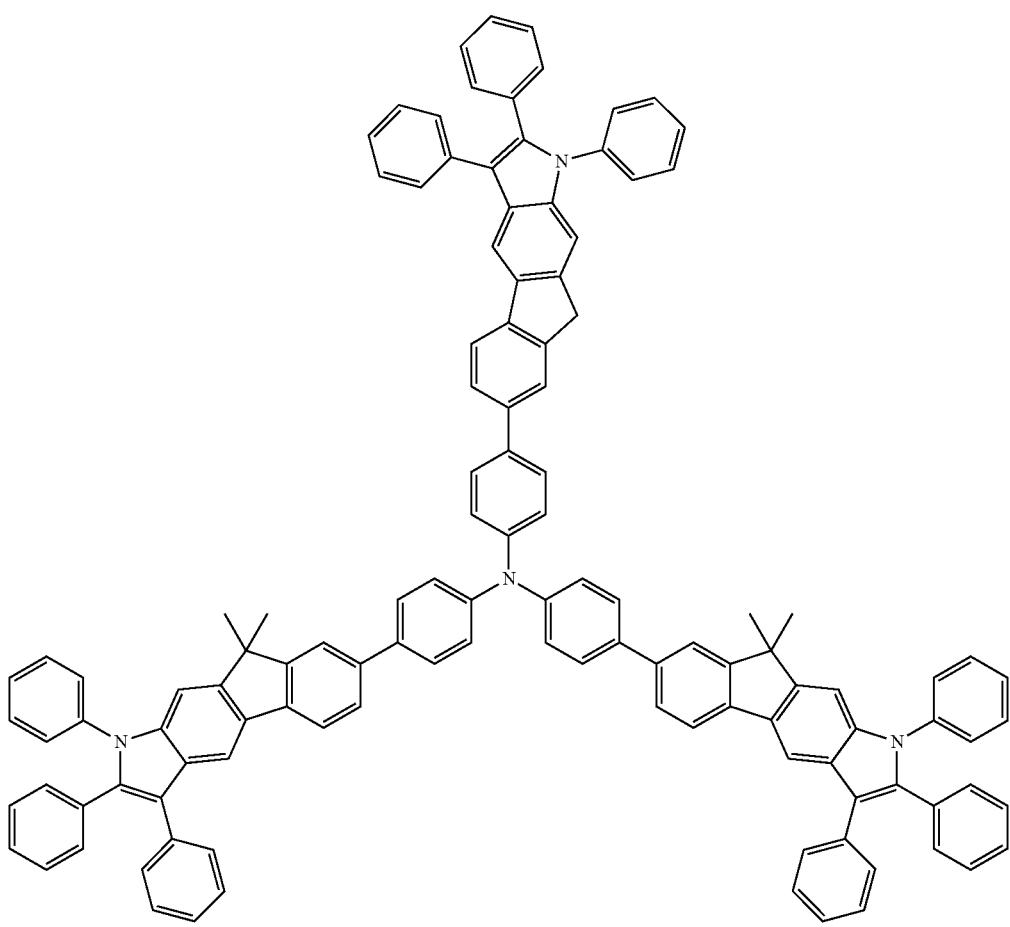
76

According to other embodiments of the present invention, an organic light-emitting device comprises a first electrode, a second electrode, and an organic layer between the first electrode and the second electrode, wherein the organic layer comprises the heterocyclic compound.

The organic layer may include a hole injection layer or a hole transport layer.

The organic layer may include a single film having both a hole injection function and a hole transport function.

The organic layer may include an emission layer.

The organic layer may include an emission layer, and the heterocylic compound may be used as a fluorescent or phosphorescent host.

The organic layer may comprise an emission layer, and the heterocylic compound may be used as a fluorescent dopant.

The organic layer may include an emission layer, a hole injection layer or a hole transport layer, and the emission layer may include an anthracene compound.

The organic layer may include an emission layer, a hole injection layer or a hole transport layer, and the emission layer may include an arylamine compound.

The organic layer may include an emission layer, a hole injection layer or a hole transport layer, and the emission layer may include a styryl compound.

The organic layer may include an emission layer, a hole injection layer or a hole transport layer, and the emission layer may include a red emission layer, a green emission layer, a blue emission layer or a white emission layer that comprises a phosphorescent compound.

The organic layer may include at least one layer selected from hole injection layers, hole transport layers, electron blocking layers, emission layers, hole blocking layers, electron transport layers, and electron injection layers.

The organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

According to other embodiments of the present invention, a flat panel display device comprises the organic light-emitting device described above, wherein the first electrode of the organic light-emitting device is electrically connected to a source electrode or a drain electrode of a thin-film transistor.

According to another aspect of the present invention, there is provided an organic light-emitting device comprising: a first electrode; a second electrode; and an organic layer interposed between the first electrode and the second electrode, wherein the organic layer comprises at least one layer comprising the heterocyclic compound of Formula 1, the at least one layer formed using a wet process.

BRIEF DESCRIPTION OF THE DRAWING

The above and other features and advantages of the present invention will become more apparent by reference to the following detailed description when considered in conjunction with the attached drawings in which:

FIG. 1 is a diagram of the structure of an organic light-emitting device according to an embodiment of the present invention.

DETAILED DESCRIPTION OF THE INVENTION

The present invention will now be described with reference to the accompanying drawings, in which exemplary embodiments of the invention are shown.

A heterocyclic compound according to an embodiment of the present invention is represented by Formula 1 below:

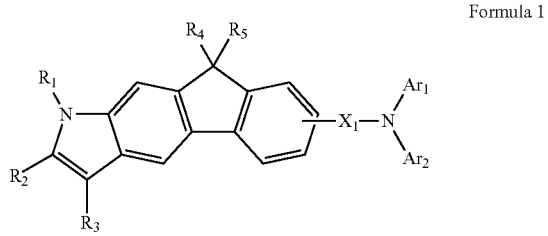

Formula 1

In Formula 1, each of $Ar_1$ and $Ar_2$ is independently selected from substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. $X_1$ is selected from single bonds, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups. Each of $R_1$, $R_2$, and $R_3$ is independently selected from hydrogen, heavy hydrogen, substituted and unsubstituted $C_1$-$C_{50}$ alkyl groups, substituted and unsubstituted $C_1$-$C_{50}$ alkoxy groups, substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. Each of $R_4$ and $R_5$ is independently selected from hydrogen, heavy hydrogen, substituted and unsubstituted $C_1$-$C_{30}$ alkyl groups, substituted and unsubstituted $C_1$-$C_{30}$ alkoxy groups, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups.

Anthracene derivatives have been used as materials for the organic emission layer. For example, organic light-emitting devices have been manufactured using phenylanthracene dimer or trimer compounds. However, such organic light-emitting devices have narrow energy gaps and lower blue-light color purity since two or three oligomeric species of anthracene are linked by conjugation. In addition, such compounds are highly vulnerable to oxidation and thus are liable to produce impurities, necessitating purification.

In an effort overcome these drawbacks, organic light-emitting devices manufactured using anthracene compounds such as naphthalene substituted for anthracene at the 1,9 positions or diphenylanthracene compounds including an aryl group substituted for a phenyl group at the m-position have been introduced. However, these organic light-emitting devices have lower light-emission efficiency.

In addition, organic light-emitting devices have been manufactured using naphthalene-substituted monoanthracene derivatives. However, the light-emission efficiency of such devices is low at about 1 cd/A, and thus such organic light-emitting devices are not suitable for practical use.

Furthermore, organic light-emitting devices have been manufactured using phenylanthracene compounds including an aryl substituent at the m-position. Such compounds have good thermal resistance but lead to low light-emission efficiency of about 2 cd/A. Thus, further improvement is required.

The heterocyclic compounds of Formula 1 according to embodiments of the present invention may be suitable as a material for an emission layer and/or a charge transport layer or charge injection layer of an organic light-emitting device. The heterocyclic compounds of Formula 1 have high glass transition temperatures (Tg) or melting points due to the introduction of the heterocyclic group. Thus, the heterocyclic compound has thermal resistance against Joule's heat generated in an organic layer, between organic layers, or between an organic layer and a metallic electrode when light emission occurs, and has high durability in high-temperature environments.

An organic light-emitting device manufactured using the heterocyclic compound of Formula 1 (which includes an amine ring fused to a fluorene group) has good durability when stored or operated. In addition, due to the introduction of a substituent such as a fluorene group or a naphthyl group, molecular layers formed as thin films may be maintained in good condition, thereby improving the characteristics of the organic light-emitting device.

In some embodiments, the heterocyclic compound represented by Formula 1 may be selected from compounds represented by Formulae 2 through 6 below.

Formula 2
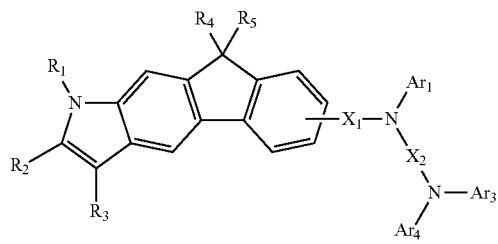

Formula 3
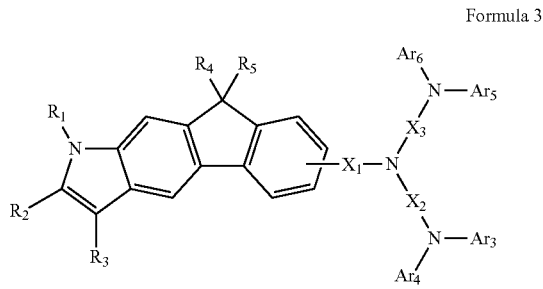

Formula 4
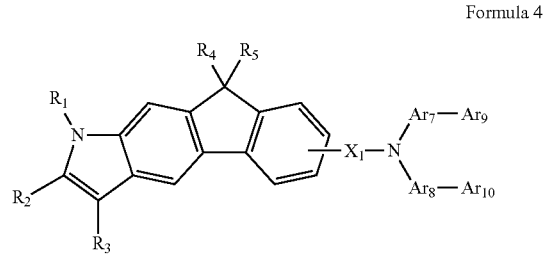

Formula 5
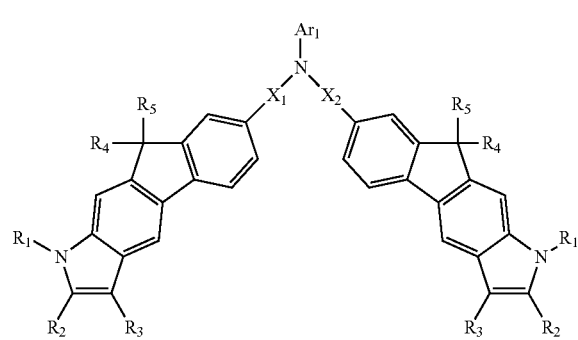

Formula 6
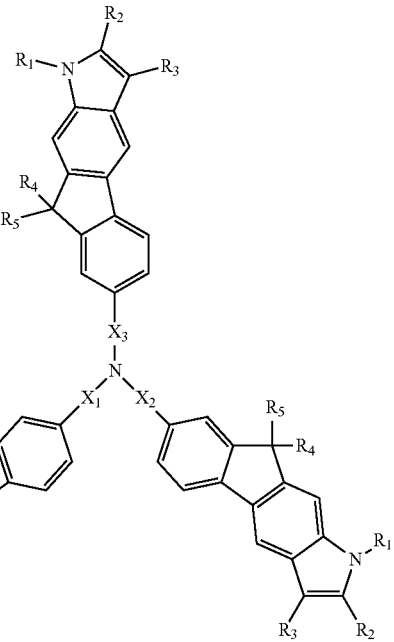

In Formulae 2 through 6, each of $Ar_1$ through $Ar_{10}$ is independently selected from substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups. Each of $X_1$ through $X_3$ is independently selected from substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups. Each of $R_1$ through $R_5$ is as defined in Formula 1 above.

Substituents in the heterocyclic compound of Formula 1 will now be described. In some embodiments, in the heterocyclic compounds of Formulae 1 through 6, each of $Ar_1$, $Ar_2$, $Ar_3$, $Ar_4$, $Ar_5$, $Ar_6$, $Ar_7$, $Ar_8$, $Ar_9$ and $Ar_{10}$ may be identical to each other, each of $X_1$, $X_2$, and $X_3$ may be identical to each other, each of $R_2$ and $R_3$ may be identical to each other, or each of $R_4$ and $R_5$ may be identical to each other.

In some embodiments, on Formulae 1 through 6, each of $R_1$ through $R_3$ or $X_1$ through $X_3$ may be independently selected from, for example, phenyl groups, naphthyl groups, biphenyl groups, fluorene groups, and phenanthrene groups.

In some embodiments, in Formulae 1 through 6, each of $R_4$ and $R_5$ may be, for example, a methyl group, and each of $Ar_3$ through $Ar_{10}$ may be independently selected from, for example, unsubstituted monocyclic to tricyclic aryl groups, unsubstituted $C_4$-$C_{30}$ heteroaryl groups, substituted monocyclic to tricyclic aryl groups, and substituted $C_4$-$C_{30}$ heteroaryl groups. Nonlimiting examples of suitable unsubstituted monocyclic to tricyclic aryl groups include phenyl groups, naphthyl groups, biphenyl groups, terphenyl groups, anthracenyl groups, fluorenyl groups, and carbazolyl groups. Nonlimiting examples of suitable substituted monocyclic to tricyclic aryl groups include phenyl groups, naphthyl groups, biphenyl groups, terphenyl groups, anthracenyl groups, fluorenyl groups, and carbazolyl groups having at least one substituent selected from $C_1$-$C_5$ alkyl groups, $C_1$-$C_5$ alkoxy groups, cyano groups, amine groups, phenoxy groups, phenyl groups, naphthyl groups and halogen groups. Nonlimiting examples of suitable substituted $C_4$-$C_{30}$ heteroaryl groups include groups with at least one substituent selected from $C_1$-$C_5$ alkyl groups, $C_1$-$C_4$ alkoxy groups, cyano groups, amine groups, phenoxy groups, phenyl groups, naphthyl groups, and halogen groups.

Substituents described with reference to Formulae 1 through 6 will now be described. The unsubstituted $C_1$-$C_{50}$ alkyl group used herein may be linear or branched. Nonlimiting examples of suitable alkyl groups include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. In some embodiments, at least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_6$-$C_{60}$ aryl group used herein refers to a $C_6$-$C_{30}$ carbocyclic aromatic system containing at least one ring. In some embodiments, at least two rings may be fused to each other or linked to each other by a single bond. The term 'aryl' refers to an aromatic system, such as phenyl, naphthyl, or anthracenyl systems. In some embodiments, at least one hydrogen atom in the aryl group may be substituted with a substituent such as those described with reference to the unsubstituted $C_1$-$C_{50}$ alkyl group.

Nonlimiting examples of the substituted or unsubstituted $C_6$-$C_{30}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-toryl groups, o-, m-, and p-cumenyl groups, mesityl groups, phenoxyphenyl groups, ($\alpha,\alpha$-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group used herein includes one, two or three hetero atoms selected from N, O, P and S. In some embodiments, at least two rings may be fused to each other or linked to each other by a single bond. Nonlimiting examples of the unsubstituted $C_4$-$C_{60}$ heteroaryl group may include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. In some embodiments, at least one hydrogen atom in the heteroaryl group may be substituted with a substituent such as those described with reference to the unsubstituted $C_1$-$C_{50}$ alkyl group.

The unsubstituted $C_6$-$C_{60}$ condensed polycyclic group used herein refers to a substituent including at least two rings wherein at least one aromatic ring and/or at least one non-aromatic ring are fused to each other. The unsubstituted $C_6$-$C_{60}$ condensed polycyclic group may include some of the substituents described with reference to the aryl group or the heteroaryl group.

One exemplary heterocyclic compound of Formula 1 may be synthesized according to the below reaction scheme.

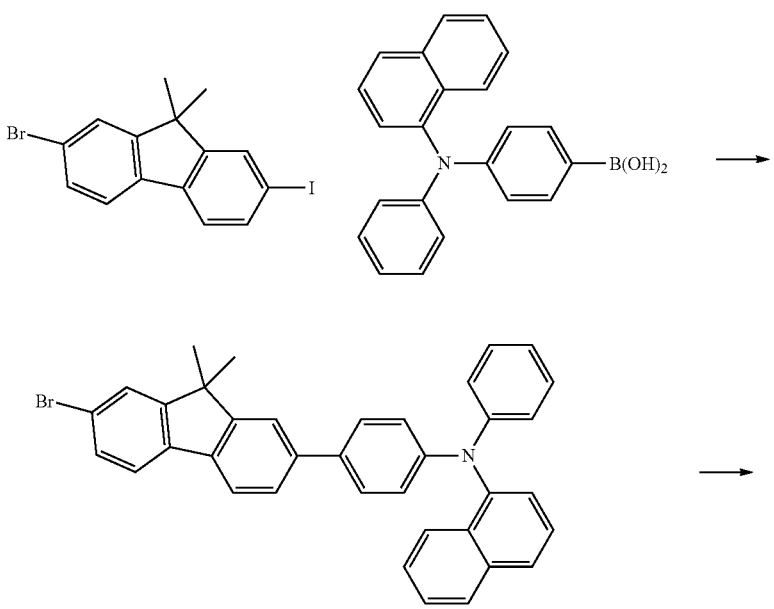

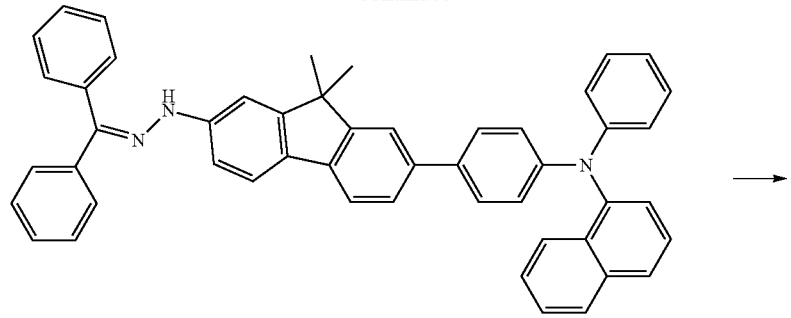
→
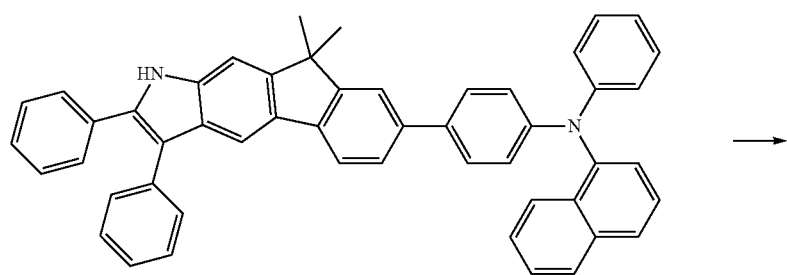
→
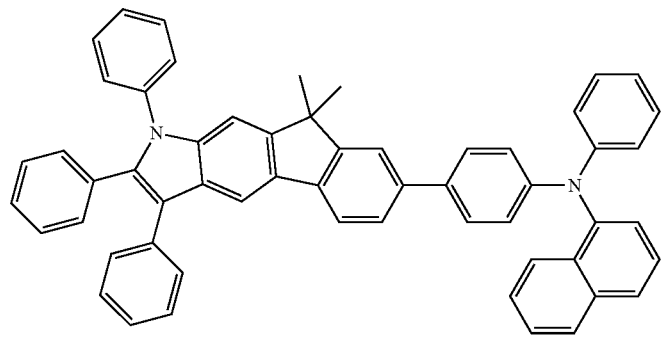
compound 1
Nonlimiting examples of heterocyclic compounds of Formula 1 include Compounds 1 through 76 represented below.
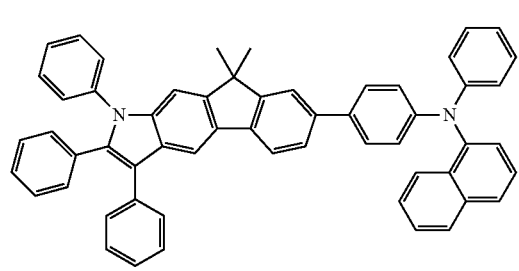
1
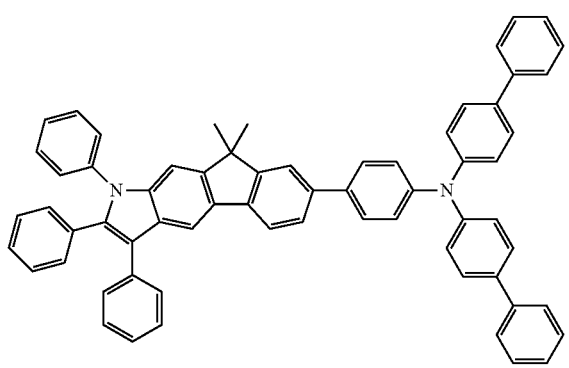
2

-continued
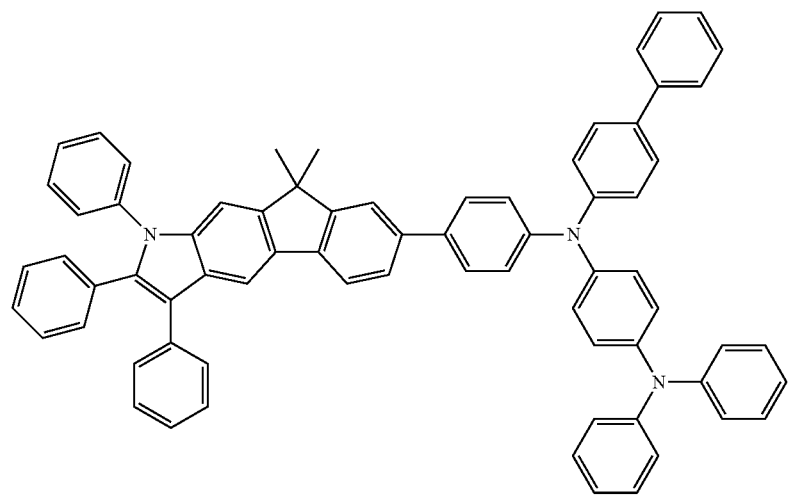
3
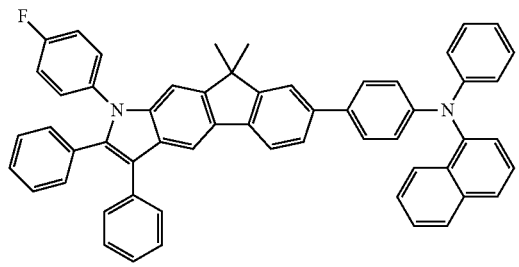
4
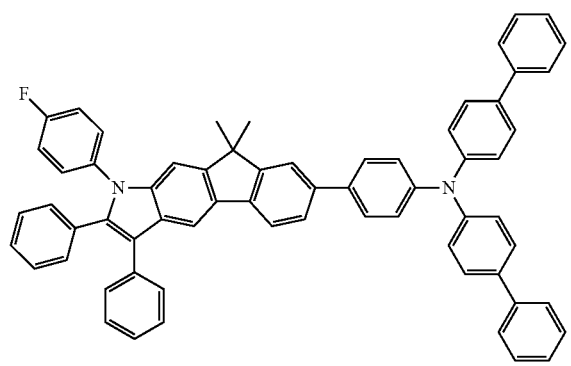
5
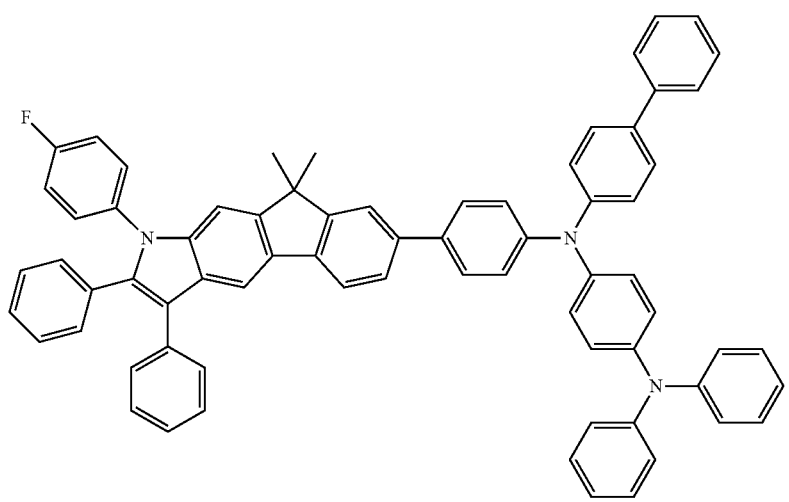
6

-continued
7
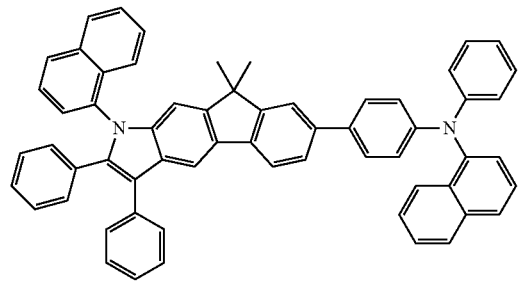
8
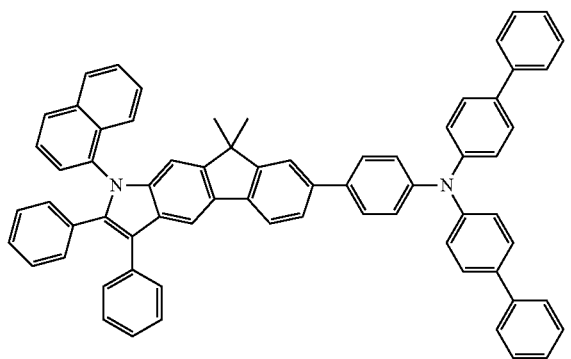
9
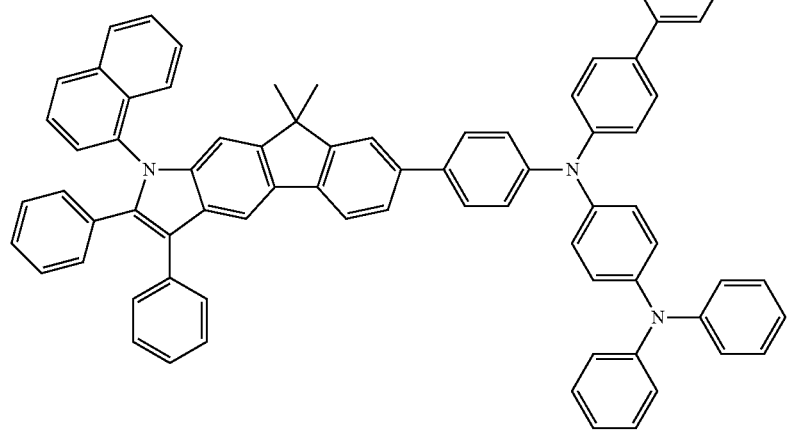
10
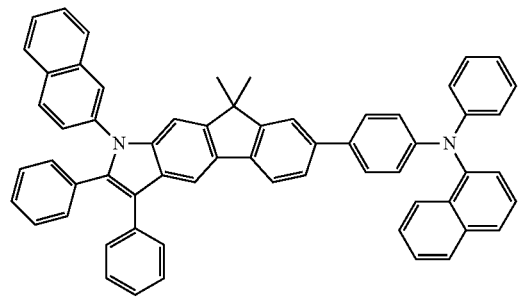
11
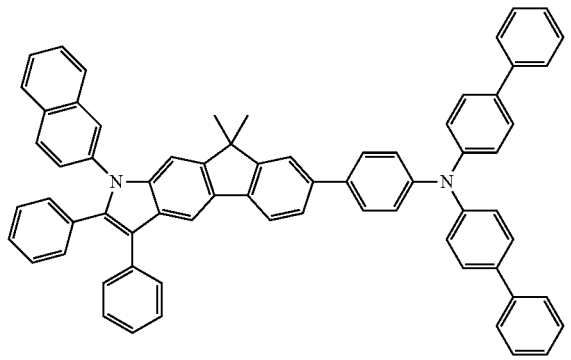

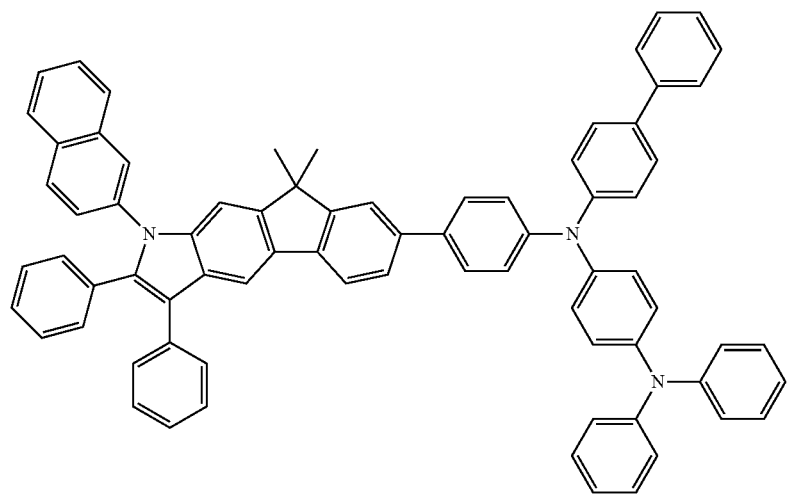
12
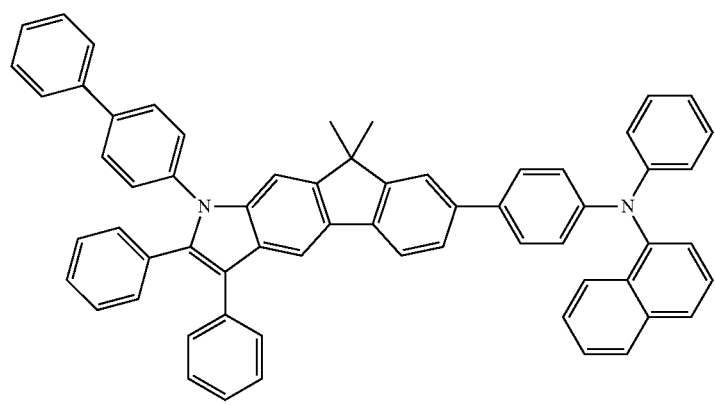
13
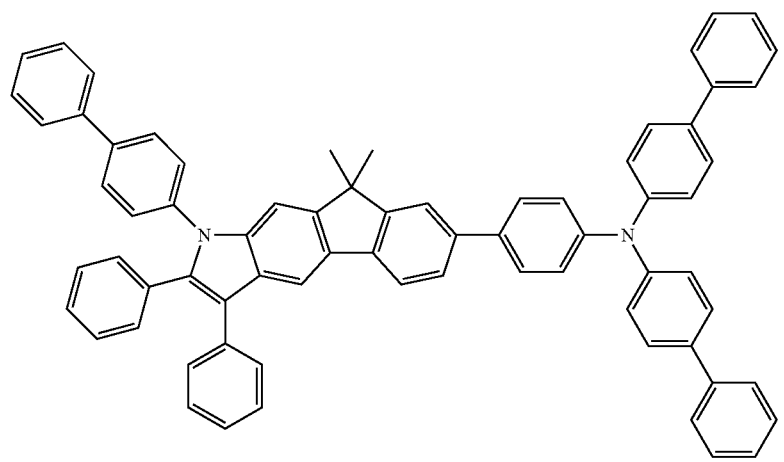
14

-continued
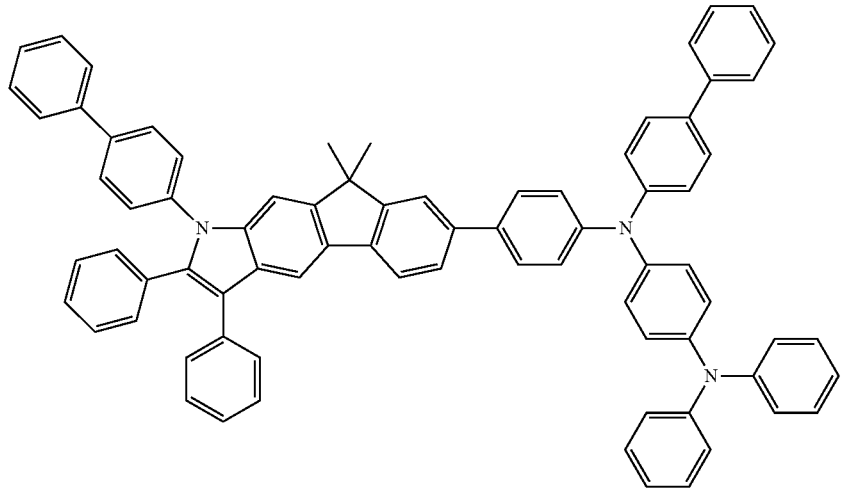
15
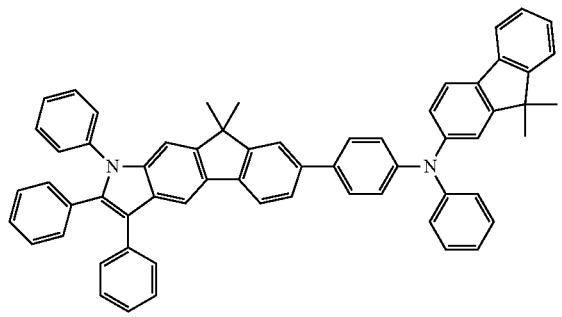
16
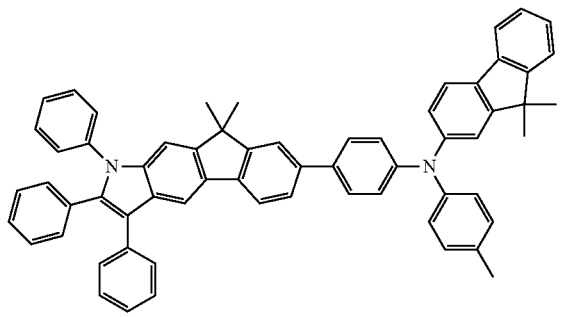
17
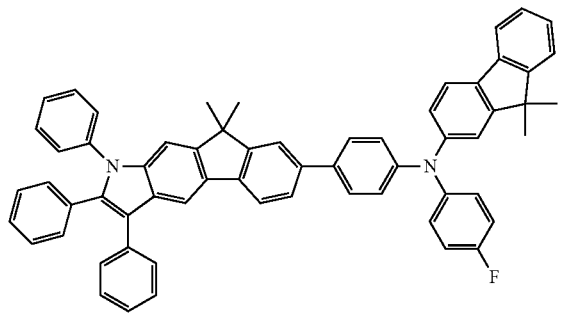
18
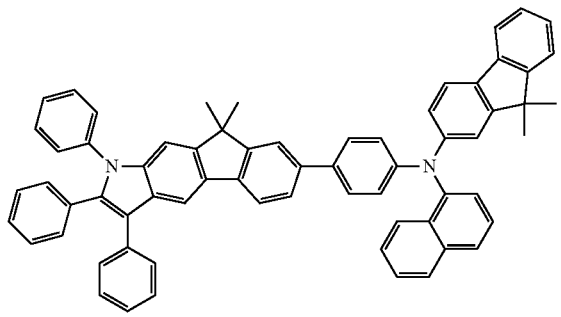
19
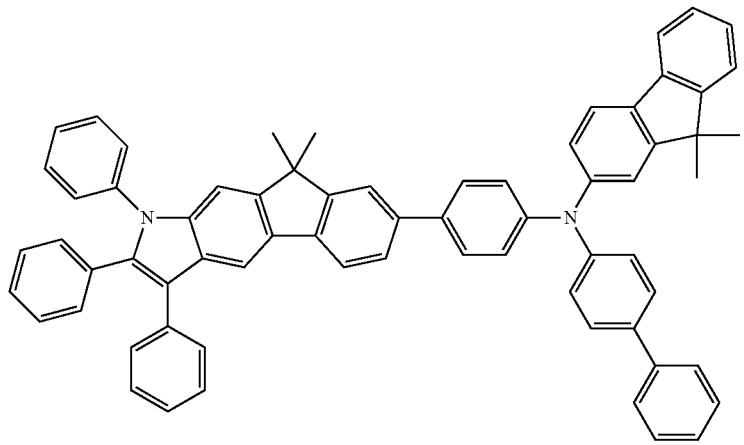
20

-continued
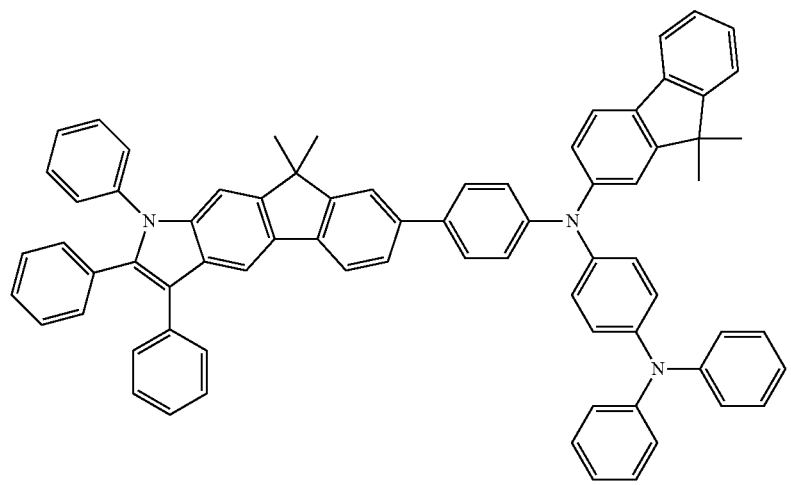
21
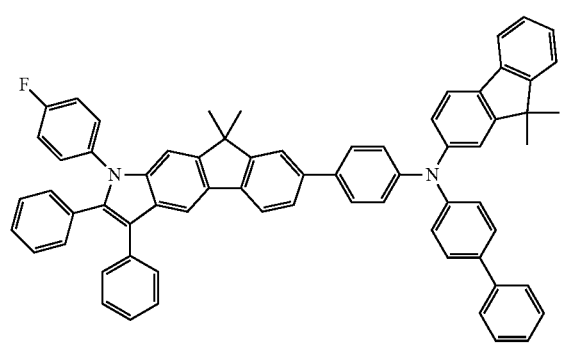
22
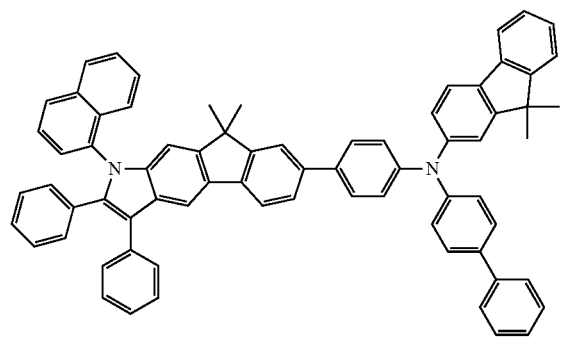
23
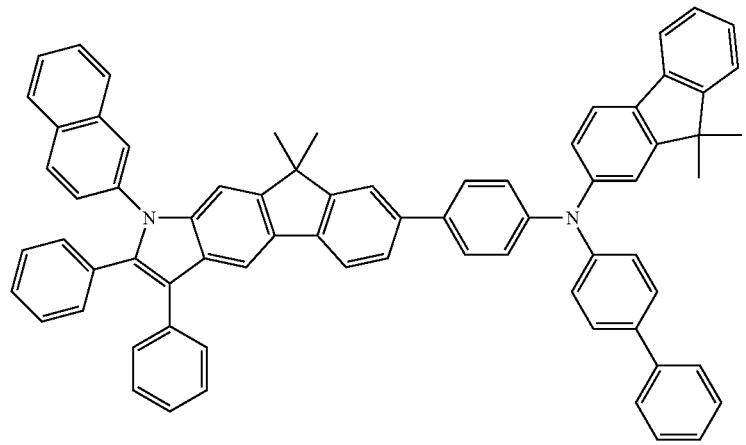
24

-continued
25
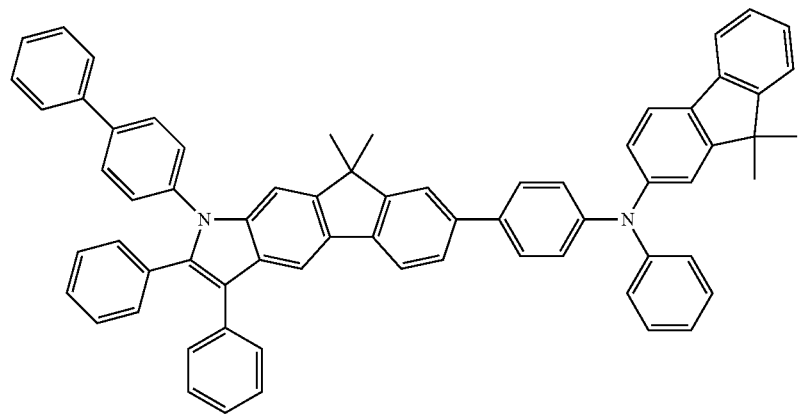
26
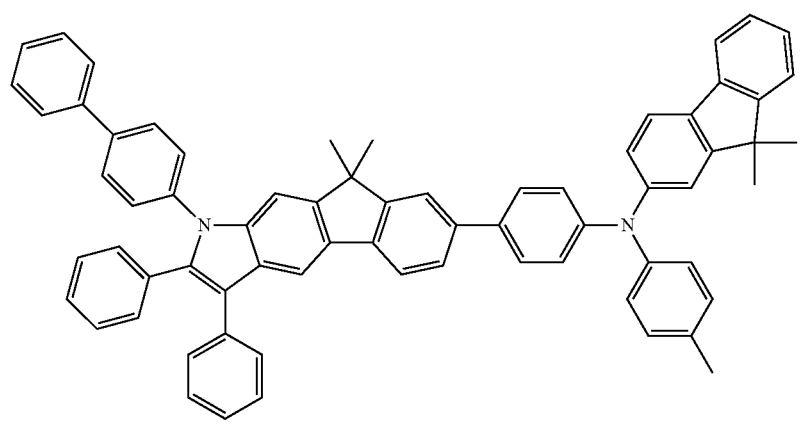
27
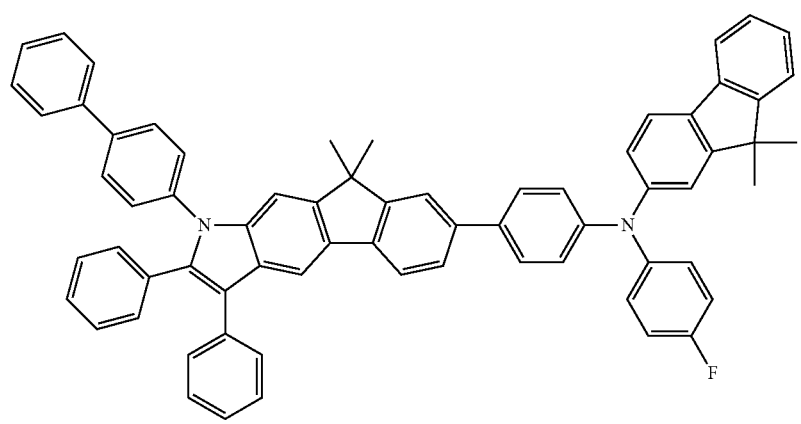

-continued
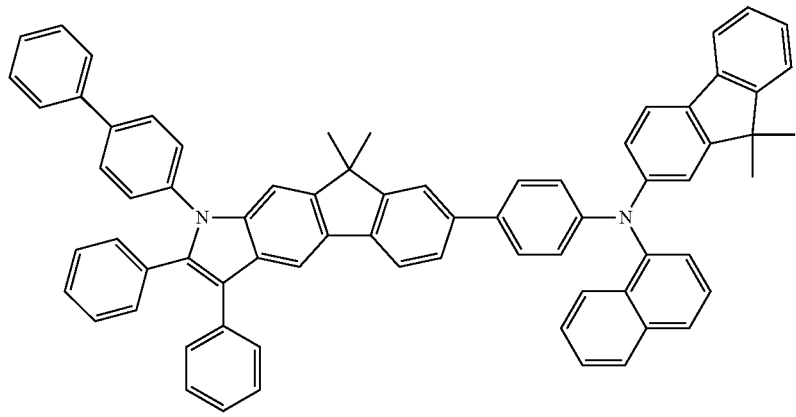
28
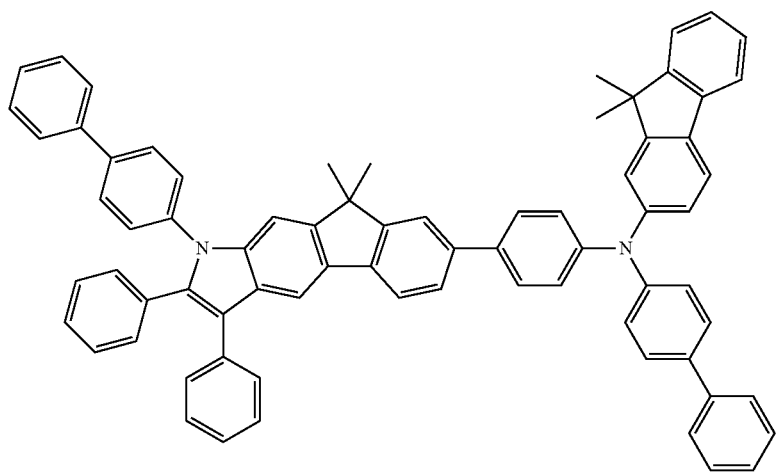
29
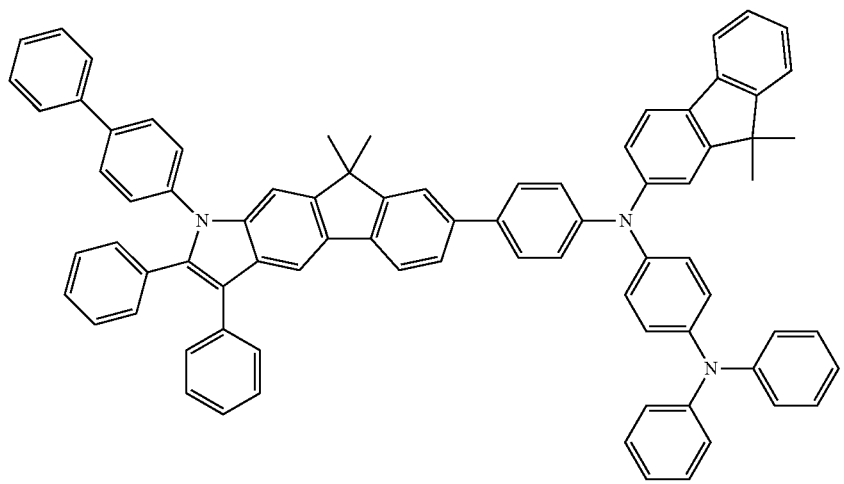
30

-continued
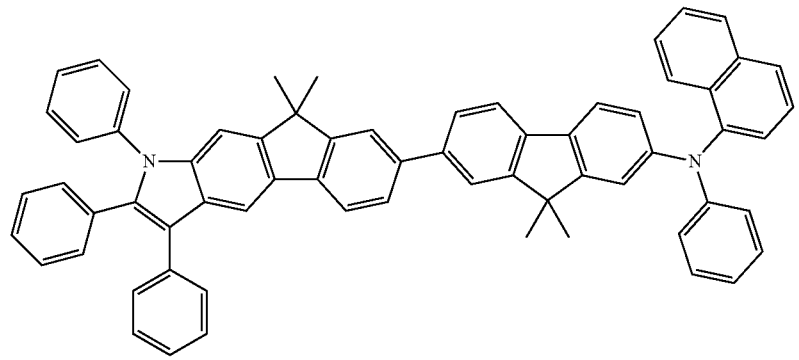
31
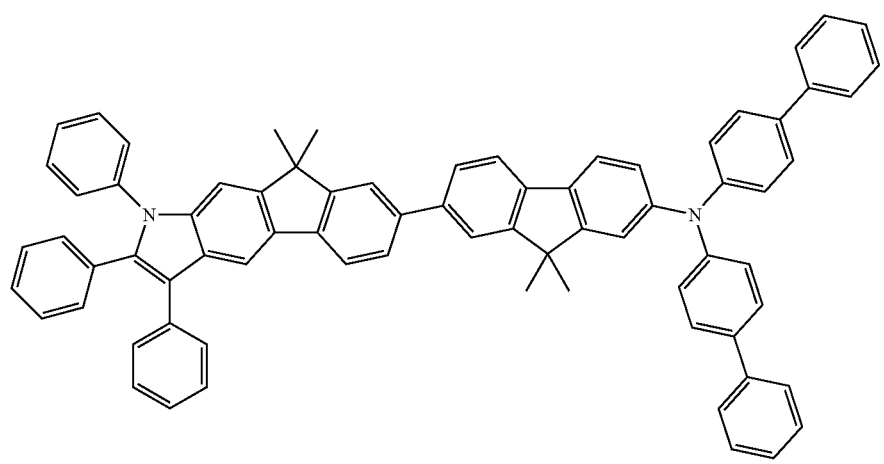
32
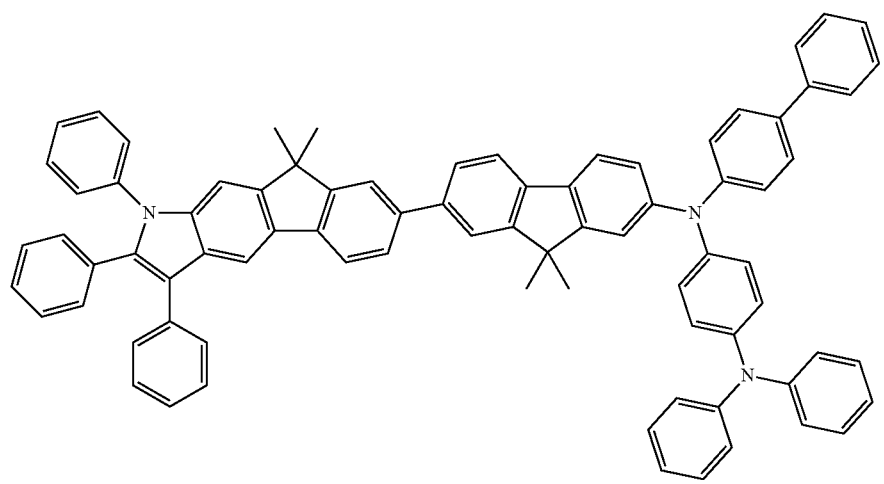
33
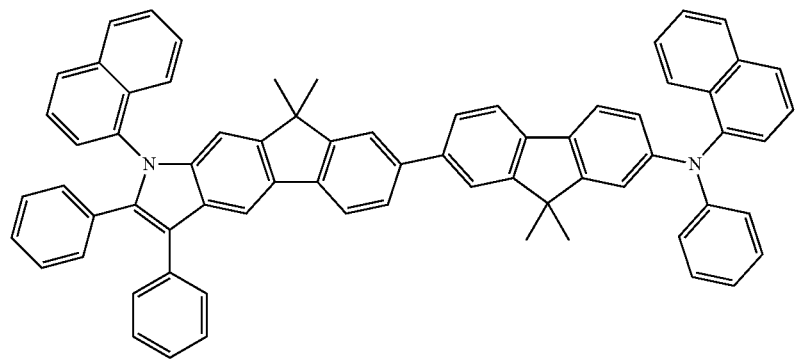
34

35
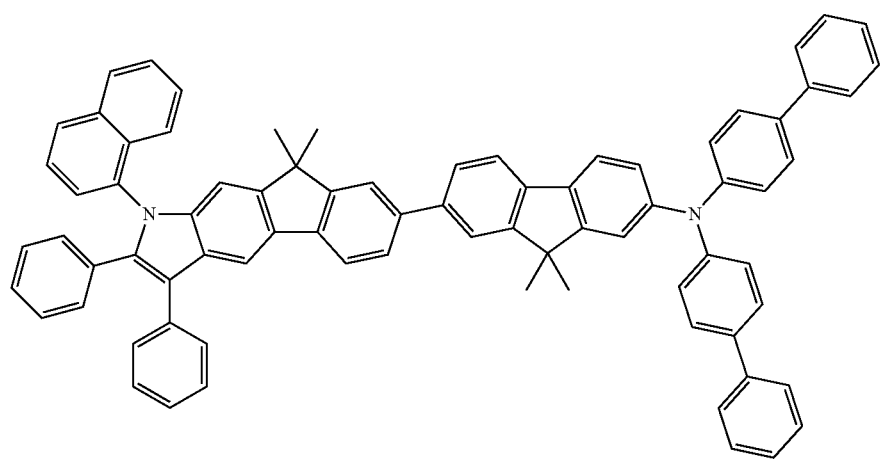
36
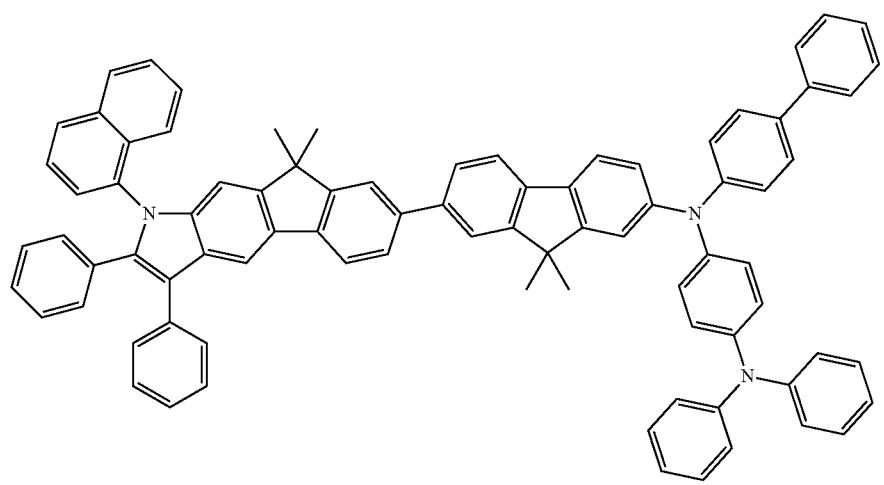
37
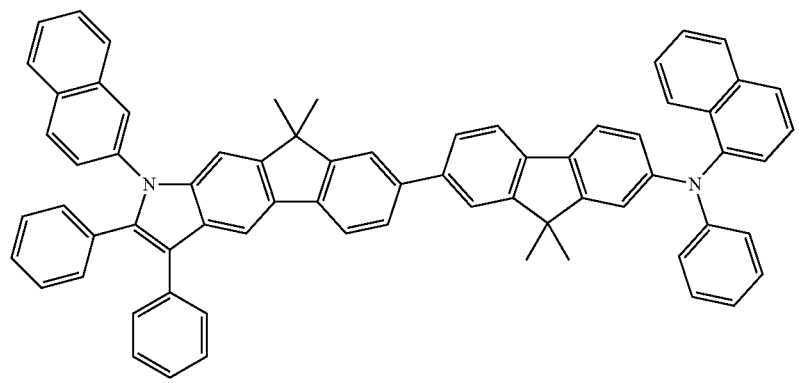

38
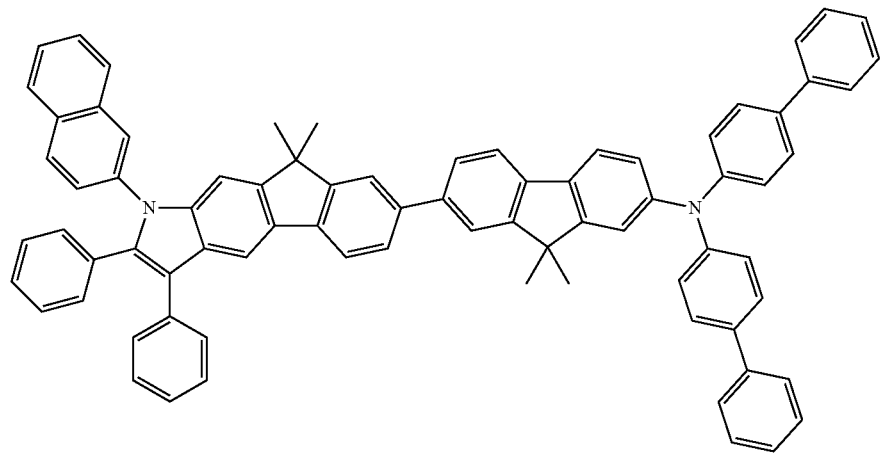
39
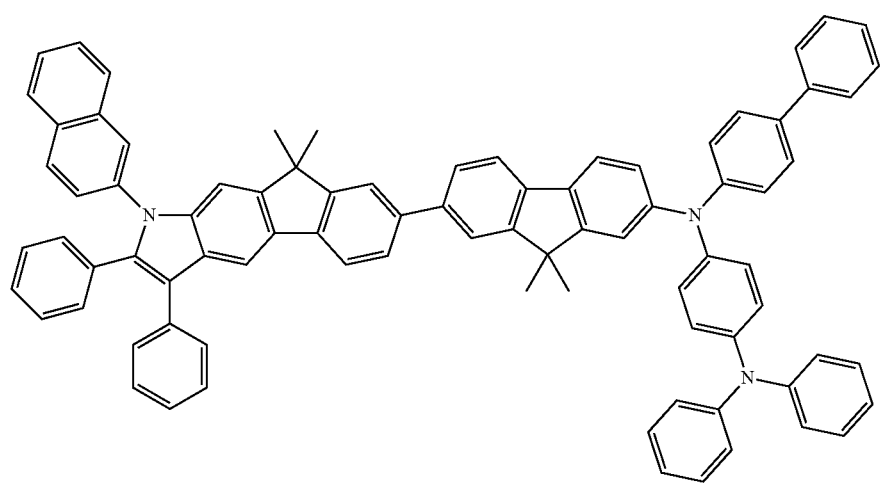
40
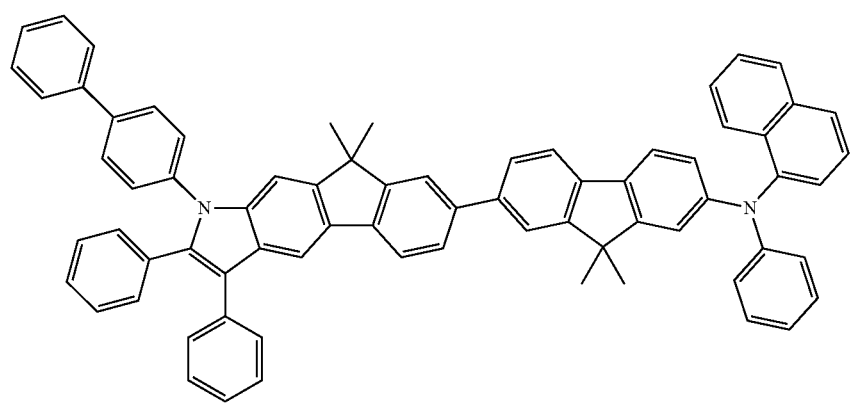

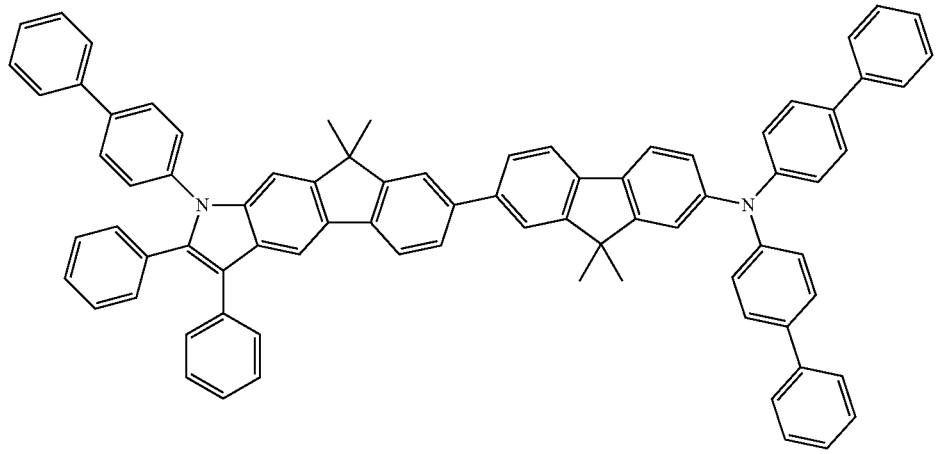
41
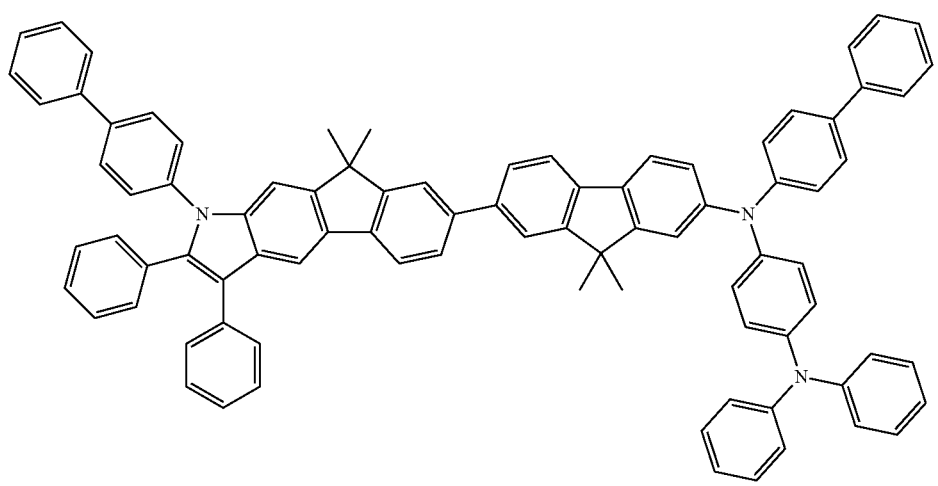
42
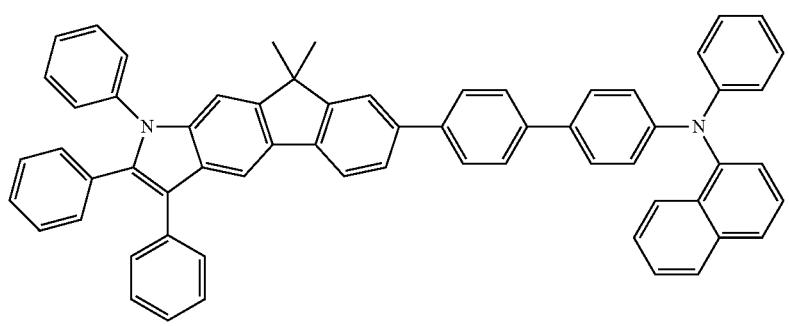
43

44
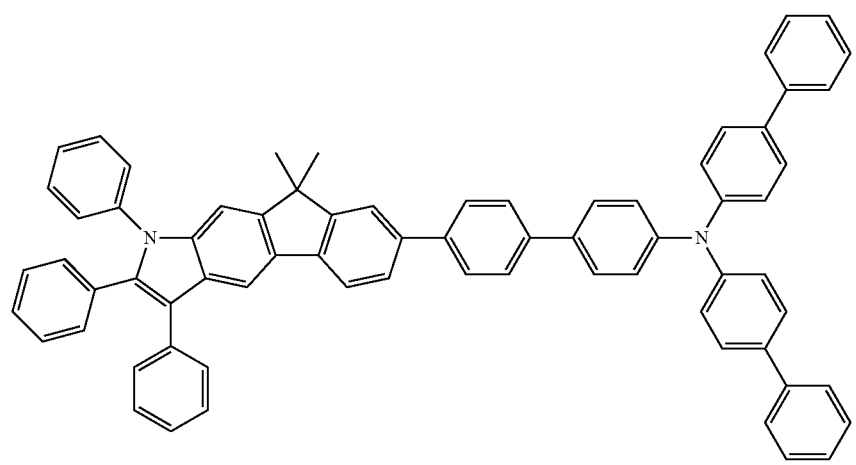
45
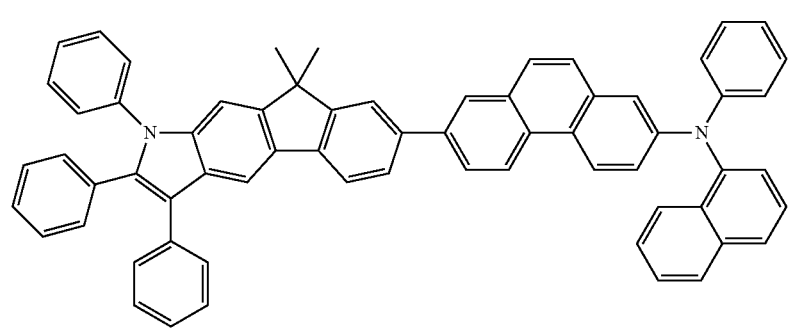
46
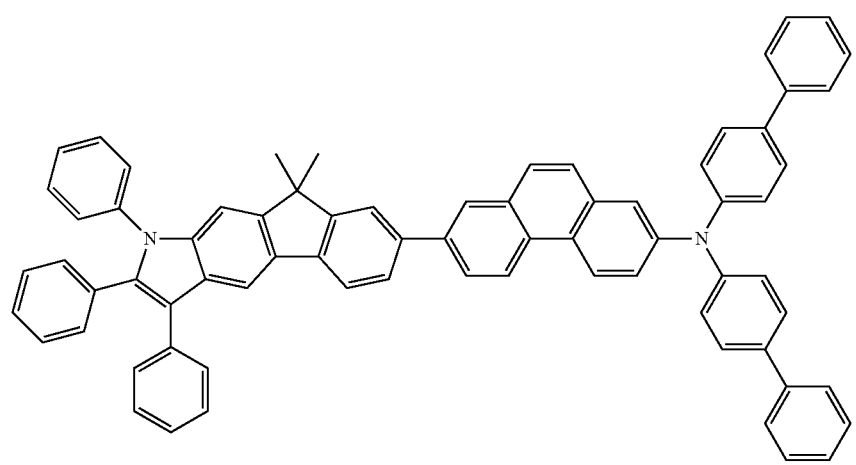
47
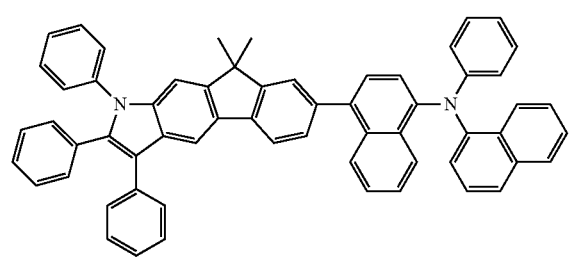
48
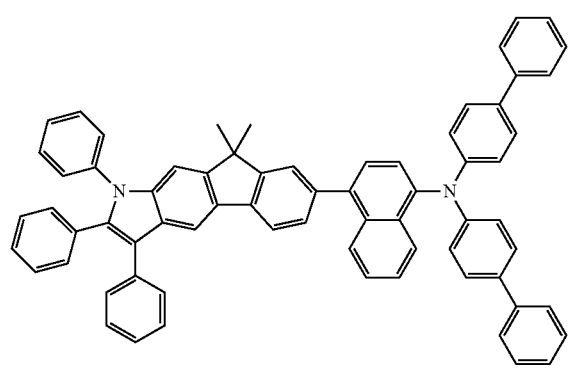

-continued
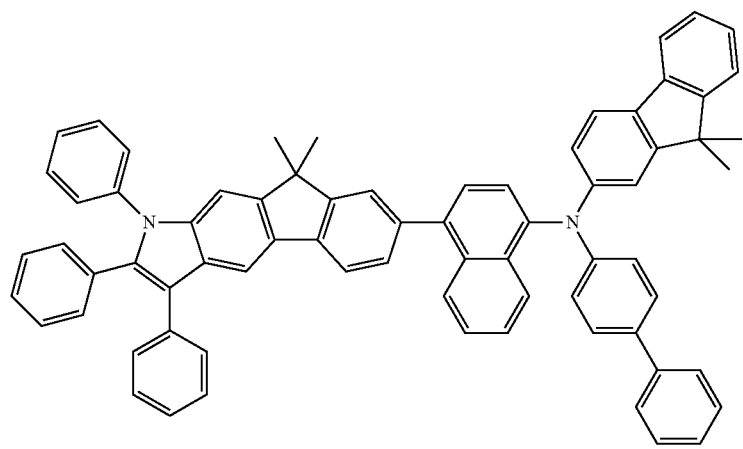
49
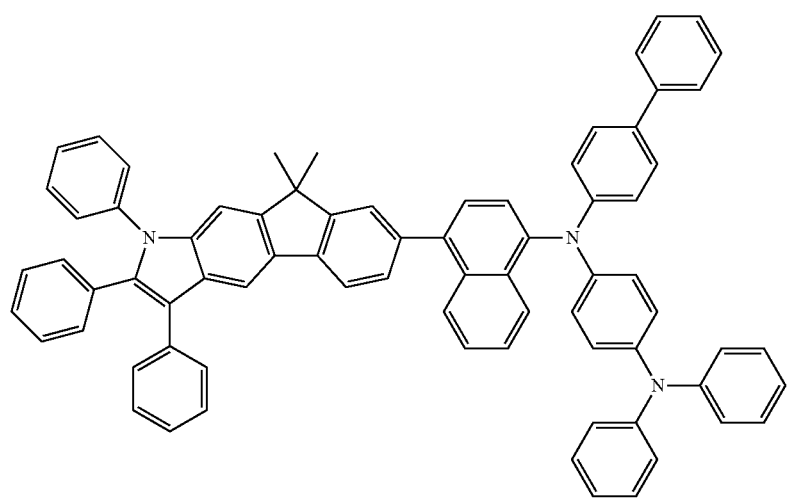
50
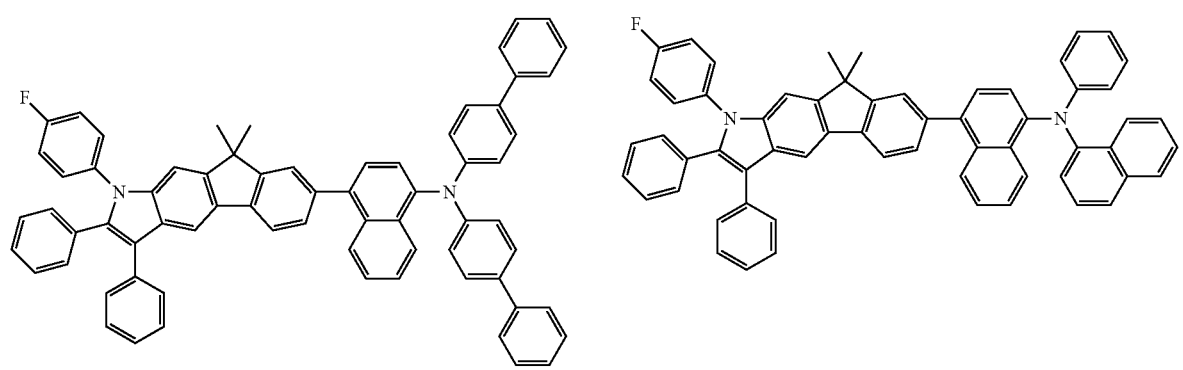
51     52

53
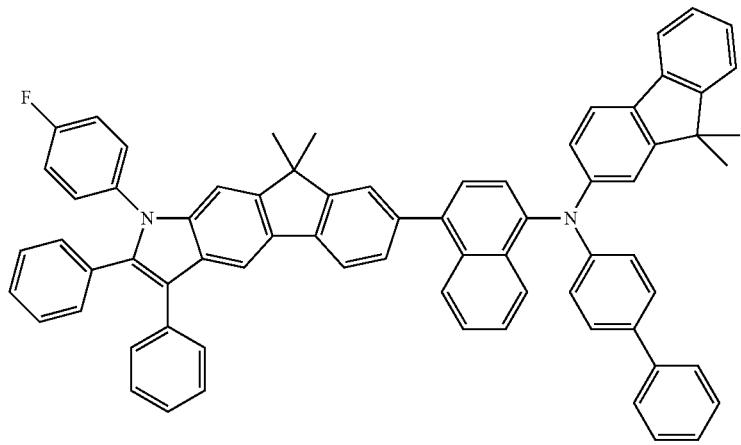
54
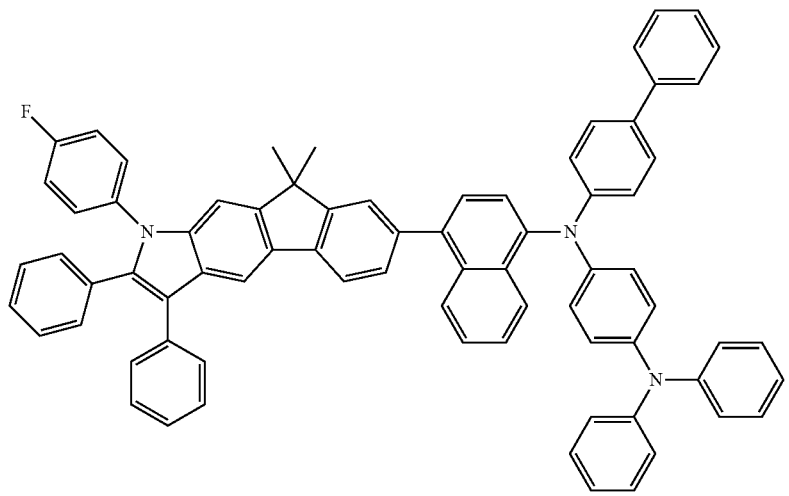
55
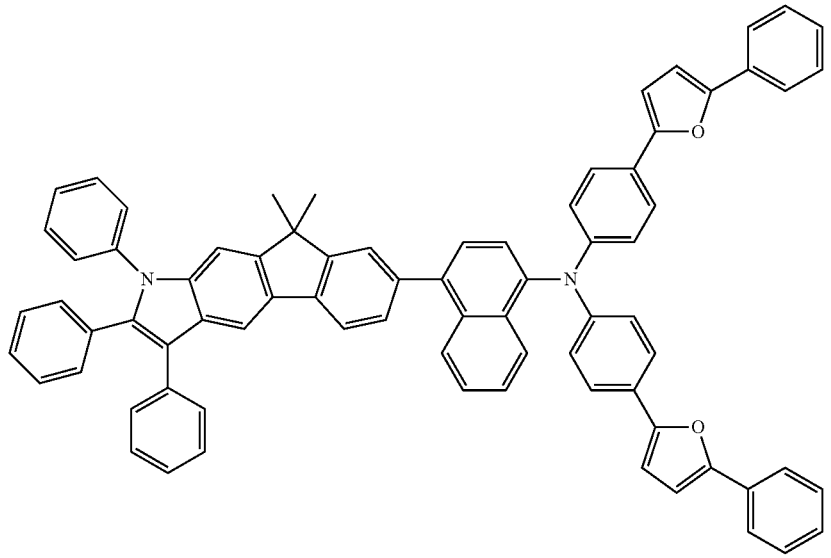

-continued
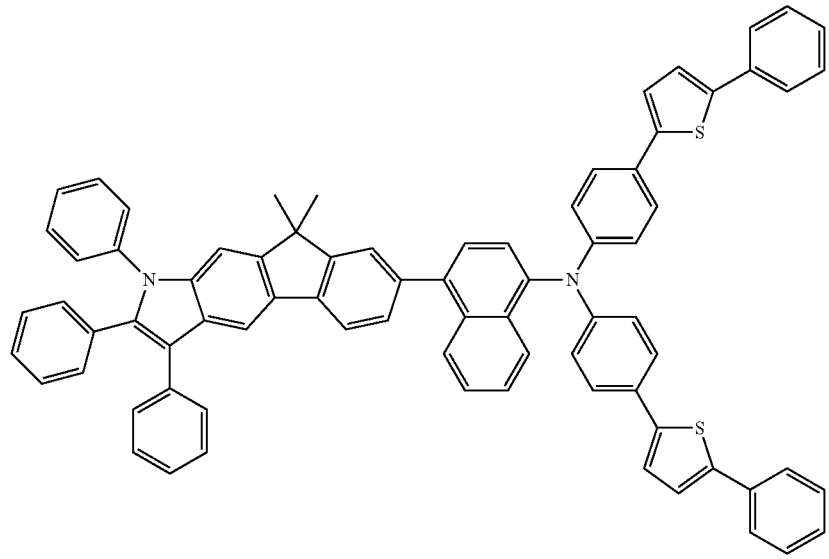
56
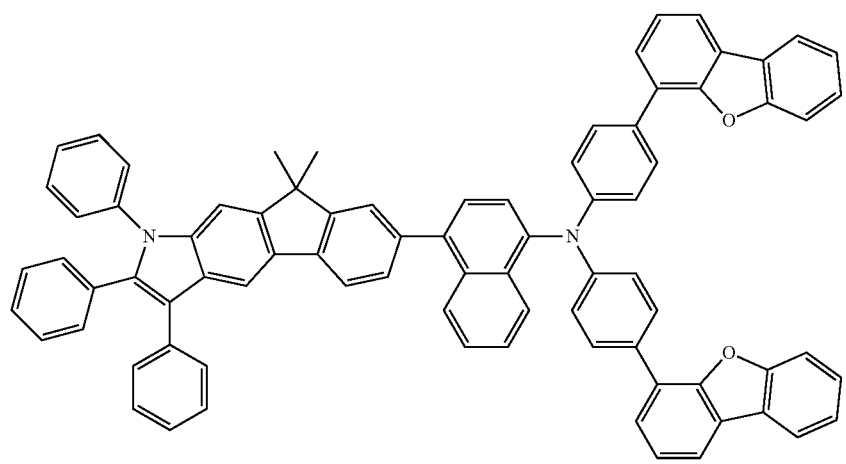
57
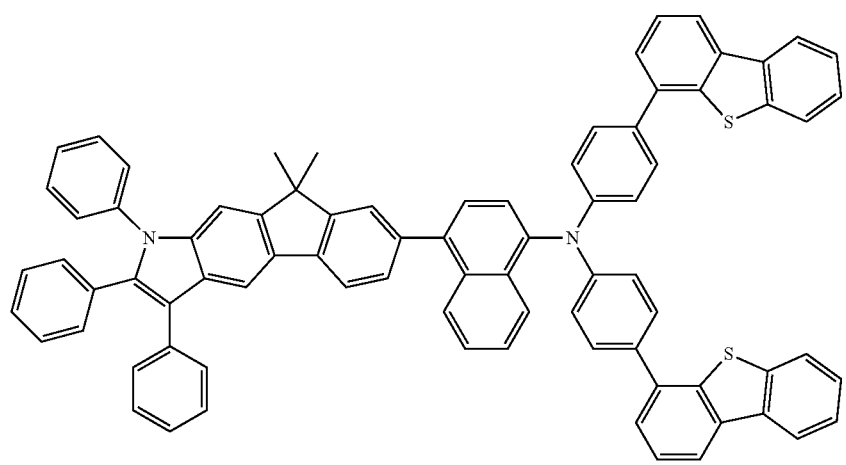
58

59
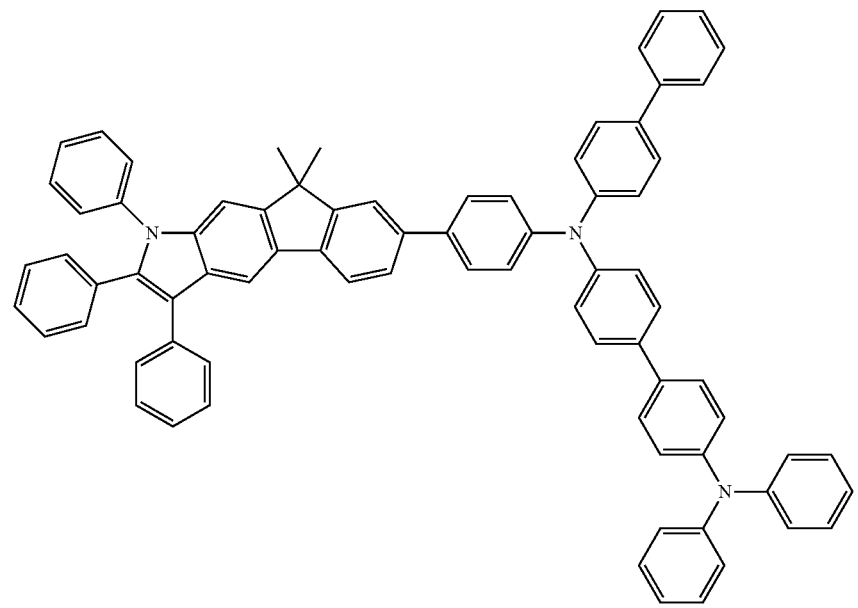
60
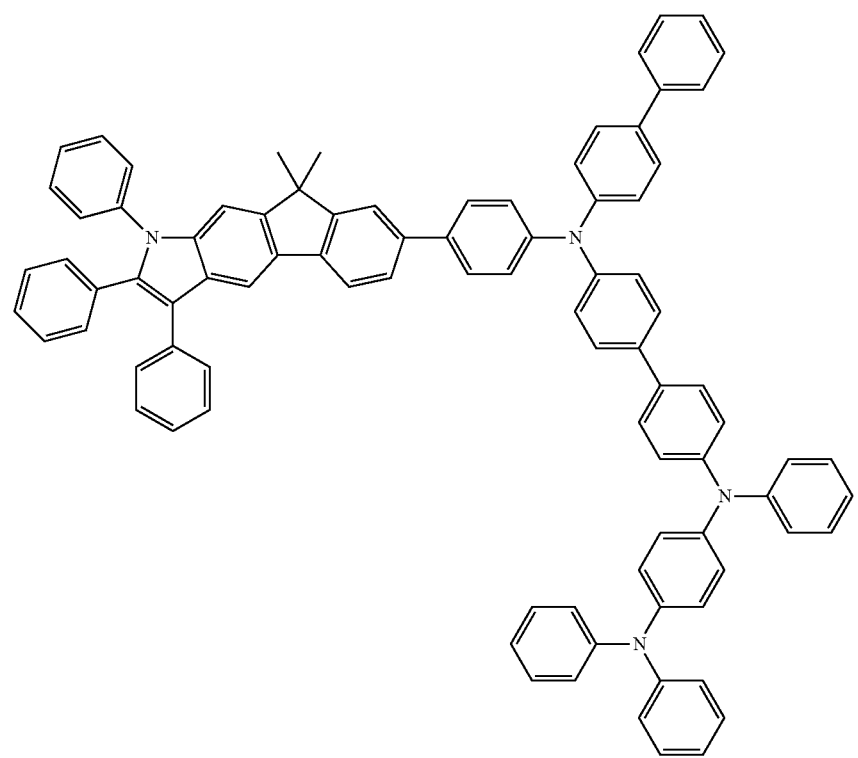

-continued
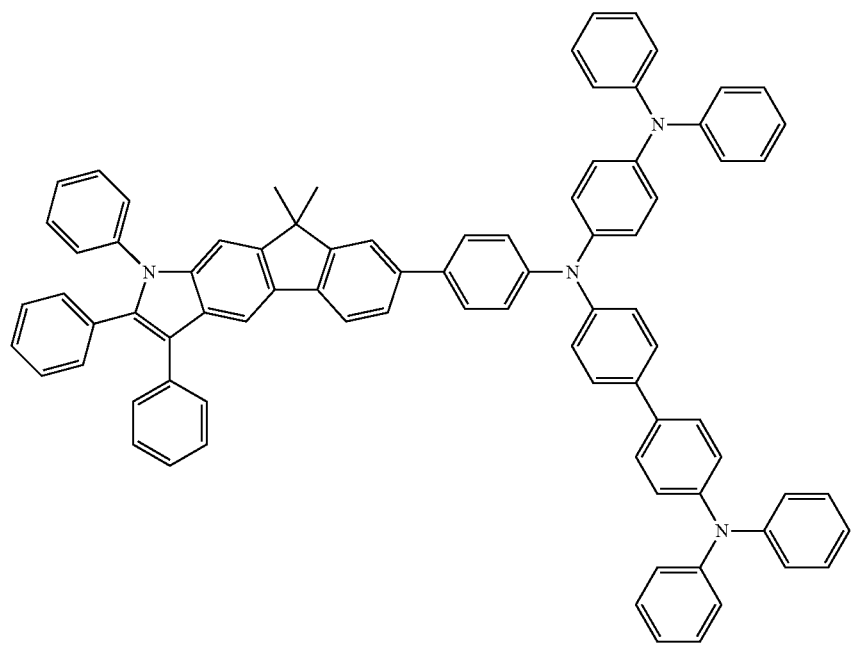
61
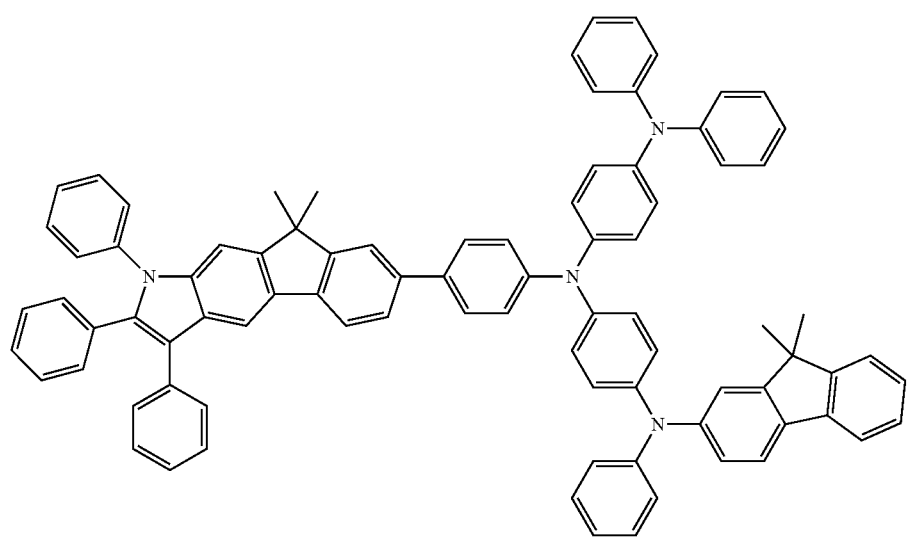
62
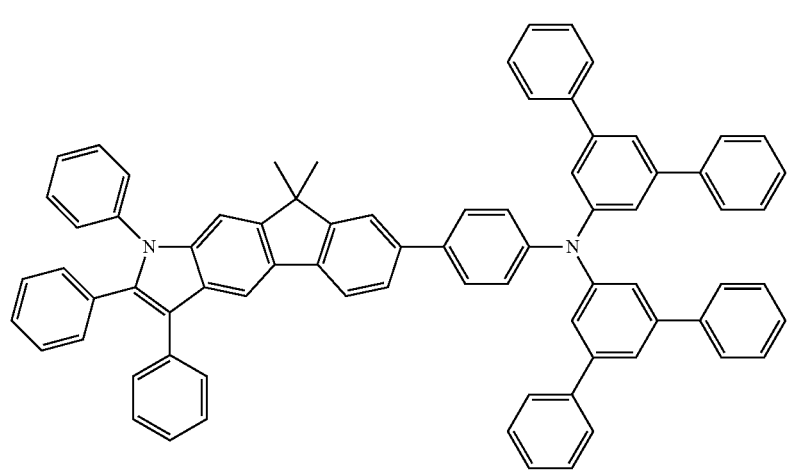
63

-continued
64
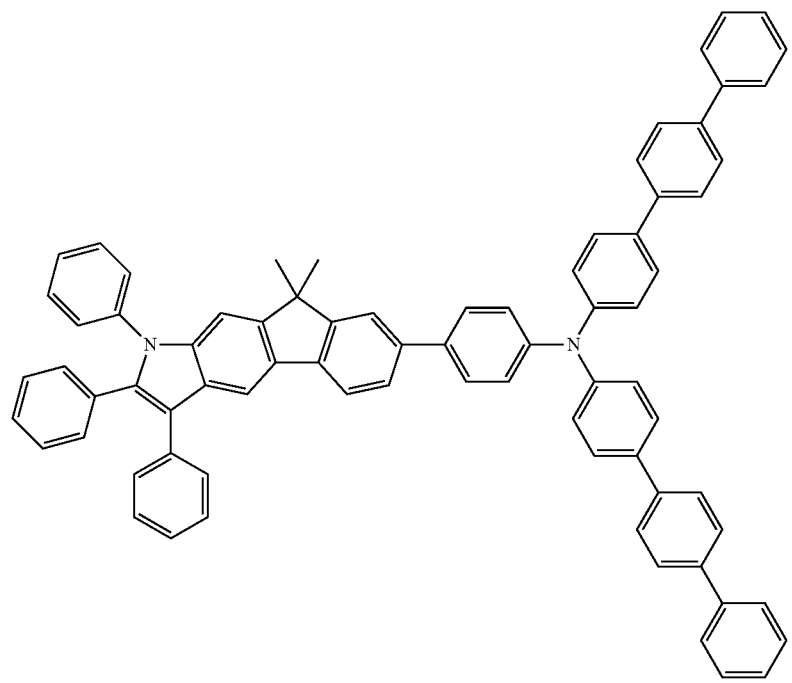
65
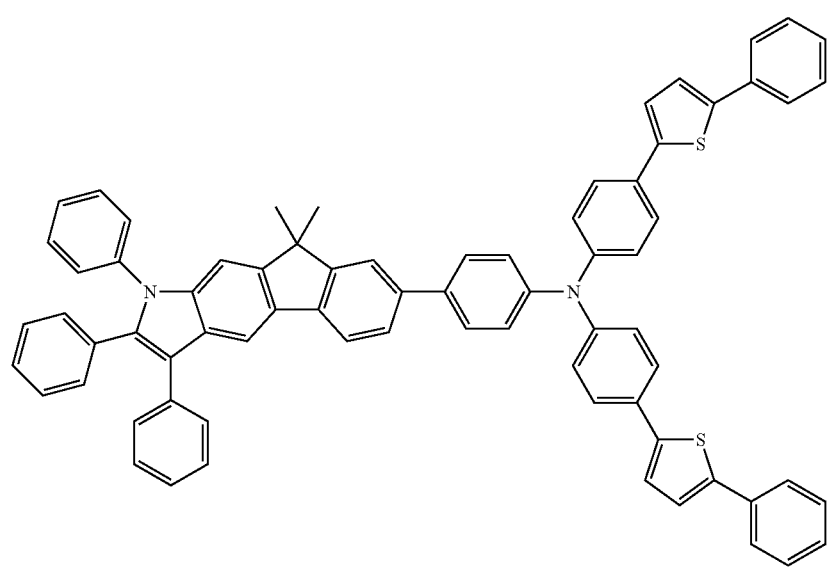

-continued
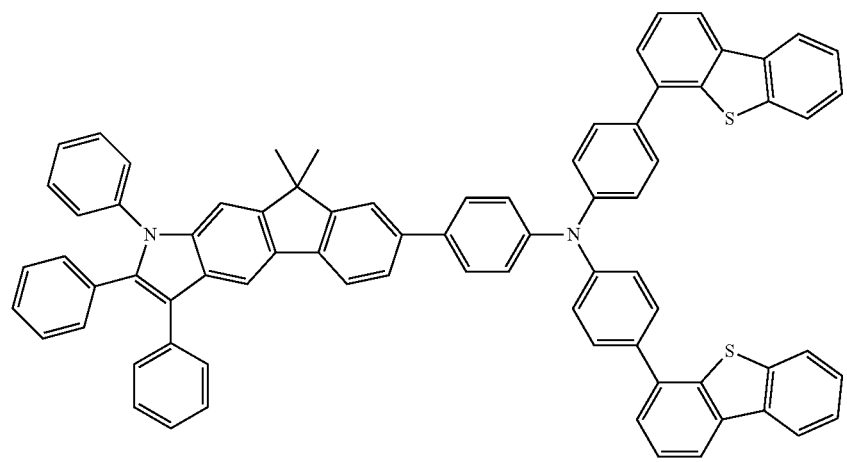
66
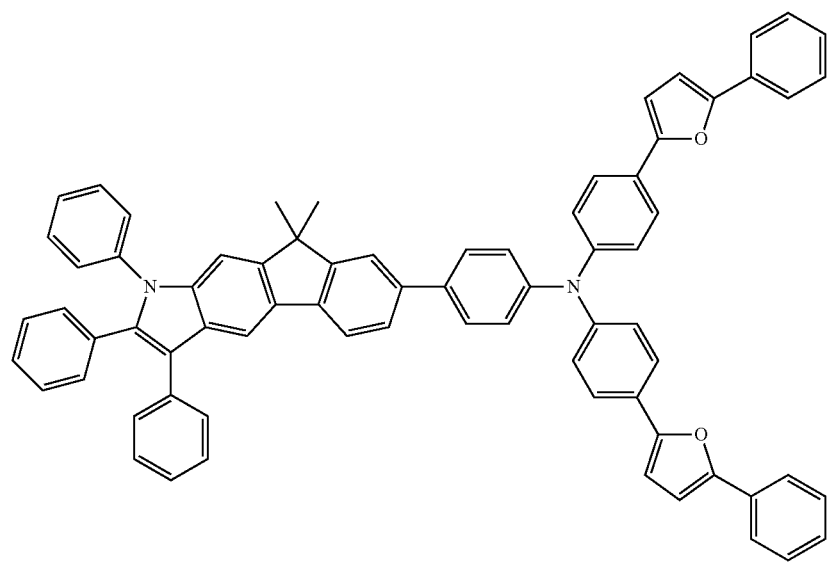
67
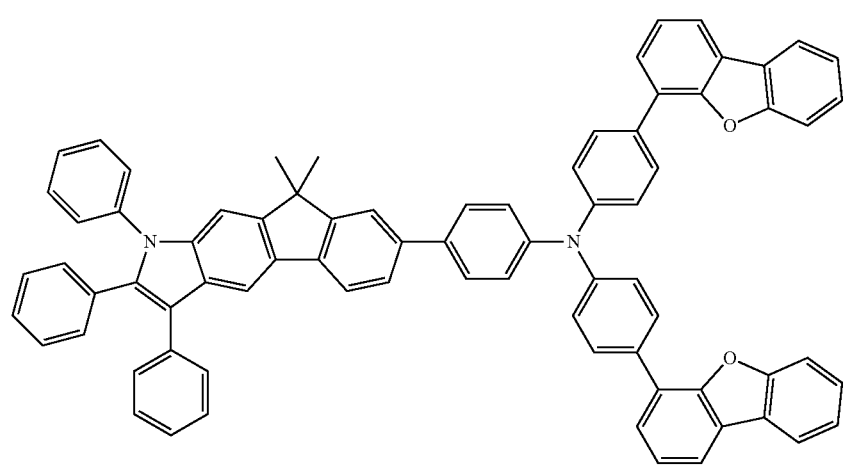
68

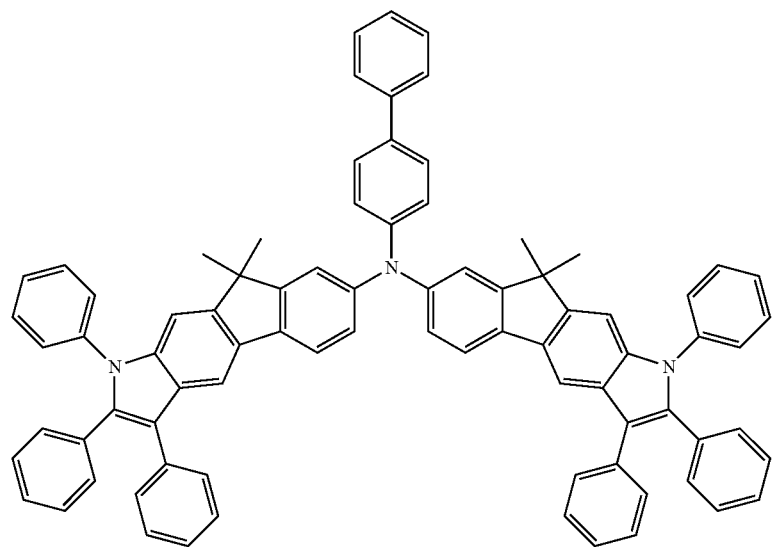
69
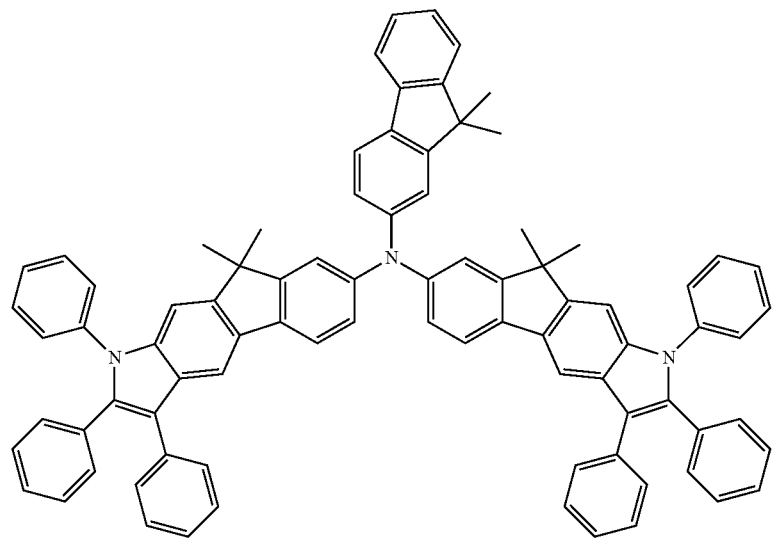
70

-continued
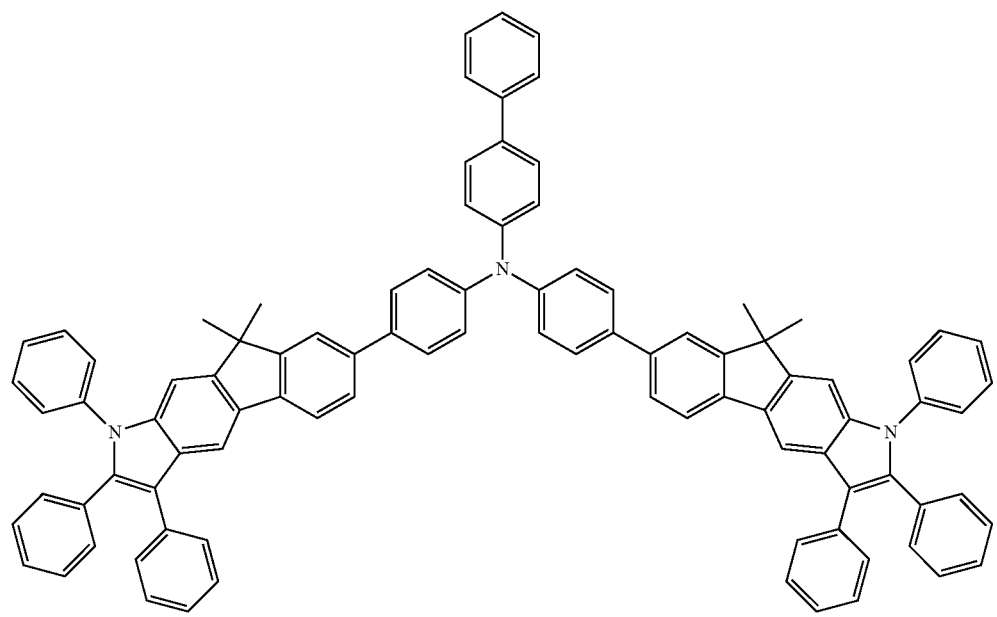
71
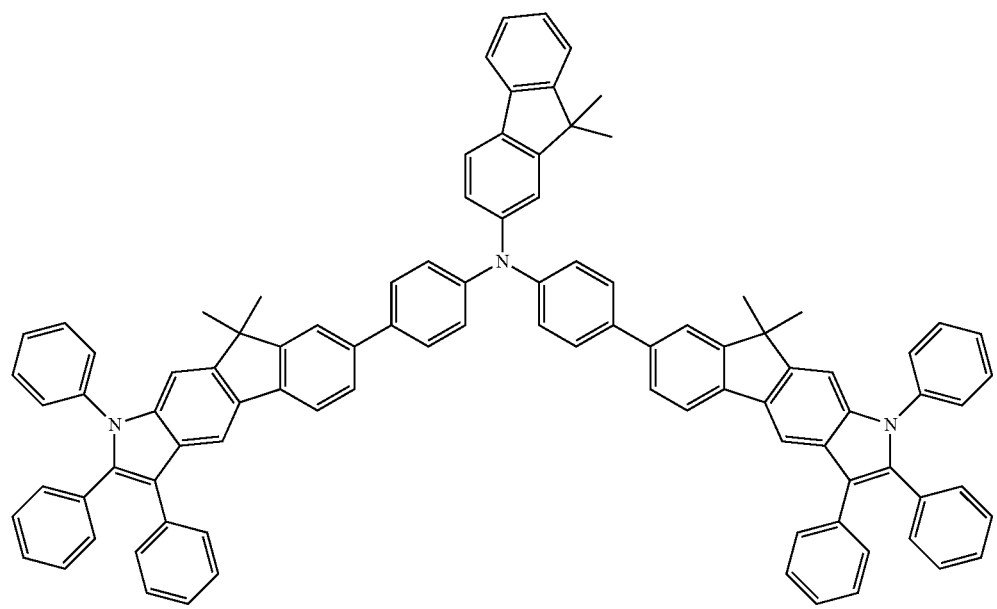
72

-continued
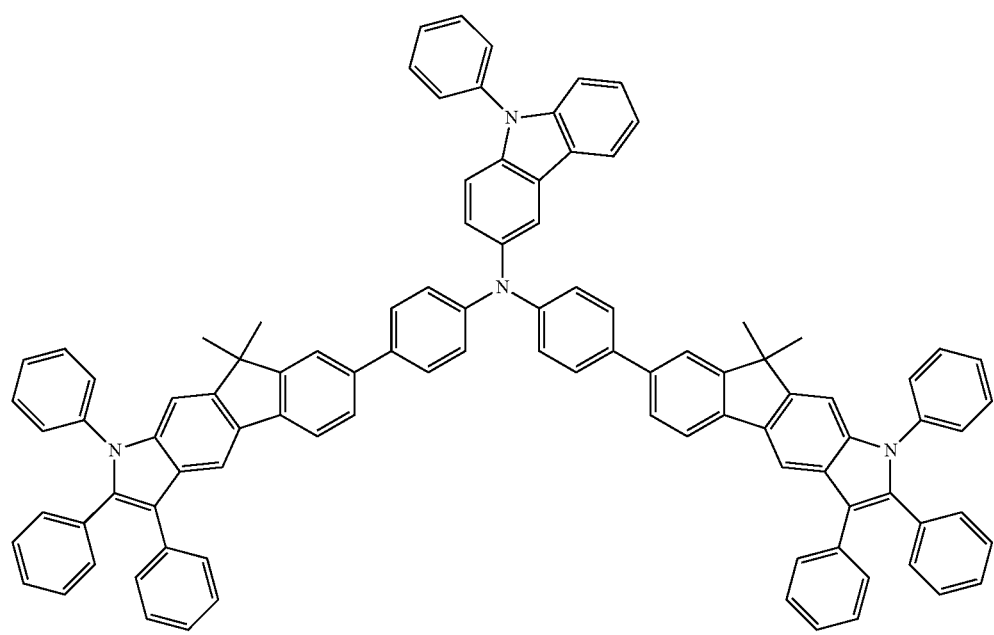
73
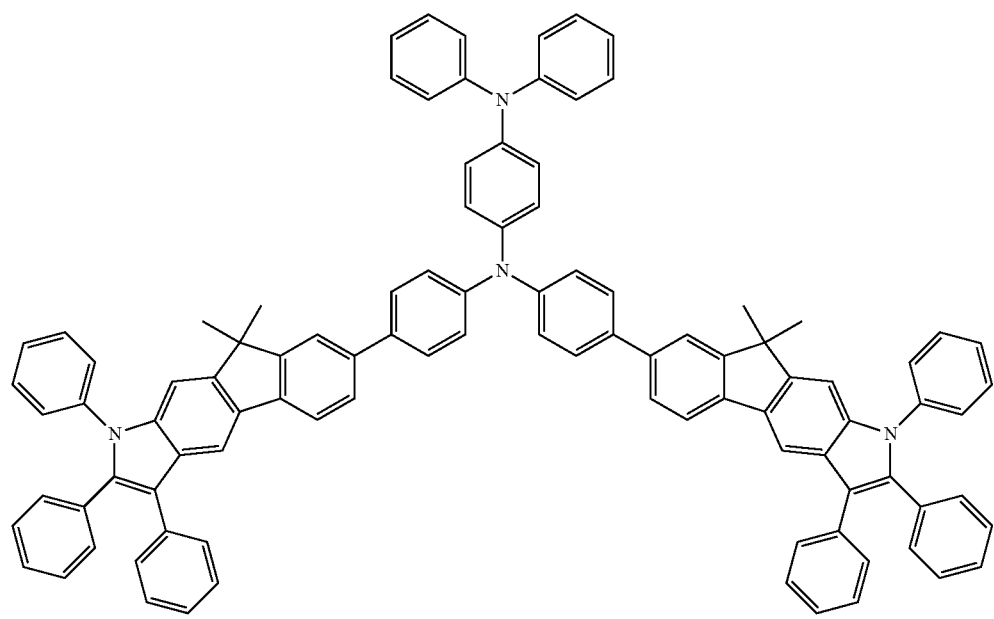
74

75
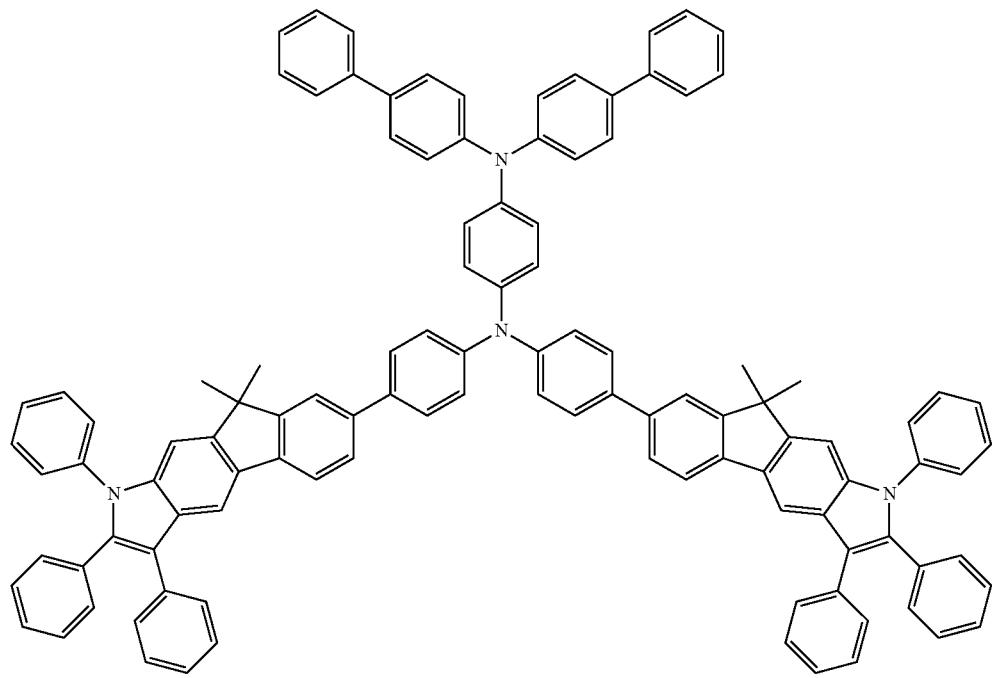
76
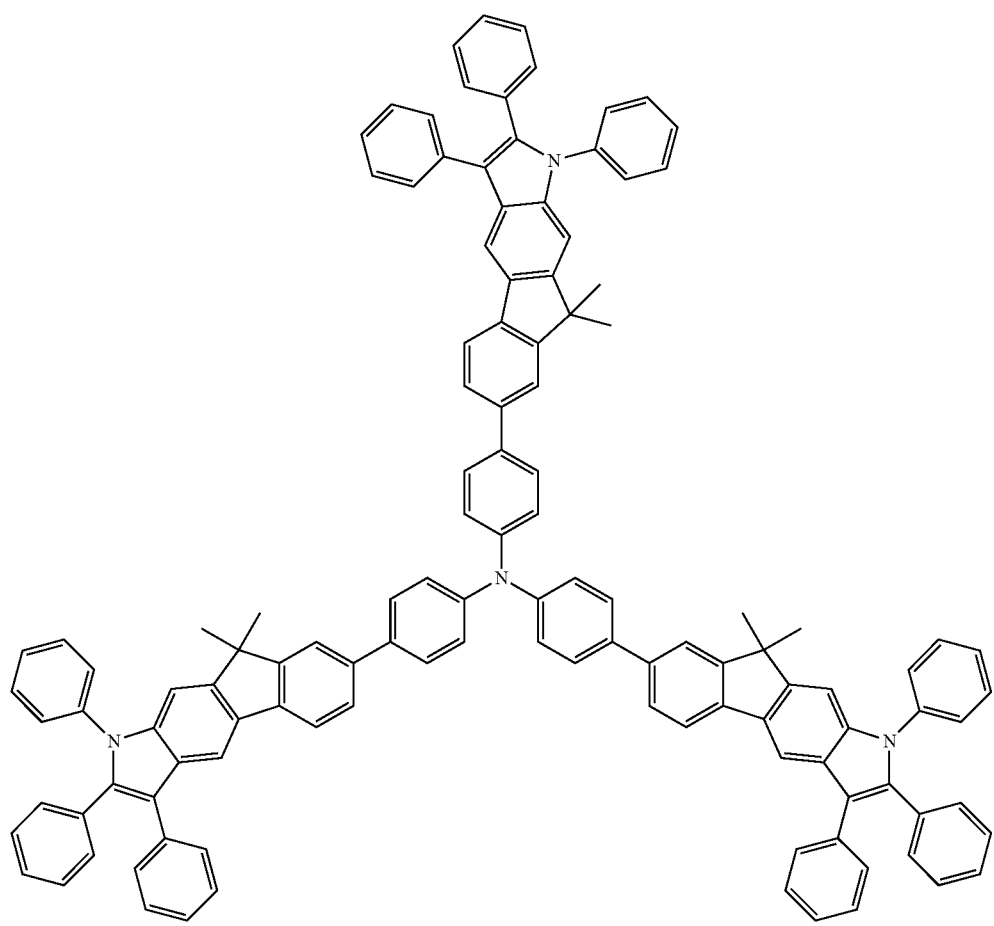

According to other embodiments of the present invention, an organic light-emitting device includes a first electrode, a second electrode, and an organic layer between the first electrode and the second electrode. The organic layer includes the heterocylic compound of Formula 1 described above.

The organic layer (which includes the heterocyclic compound of Formula 1) may be a hole injection layer, a hole transport layer, or a single layer having both hole injection and hole transport capabilities. Alternatively, the organic layer may be an emission layer. When the organic layer is an emission layer, the heterocyclic compound of Formula 1 may be used as a fluorescent host, a phosphorescent host, or a fluorescent dopant.

In the organic light-emitting device, when the emission layer, the hole injection layer or the hole transport layer includes the heterocyclic compound of Formula 1, the emission layer may include an anthracene compound, an arylamine compound or a styryl compound, wherein the anthracene compound, the arylamine compound or the styryl compound may be unsubstituted or substituted with a substituent described above in connection with the $C_1$-$C_{50}$ alkyl group.

In the organic light-emitting device, when the hole injection layer or the hole transport layer includes the heterocyclic compound of Formula 1, a red emission layer, a green emission layer, a blue emission layer or a white emission layer may include a fluorescent compound.

The first electrode may be an anode, and the second electrode may be a cathode, but the reverse is also possible.

In the organic light-emitting described above, the organic layer may further include at least one layer selected from a hole injection layer, a hole transport layer, an electron blocking layer, an emission layer, a hole blocking layer, an electron transport layer and an electron injection layer, if desired. For example, according to some embodiments, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. Alternatively, the organic light-emitting device may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure.

According to some embodiments of the present invention, the organic light emitting device may be a top-emission type organic light-emitting device or a bottom-emission type organic light-emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, an organic light-emitting device includes a substrate, a first electrode (anode), a hole injection layer (HIL), a hole transport layer (HTL), an emission layer (EML), an electron transport layer (ETL), an electron injection layer (EIL), and a second electrode (cathode).

First, the first electrode is formed on a substrate using a deposition or sputtering method. The first electrode may be formed of a first electrode material having a high work function. The first electrode may be an anode or a cathode. The substrate may be a substrate conventionally used in organic light-emitting devices, and may include, for example, a glass substrate or a transparent plastic substrate, which has excellent mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

Next, the HIL may be formed on the first electrode using various methods, for example, vacuum deposition, spin coating, casting, Langmuir-Blodgett (LB) deposition, or the like. When the HIL is formed using vacuum deposition, the deposition conditions may vary according to the compound used to form the HIL, and the structure and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the compound used to form the HIL, and the structure and thermal properties of the HIL to be formed. For example, the coating conditions may include a coating speed of about 2000 rpm to about 5000 rpm, and a thermal treatment temperature of about 80° C. to about 200° C., wherein the thermal treatment serves to remove the solvent after coating.

The HIL material may include the heterocyclic compound of Formula 1 described above. Alternatively, known HIL materials may also be used. Nonlimiting examples of such HIL materials include phthalocyanine compounds such as copper phthalocyanine, 4,4',4"-tris(3-methylphenylphenylamino)triphenylamine (m-MTDATA), N,N'-di(1-naphthyl)-N,N'-diphenylbenzidine) (NPB), TDATA, 2-TNATA, polyaniline/dodecylbenzenesulfonic acid (Pani/DBSA), poly(3,4-ethylenedioxythiophene)/poly(4-styrenesulfonate)(PEDOT/PSS), polyaniline/camphor sulfonic acid (Pani/CSA), and (polyaniline)/poly(4-styrenesulfonate) (PANI/PSS).

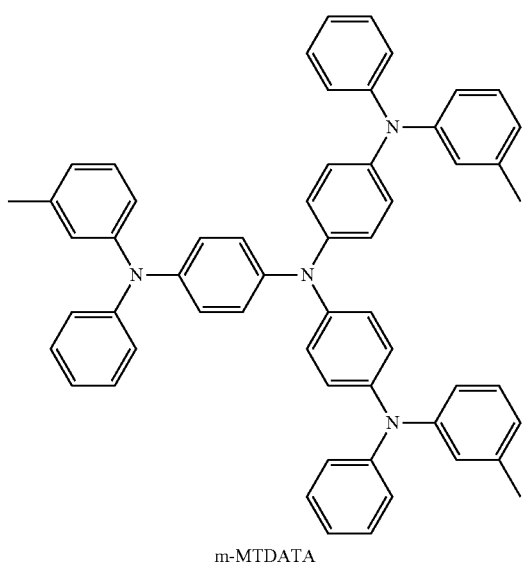

m-MTDATA

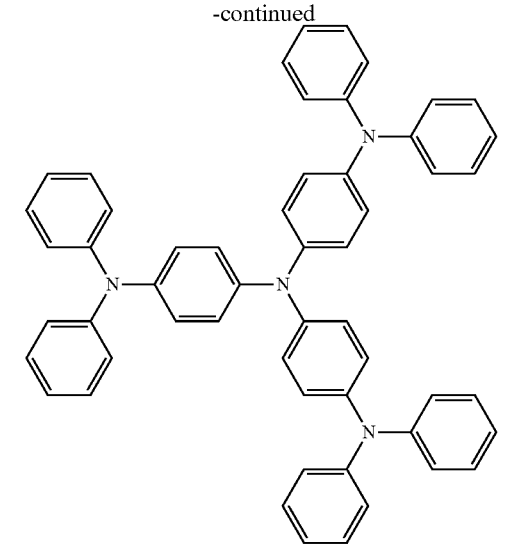

TDATA

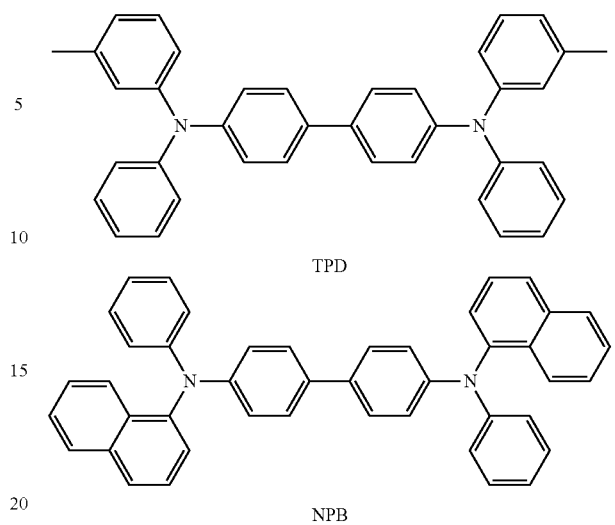

TPD

NPB

The HIL may have a thickness of about 100 Å to about 10,000 Å. For example, the HIL may have a thickness of about 100 Å to about 1000 Å. When the HIL has a thickness within these ranges, the HIL may have good hole injection characteristics without an increase in driving voltage.

Next, the HTL may be formed on the HIL using various methods, for example vacuum deposition, spin coating, casting, LB deposition, or the like. When the HTL is formed using vacuum deposition or spin coating, the deposition or coating conditions may be similar to those used to form the HIL, although the deposition or coating conditions may vary according to the material that is used to form the HTL.

The HTL material may include the heterocyclic compound of Formula 1 described above. Alternatively, known HTL materials may be used. Nonlimiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD). Among these materials, TCTA may not only transport holes but also inhibit excitons from being diffused from the EML.

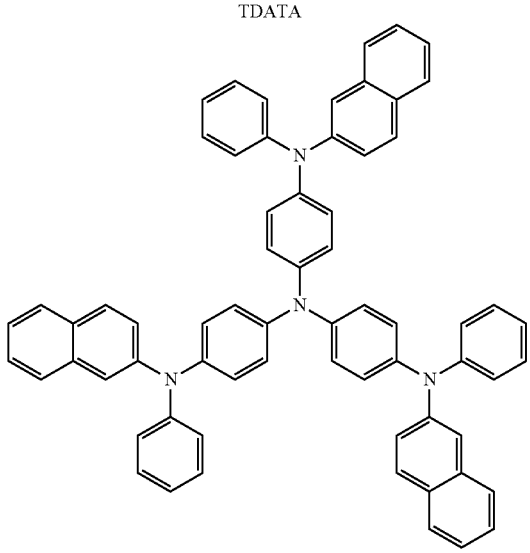

2-TNATA

The HTL may have a thickness of about 50 Å to about 1000 Å. For example, the HTL may have a thickness of about 100 Å to about 600 Å. When the HTL has a thickness within these ranges, the HTL may have good hole transport characteristics without a substantial increase in driving voltage.

Next, the EML may be formed on the HTL using various methods, for example, vacuum deposition, spin coating, casting, LB deposition, or the like. When the EML is formed using vacuum deposition or spin coating, the deposition or coating conditions may be similar to those used to form the HIL, although the deposition and coating conditions may vary according to the material that is used to form the EML.

The EML may include the heterocyclic compound of Formula 1 described above. In particular, the heterocyclic compound of Formula 1 may be used as a host or a dopant. The EML may be formed using a variety of known light-emitting materials, in addition to the heterocyclic compound of Formula 1. Alternatively, the EML may be formed using a known host and a dopant. The dopant used to form the EML may include either a fluorescent dopant or a phosphorescent dopant.

Nonlimiting examples of suitable hosts include Alq$_3$, CPB (4,4'-N,N'-dicarbazole-biphenyl), 9,10-di(naphthalen-2-yl)anthracene (ADN), and distyrylarylene (DSA).

Nonlimiting examples of red dopants include platinum(II) octaethylporphyrin (PtOEP), Ir(piq)$_3$, Btp$_2$Ir(acac), and DCJTB.

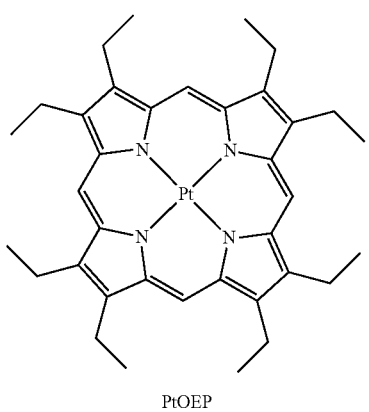

PtOEP

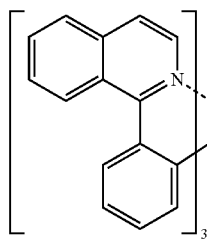
Ir(piq)₃

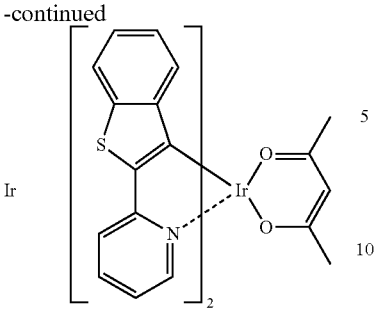
Btp₂Ir(acac)

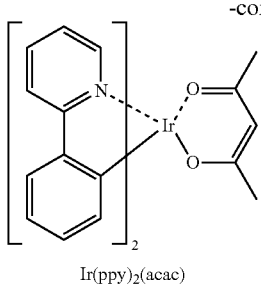
Ir(ppy)₂(acac)

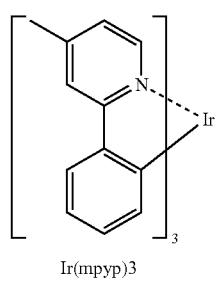
Ir(mpyp)3

Nonlimiting examples of green dopants include Ir(ppy)₃ (where "ppy" denotes phenylpyridine), Ir(ppy)₂(acac), Ir(m-pyp)₃, and C545T.

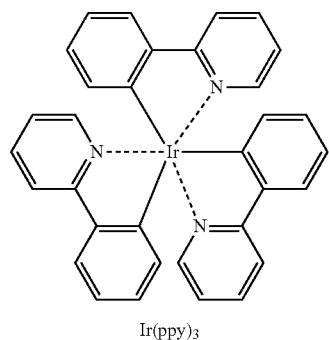
Ir(ppy)₃

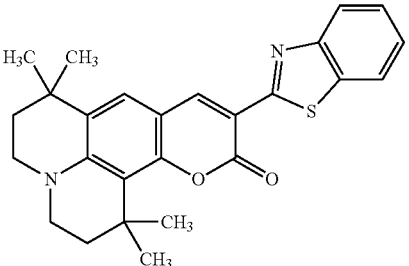
C545T

Nonlimiting examples of blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBP).

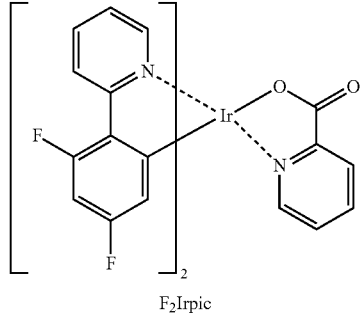
F₂Irpic

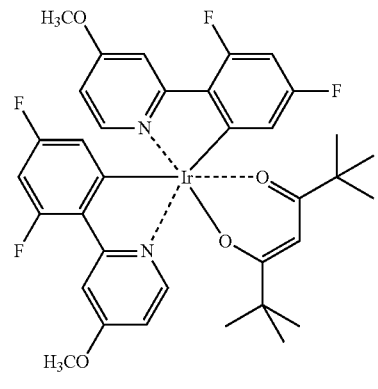
(F₂ppy)₂Ir(tmd)

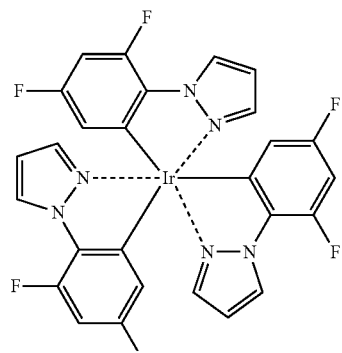
Ir(dfppz)₃

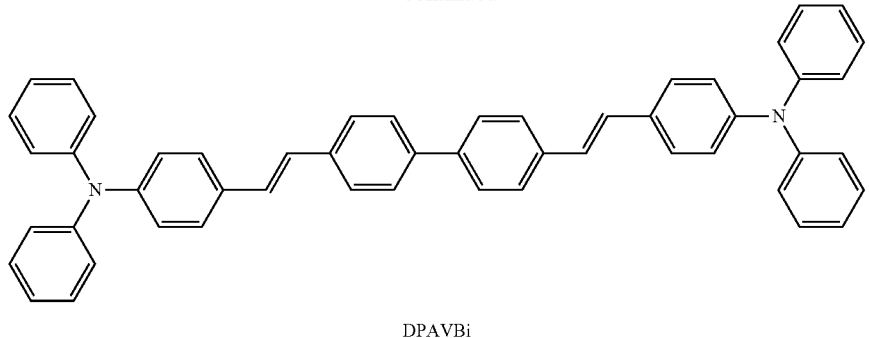

DPAVBi

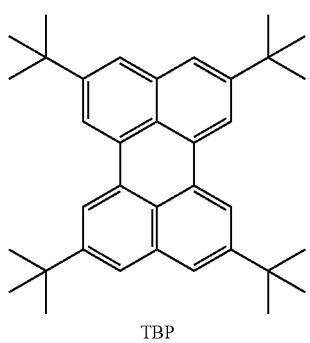

TBP

The amount of the dopant may be about 0.1 to about 20 parts by weight, or about 0.5 to about 12 parts by weight, based on 100 parts by weight of the EML material (which is equivalent to the total weight of the host and the dopant). When the amount of the dopant is within these ranges, concentration quenching may be substantially prevented.

The EML may have a thickness of about 100 Å to about 1000 Å. For example, the EML may have a thickness of about 200 Å to about 600 Å. When the EML has a thickness within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL, without limitation. Nonlimiting examples of such HBL materials include oxadiazole derivatives, triazole derivatives, phenathroline derivatives, Balq, and BCP.

The HBL may have a thickness of about 50 Å to about 1000 Å. For example, the HBL may have a thickness of about 100 Å to about 300 Å. When the HBL has a thickness within these ranges, the HBL may have excellent hole blocking characteristics without a substantial increase in driving voltage.

Next, the ETL is formed on the EML (or HBL) using various methods, for example, vacuum deposition, spin coating, casting, or the like. When the ETL is formed using vacuum deposition or spin coating, the deposition or coating conditions may be similar to those used to form the HIL, although the deposition and coating conditions may vary according to the material that is used to form the ETL.

The ETL material may include the heterocyclic compound of Formula 1 described above. Alternatively, the ETL may be formed of any known material. Nonlimiting examples of such ETL materials include quinoline derivatives, such as tris(8-quinolinolate)aluminum ($Alq_3$), TAZ, or Balq.

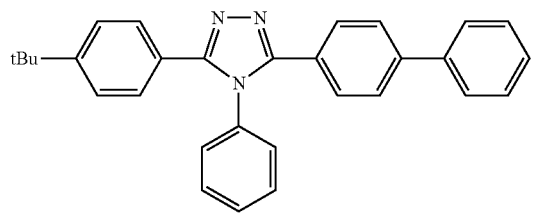

TAZ

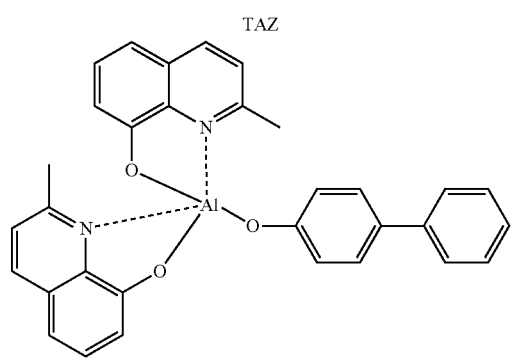

BAlq

The ETL may have a thickness of about 100 Å to about 1000 Å. For example, the ETL may have a thickness of about 100 Å to about 500 Å. When the ETL has a thickness within these ranges, the ETL may have good electron transport characteristics without a substantial increase in driving voltage.

In addition, the EIL, which facilitates injection of electrons from the cathode, may be formed on the ETL. An EIL material may include the heterocyclic compound of Formula 1 described above. Alternatively, known EIL materials, such as LiF, NaCl, CsF, $Li_2O$, or BaO, may be used to form the EIL. The deposition or coating conditions may be similar to those used to form the HIL, although the deposition and coating conditions may vary according to the material that is used to form the EIL.

The EIL may have a thickness of about 1 Å to 100 Å. For example, the EIL may have a thickness of about 5 Å to about 90 Å. When the EIL has a thickness within the above range, the EIL may have good electron injection characteristics without a substantial increase in driving voltage.

Finally, the second electrode may be formed on the EIL using, for example, vacuum deposition, sputtering, or the like. The second electrode may be a cathode or an anode. A second electrode material may include a metal, an alloy, an electrically conductive compound, or mixtures thereof, all of which have low work functions. Nonlimiting examples of such materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

According to embodiments of the present invention, at least one layer of the organic light-emitting device may be formed of the heterocyclic compound of Formula 1 and may be formed using a deposition method or a wet method of coating a solution of the heterocyclic compound of Formula 1.

The following Examples are presented for illustrative purposes only, and do not limit the scope of the present invention.

EXAMPLES

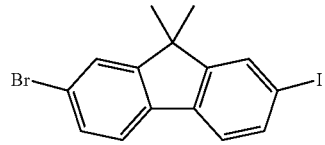

intermediate 1

Synthesis of Intermediate 1

30.27 g (110.8 mmol) of 2-bromo-9,9-dimethyl-9-fluorene, 16.9 g (66.5 mmol) of $I_2$, and 15.2 g (66.5 mmol) of $H_5IO_6$ were dissolved in acetic acid (AcOH). A dilution of $H_2SO_4$ in $H_2O$ was dropwise added into the solution and stirred at 50° C. for 5 hours, and then pure water was added to the reaction solution to obtain solid precipitates. The precipitates were collected and filtered to obtain 37.6 g (yield 85%) of intermediate 1, and this compound was identified using high-resolution mass spectra (HR-MS).

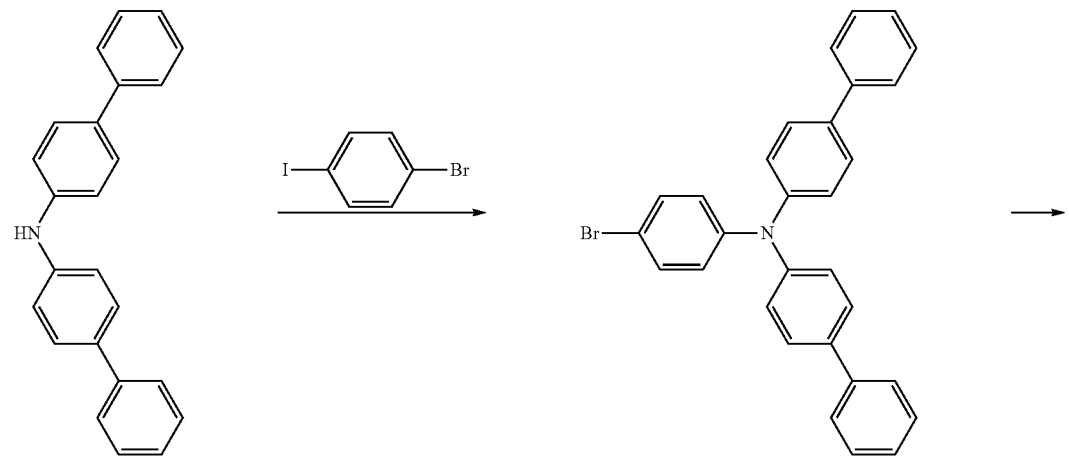

Intermediate 2

Intermediate 3

-continued
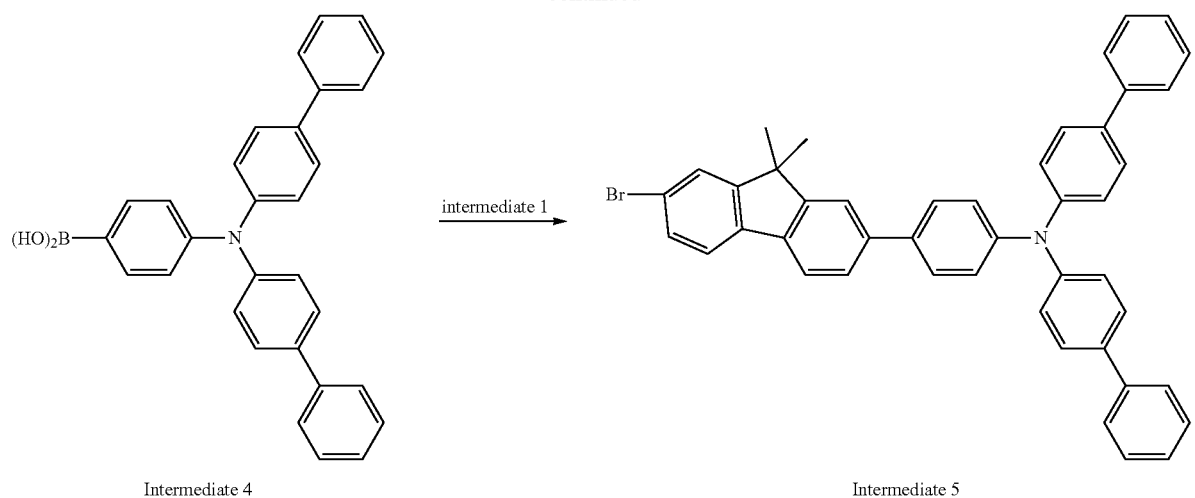
Intermediate 4 → intermediate 1 → Intermediate 5
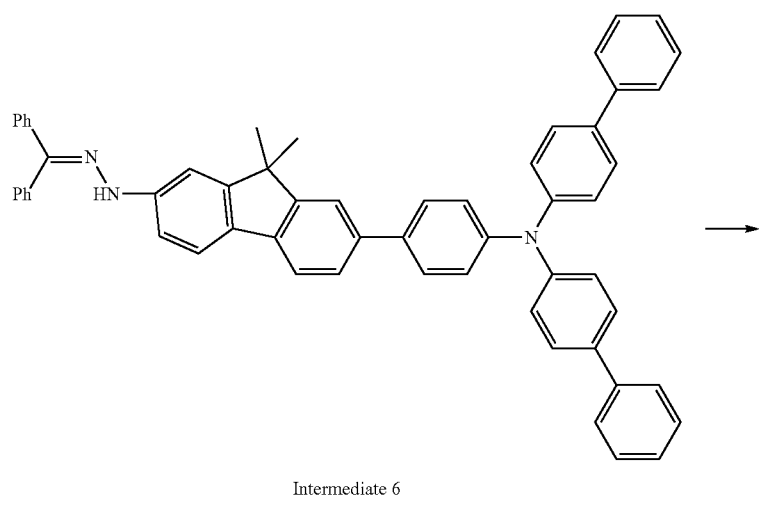
Intermediate 6
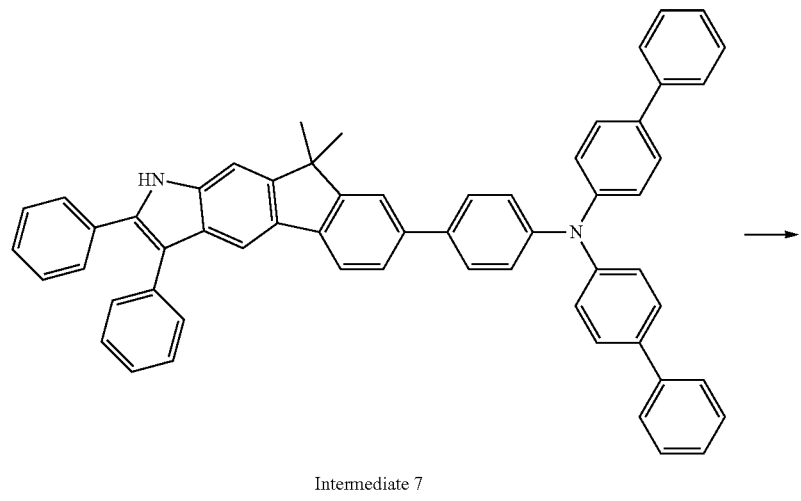
Intermediate 7

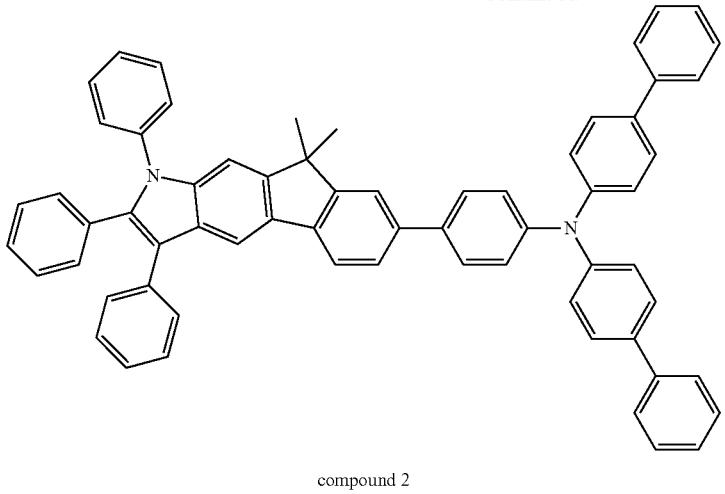

compound 2

Synthesis of Intermediate 2

7 g (30 mmol) of 4-bromobiphenyl, 7.62 g (45 mmol) of aminobiphenyl, 4.3 g (45 mmol) of t-BuONa, 0.55 g (0.6 mmol) of $Pd_2(dba)_3$, and 0.12 g (0.6 mmol) of $P(t\text{-}Bu)_3$ were dissolved in 100 mL of toluene and stirred at 90° C. for 3 hours. After the reaction was completed, the reaction product was cooled to room temperature and extracted three times with distilled water and 100 ml of diethylether. An organic layer was collected and dried using magnesium sulfate to evaporate the solvent. The residue was separated and purified using silica gel column chromatography to obtain 8.77 g (yield: 91%) of intermediate 2. This compound was identified using HR-MS.

Synthesis of Intermediate 3

8.5 g (30 mmol) of 4-bromoiodobenzene, 6.45 g (20 mmol) of Intermediate 2, 4.3 g (45 mmol) of t-BuONa, 0.55 g (0.6 mmol) of $Pd_2(dba)_3$, and 0.12 g (0.6 mmol) of $P(t\text{-}Bu)_3$ were dissolved in 100 mL of toluene and stirred at 90° C. for 3 hours. After the reaction was completed, the reaction product was cooled to room temperature and extracted three times with distilled water and 100 ml of diethylether. An organic layer was collected and dried using magnesium sulfate to evaporate the solvent. The residue was separated and purified using silica gel column chromatography to obtain 7.53 g (yield: 79%) of Intermediate 3.

Synthesis of Intermediate 4

47.64 g (100.0 mmol) of Intermediate 3 was dissolved in 200 mL of THF and cooled to −78° C., and 44 mL (2.5M in hexane, 110 mmol) of butyllithium was slowly dropwise added to the solution in a nitrogen atmosphere. The reaction temperature was maintained at −78° C. for 30 minutes, raised to −30° C. and cooled again to −78° C. Then, 16.8 mL (150 mmol) of trimethylborate was slowly dropwise added to the reaction product, and the temperature was raised to room temperature and maintained for 2 hours. 30 mL of 1 N HCl solution was slowly dropwise added to the reaction mixture and maintained for 30 minutes. 100 mL of water was further added to the reaction mixture and was extracted twice with 200 ml of ethylacetate. An organic layer was collected and dried, followed by filtration and concentration. The residue was separated by column chromatography to obtain 30.45 g (yield: 69%) of Intermediate 4.

Synthesis of Intermediate 5

7.98 g (20 mmol) of Intermediate 1, 8.82 g (20 mmol) of Intermediate 4, 1.15 g (0.9 mmol) of $Pd(PPh_3)_4$, and 5.9 g (40 mmol) of $K_2CO_3$ were dissolved in 100 ml of a mixed solution of $THF/H_2O$ (2:1), and stirred at 80° C. for 5 hours. The reaction product was cooled to room temperature, and 100 mL of water was added thereto. The reaction solution was extracted three times with 600 mL of diethylether. An organic layer was collected and dried using magnesium sulfate to evaporate the solvent. The residue was recrystallized with dichloromethane and normal hexane to obtain 10.03 g (yield: 75%) of Intermediate 5. This compound was identified using HR-MS.

Synthesis of Intermediate 6

6.86 g (10 mmol) of Intermediate 5, 2.15 g (11 mmol) of benzophenone hydrazone, 1.44 g (15 mmol) of t-BuONa, 45 mg (0.2 mmol) of $Pd(OAc)_2$, and 95 mg (0.2 mmol) of 2-dicyclohexylphosphino-2',4',6'-triisopropylbiphenyl were dissolved in 30 mL of toluene and stirred at 90° C. for 3 hours. The reaction product was cooled to room temperature. Distilled water was added thereto and extracted twice with 80 mL of diethylether and once with 80 mL of dichloromethane. An organic layer was collected and dried using magnesium sulfate, followed by filtration. A solvent was evaporated, and the residue was separated and purified using silica gel column chromatography to obtain 6.54 g (yield: 83%) of Intermediate 6. This compound was identified using HR-MS.

Synthesis of Intermediate 7

15.76 g (20 mmol) of Intermediate 6, 7.6 g (40 mmol) of p-toluenesulfonic acid dehydrate, 5.88 g (30 mmol) of benzylphenylketone were dissolved in 80 mL of ethanol and 80 mL of toluene and stirred at 110° C. for 24 hours. The reaction product was cooled to room temperature. Distilled water was added thereto and extracted twice with 100 mL of diethylether and twice with 100 mL of dichloromethane. An organic layer was collected and dried using magnesium sulfate, followed by filtration. A solvent was evaporated, and the residue was separated and purified using silica gel column chromatography to obtain 11.25 g (yield: 72%) of Intermediate 7. This compound was identified using HR-MS.

Synthesis of Compound 2

7.8 g (10 mmol) of Intermediate 7, 1.88 g (12 mmol) of bromobenzene, 2.88 g (30 mmol) of t-BuONa, 370 mg (0.4 mmol) of $Pd_2(dba)_3$, and 80 mg (0.4 mmol) of $P(t-Bu)_3$ were dissolved in 60 ml of toluene and stirred at 90° C. for 3 hours. After the reaction was completed, the reaction product was cooled to room temperature and extracted three times with distilled water and 50 ml of diethylether. An organic layer was collected and dried using magnesium sulfate to evaporate the solvent. The residue was separated and purified using silica gel column chromatography to obtain 5.9 g (yield: 69%) of Compound 2. (calc.; 856.3817. found; 856.3825) (1H-NMR, 400 MHz, CD2Cl2: δ8.22-7.67 (m, 4H), δ7.61-7.12 (m, 38H), 1.67 (s, 6H), 13C-NMR: 142.2, 140.1, 139.5, 138.2, 138.1, 137.5, 134.2, 134.1, 134.0, 132.1, 132.0, 129.9, 129.3, 128.7, 128.6, 128.4, 128.0, 126.3, 124.8, 124.5, 124.3, 123.3, 123.1, 121.5, 121.9, 121.4, 121.1, 120.5, 120.4, 120.0, 116.3, 115.8, 37.6, 31.6).

Synthesis of Compound 14

Compound 14 was synthesized with a yield of 72% in the same manner as that of Compound 2, except that Intermediate 7 and 4-bromobiphenyl were used instead of Intermediate 7 and bromobenzene. This compound was identified using HR-MS. (calc.; 932.4130. found; 932.4123), (1H-NMR, 400 MHz, CD2Cl2: δ8.25-7.69 (m, 4H), δ7.65-7.22 (m, 42H), 1.65 (s, 6H), 13C-NMR: 142.4, 140.2, 139.4, 138.5, 138.0, 137.7, 134.5, 134.2, 134.0, 132.2, 132.0, 129.9, 128.9, 128.7, 128.6, 128.4, 127.7, 126.8, 124.6, 124.5, 124.3, 123.3, 123.1, 122.5, 122.2, 121.4, 121.9, 121.4, 121.1, 120.5, 120.4, 120.0, 116.3, 115.8, 37.6, 31.6).

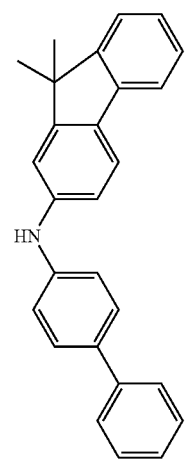

Intermediate 8

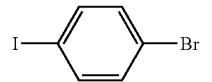

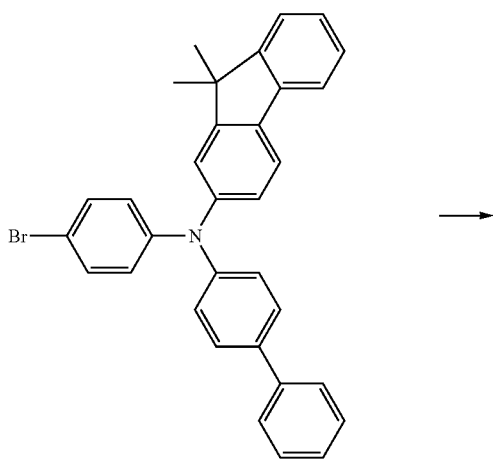

Intermediate 9

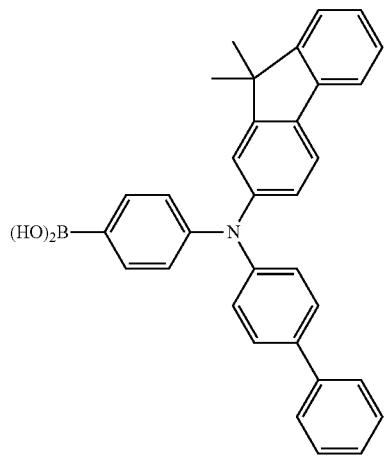

Intermediate 10

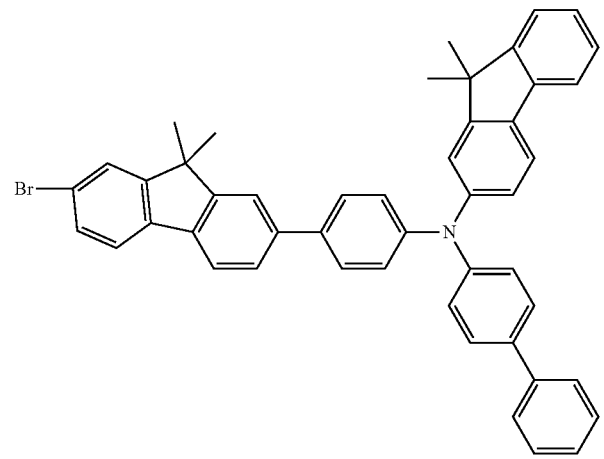

Intermediate 11

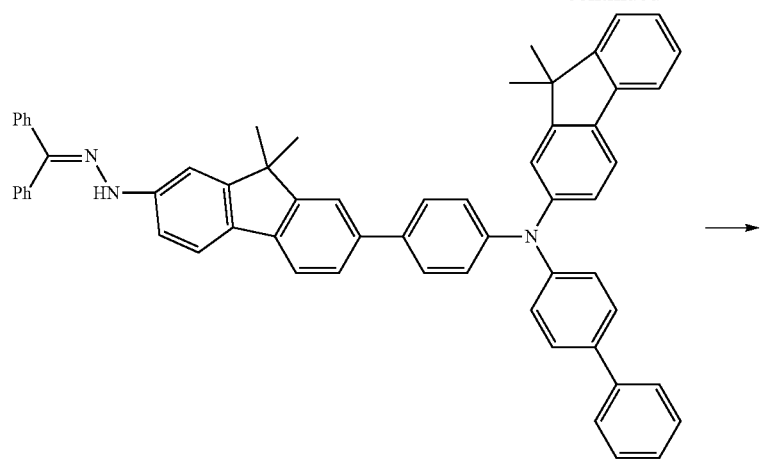
Intermediate 12
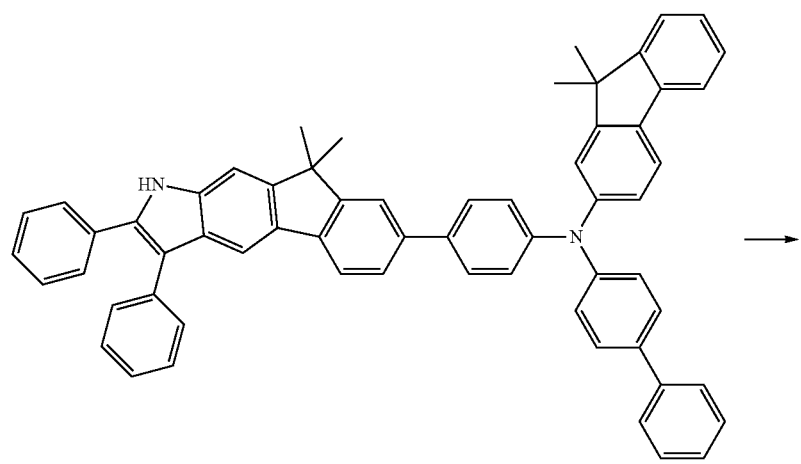
Intermediate 13
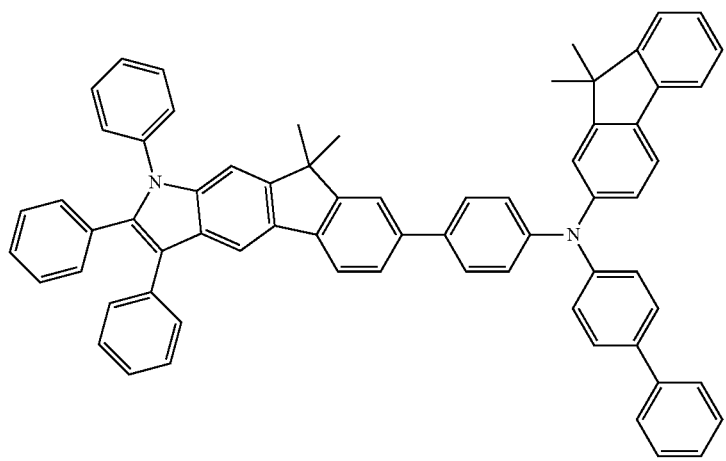
compound 23

Synthesis of Intermediate 8

Intermediate 8 was synthesized with a yield of 85% in the same manner as that of Intermediate 2, except that 2-amino-9,9-dimethylfluorene was used instead of 2-aminobiphenyl. This compound was identified using HR-MS.

Synthesis of Intermediate 9

Intermediate 9 was synthesized with a yield of 81% in the same manner as that of Intermediate 3, except that Intermediate 8 was used instead of Intermediate 2. This compound was identified using HR-MS.

Synthesis of Intermediate 10

Intermediate 10 was synthesized with a yield of 74% in the same manner as that of Intermediate 4, except that Intermediate 10 was used instead of Intermediate 3.

Synthesis of Intermediate 11

Intermediate 11 was synthesized with a yield of 64% in the same manner as that of Intermediate 5, except that Intermediate 10 was used instead of Intermediates 1 and 4.

Synthesis of Intermediate 12

Intermediate 12 was synthesized with a yield of 82% in the same manner as that of Intermediate 6, except that Intermediate 10 was used instead of Intermediate 5.

Synthesis of Intermediate 13

Intermediate 13 was synthesized with a yield of 64% in the same manner as that of Intermediate 7, except that Intermediate 12 was used instead of Intermediate 6.

Synthesis of Compound 23

Compound 23 was synthesized with a yield of 72% in the same manner as that of Compound 2, except that Intermediate 13 and 1-bromonaphthalene were used instead of Intermediate 7 and bromobenzene. This compound was identified using HR-MS. (calc.; 906.3974. found; 906.3969), (1H-NMR, 400 MHz, CD2Cl2: δ8.25-7.69 (m, 4H), δ7.65-7.22 (m, 42H), 1.65 (s, 6H), 13C-NMR: 142.4, 140.2, 139.4, 138.5, 138.0, 137.7, 134.5, 134.2, 134.0, 132.2, 132.0, 129.9, 128.9, 128.7, 128.6, 128.4, 127.7, 126.8, 124.6, 124.5, 124.3, 123.3, 123.1, 122.5, 122.2, 121.4, 121.9, 121.4, 121.1, 120.5, 120.4, 120.0, 116.3, 115.8, 37.6, 31.6).

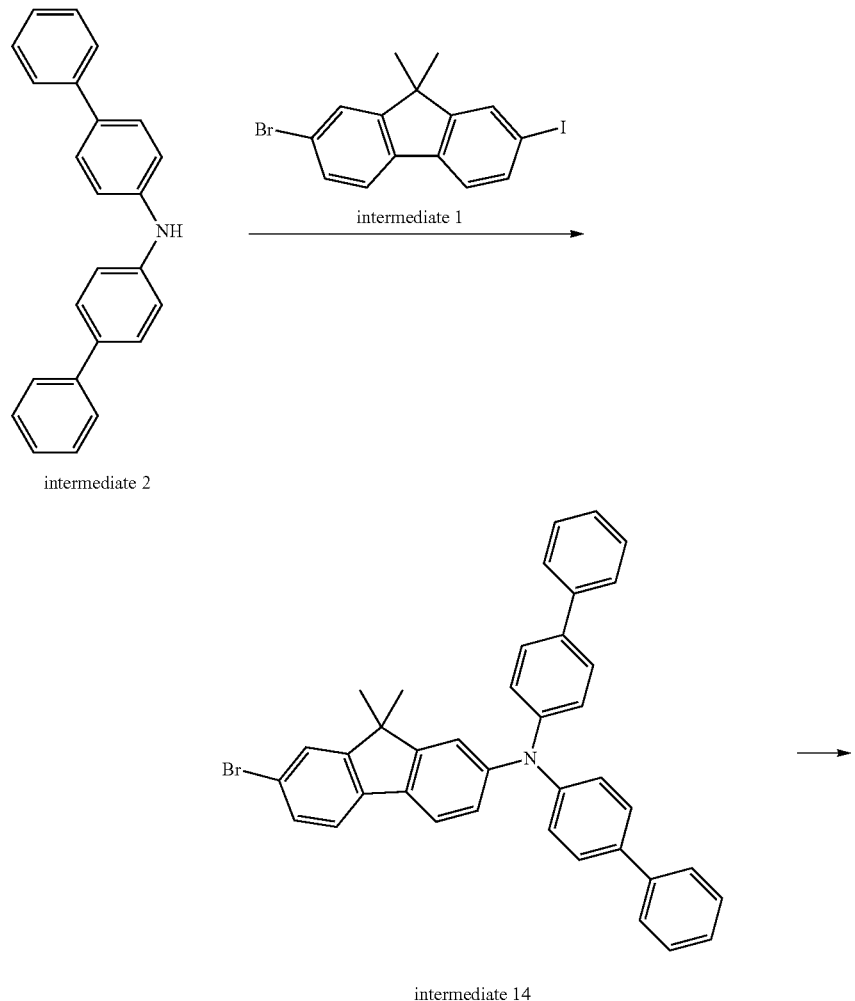

-continued
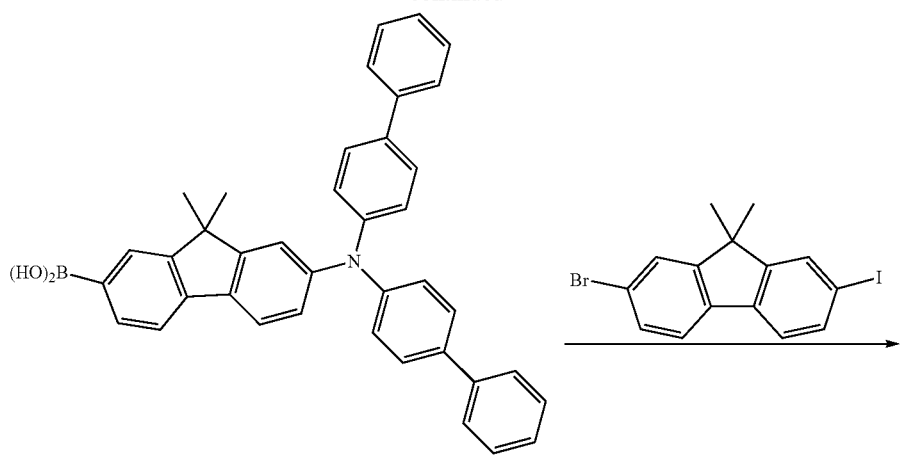
intermediate 15
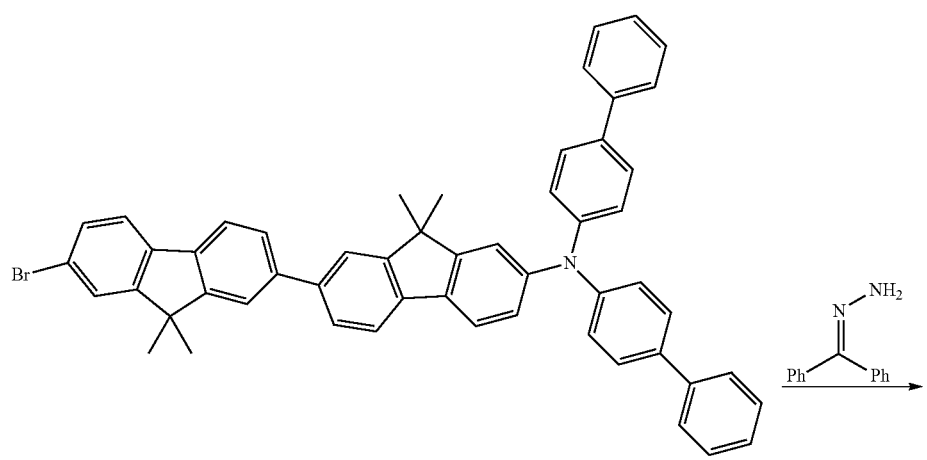
intermediate 16
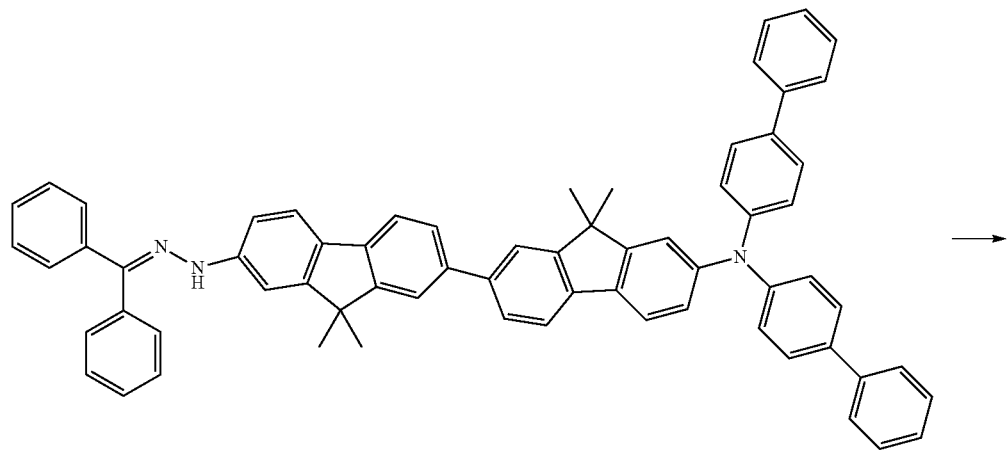
intermediate 17

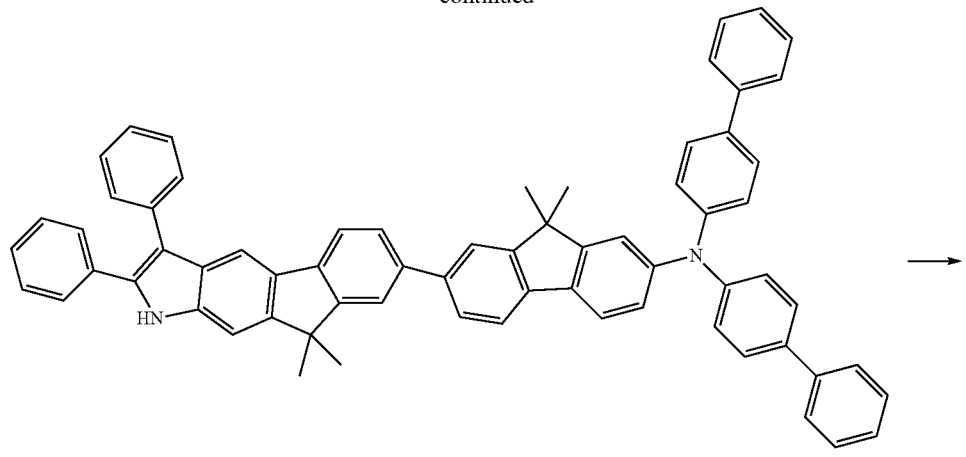

intermediate 18

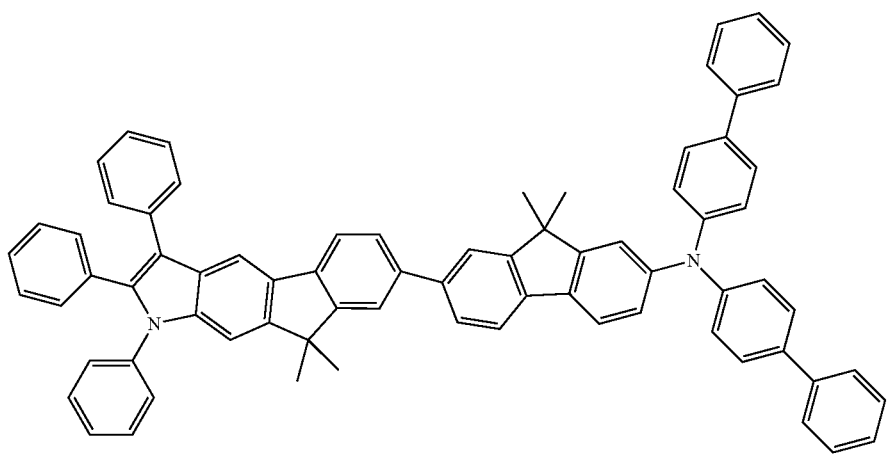

compound 32

Synthesis of Intermediate 14

Intermediate 14 was synthesized with a yield of 67% in the same manner as that of Intermediate 3, except that Intermediate 1 was used instead of Intermediate 2. This compound was identified using HR-MS.

Synthesis of Intermediate 15

Intermediate 15 was synthesized with a yield of 78% in the same manner as that of Intermediate 4, except that Intermediate 14 was used instead of Intermediate 3. This compound was identified using HR-MS.

Synthesis of Intermediate 16

Intermediate 16 was synthesized with a yield of 74% in the same manner as that of Intermediate 5, except that Intermediate 15 was used instead of Intermediates 1 and 4. This compound was identified using HR-MS.

Synthesis of Intermediate 17

Intermediate 17 was synthesized with a yield of 75% in the same manner as that of Intermediate 6, except that Intermediate 16 was used instead of Intermediate 5. This compound was identified using HR-MS.

Synthesis of Intermediate 18

Intermediate 18 was synthesized with a yield of 64% in the same manner as that of Intermediate 7, except that Intermediate 17 was used instead of Intermediate 6. This compound was identified using HR-MS.

Synthesis of Compound 32

Compound 32 was synthesized with a yield of 65% in the same manner as that of Compound 2, except that Intermediate 18, instead of Intermediate 7, was reacted with bromobenzene. This compound was identified using HR-MS. (calc.; 972.4443. found; 972.4434), (1H-NMR, 400 MHz, CD2Cl2: δ8.20-7.69 (m, 4H), δ7.55-7.22 (m, 45H), 1.65 (s, 6H), 1.61 (s, 6H), 13C-NMR: 141.4, 140.6, 140.2, 139.1, 139.3, 138.5, 138.3, 137.3, 134.6, 134.2, 134.1, 133.2, 132.0, 129.2, 128.9, 128.7, 128.6, 128.4, 127.5, 126.8, 124.7, 124.5, 124.3, 123.7, 123.1, 122.4, 122.2, 121.2, 121.9, 121.4, 121.1, 120.5, 120.4, 120.0, 116.3, 115.8, 37.6, 36.5, 32.4, 31.3).

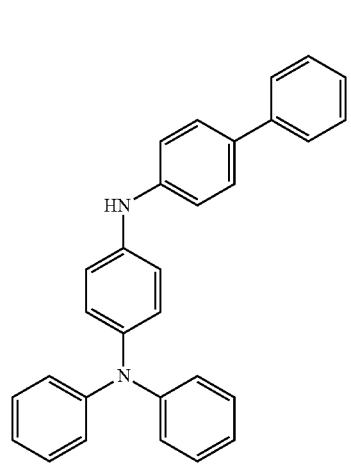
intermediate 19
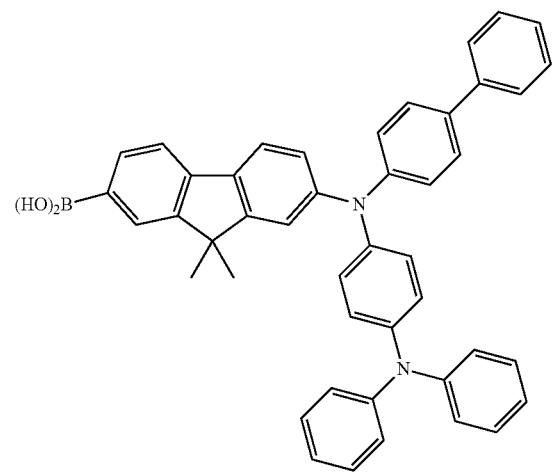
intermediate 20
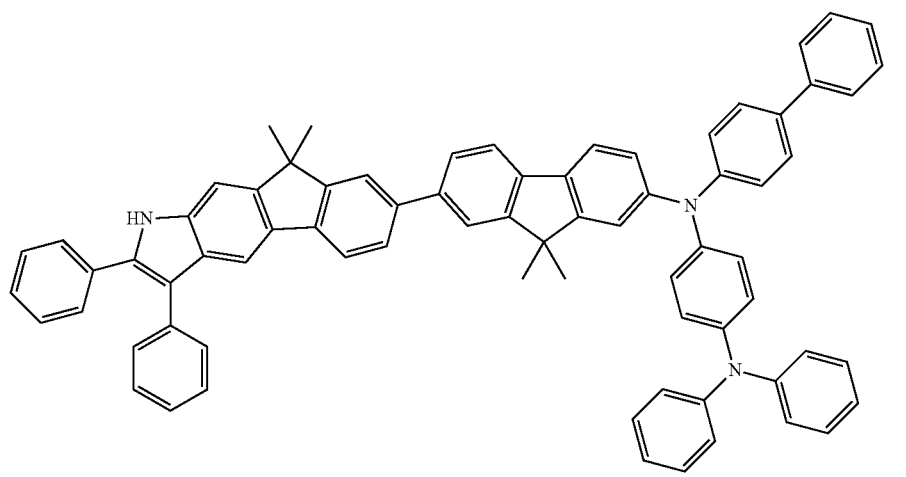
intermediate 21
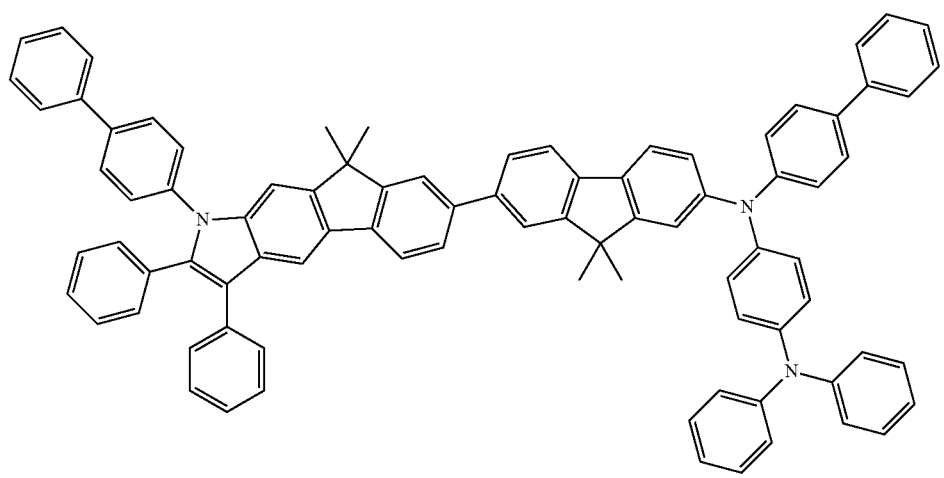
compound 42

Synthesis of Intermediate 19

Intermediate 19 was synthesized with a yield of 82% in the same manner as that of Intermediate 2, except that N,N-diphenylamino-4-bromobenzene was used instead of 4-bromobiphenyl. This compound was identified using HR-MS.

Synthesis of Intermediates 20 and 21

Intermediates 20 and 21 were synthesized through a series of reactions in the same manner as that of Intermediate 7. (Total five steps—yield: 15.3%).

Synthesis of Compound 42

Compound 42 was synthesized with a yield of 71% in the same manner as that of Compound 2, except that Intermediate 21 and 4-bromobiphenyl were used instead of Intermediate 7 and bromobenzene. This compound was identified using HR-MS. (calc.; 1048.4756. found; 1048.4766), (1H-NMR, 400 MHz, CD2Cl2: δ8.20-7.21 (m, 72H), 1.69 (s, 18H), 13C-NMR: 142.1, 141.2, 139.1, 138.6, 137.3, 136.6, 135.2, 135.1, 134.1, 133.2, 132.0, 128.7, 127.5, 126.8, 124.7, 124.5, 124.3, 123.7, 123.5, 123.1, 122.8, 122.2, 21.4, 121.1, 118.6, 118.2, 117.5, 117.2, 116.6, 31.4).

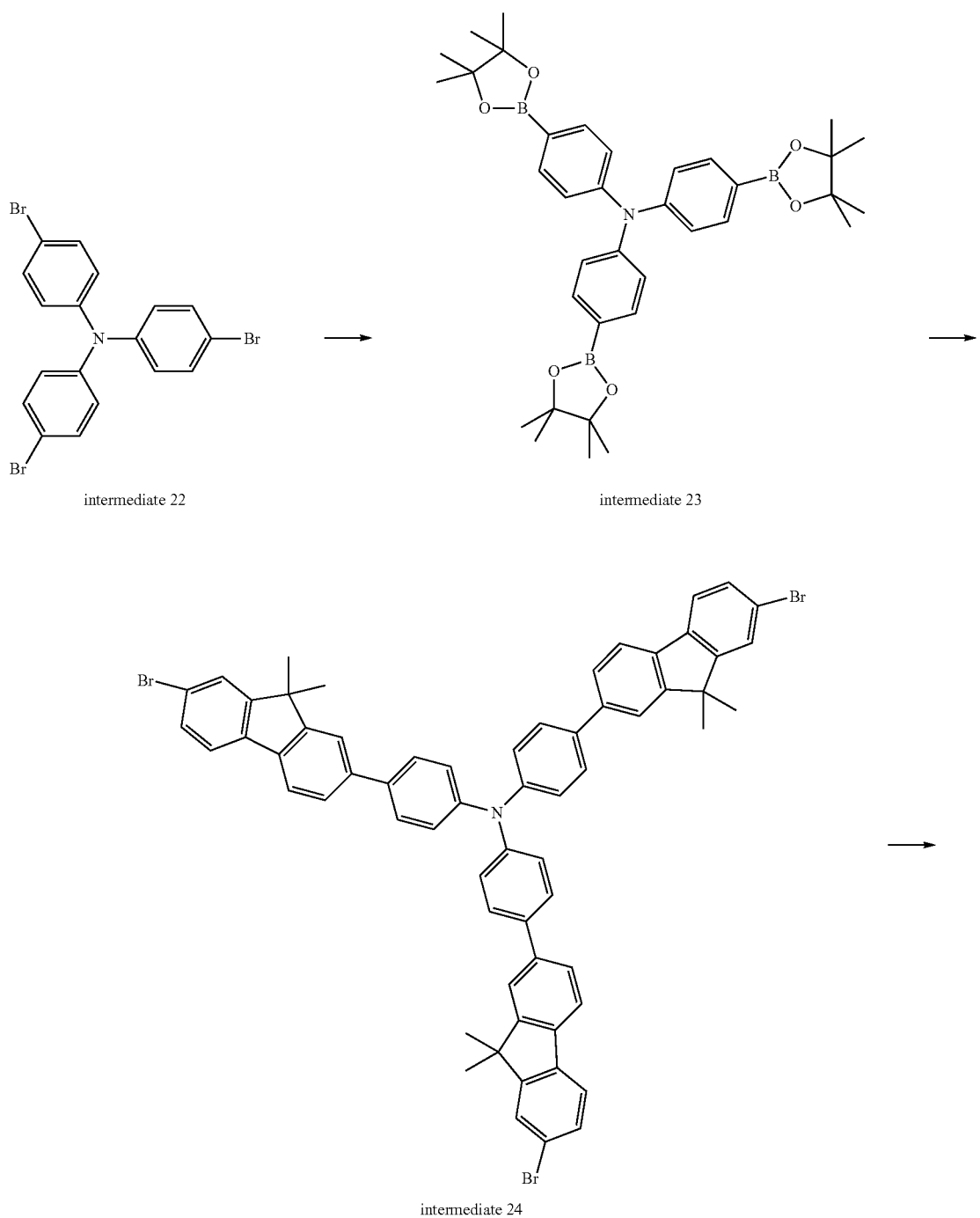

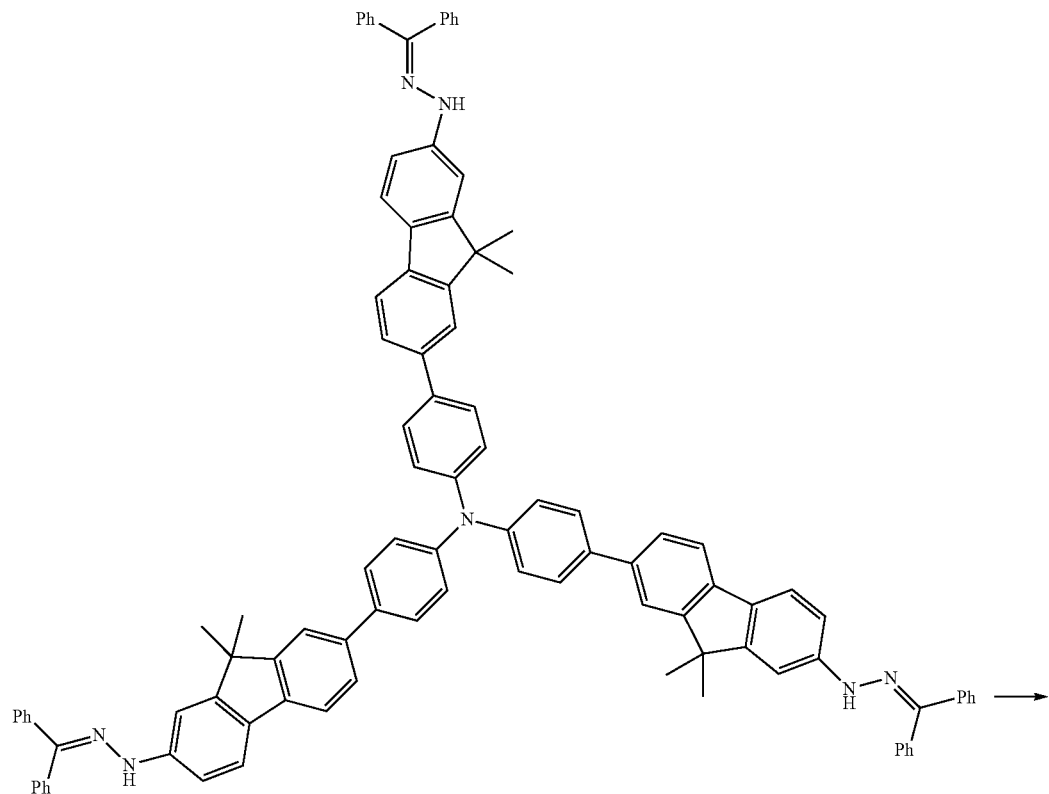
intermediate 25

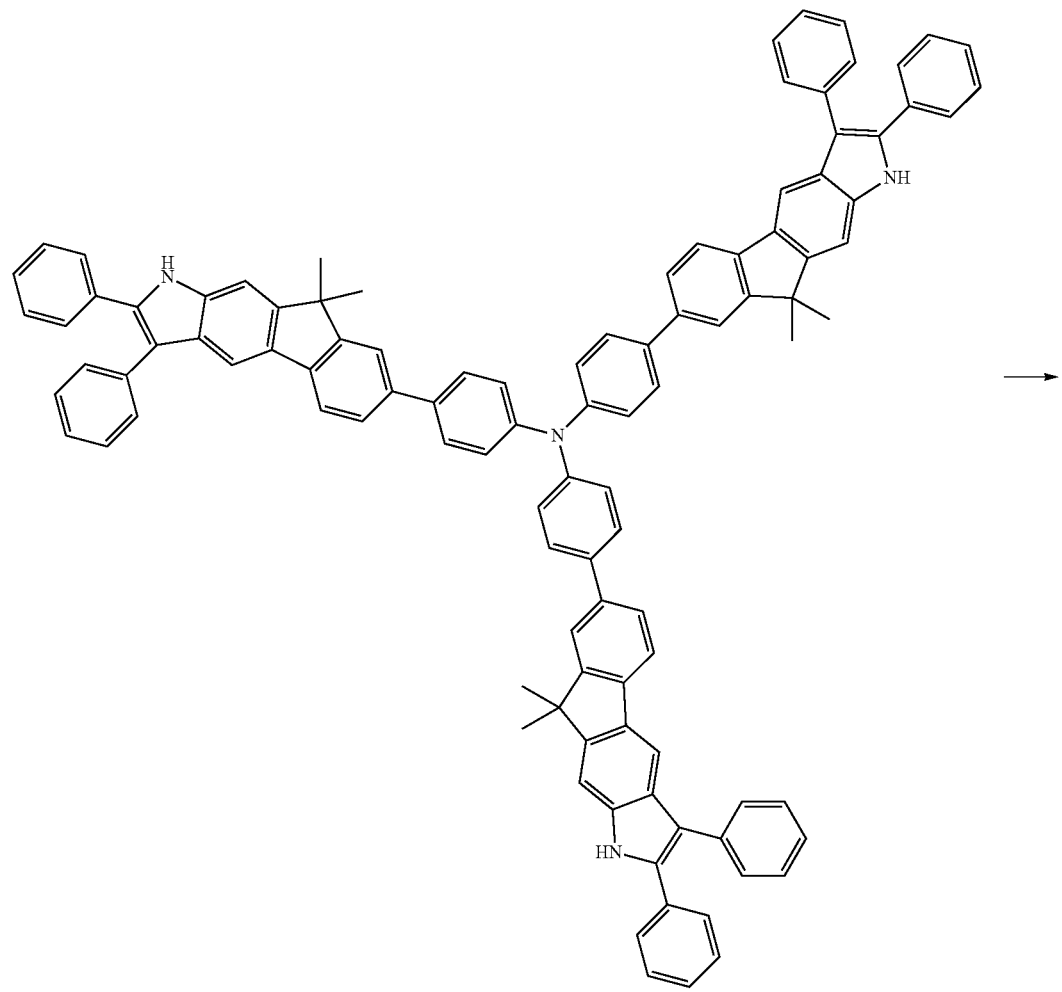
intermediate 26

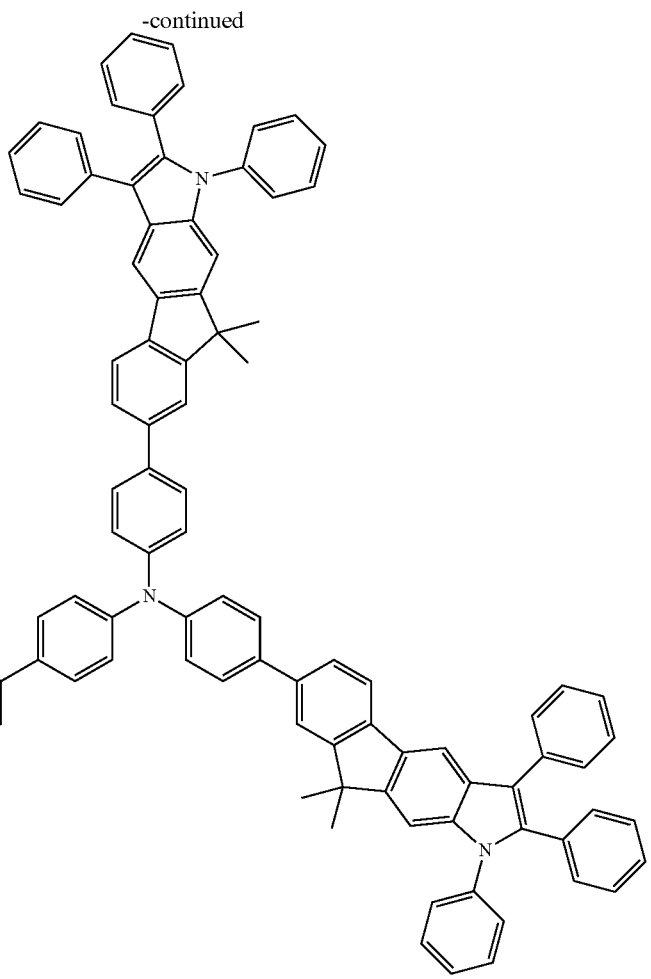

compound 76

Synthesis of Intermediate 22

24.5 g (100 mmol) of triphenylamine was dissolved in 500 mL of methylene chloride and cooled to −78° C. Then, a dilution of 31.9 g (200 mmol) of bromine in 100 mL of methylene chloride was dropwise added thereto while stirring. After the dropwise addition was completed, the mixture was further stirred at room temperature for 30 minutes. 300 mL of cold water was added thereto and extracted with methylene chloride. An organic layer was collected and dried using magnesium sulfate to evaporate the solvent. The residue was recrystallized using a mixed solution of methylene chloride and hexane to obtain 36.7 g (yield: 68%) of Intermediate 22. This compound was identified using HR-MS.

Synthesis of Intermediate 23

84 g (330 mmol) of bis(pinacolato)diboron, 48.2 g (100 mmol) of Intermediate 22, 4.3 g (45 mmol) of t-BuONa, and 1.2 g (1.5 mmol) of Pd(dppf)$_2$Cl$_2$ were dissolved in 1000 mL of toluene and stirred at 90° C. for 3 hours. After the reaction was completed, the reaction product was cooled to room temperature and extracted three times with distilled water and 500 ml of diethylether. An organic layer was collected and dried using magnesium sulfate to evaporate the solvent. The residue was separated and purified using silica gel column chromatography to obtain 44.2 g (yield: 71%) of Intermediate 23. This compound was identified using HR-MS.

Synthesis of Intermediate 24

Intermediate 24 was synthesized with a yield of 44% in the same manner as that of Intermediate 5, except that Intermediate 23, instead of Intermediate 4, and Intermediate 1 (3 equivalents) were used. This compound was identified using HR-MS.

Synthesis of Intermediate 25

Intermediate 25 was synthesized with a yield of 54% in the same manner as that of Intermediate 6, except that Intermediate 24, instead of Intermediate 5, and benzophenone hydrazone (3 equivalents) were used. This compound was identified using HR-MS.

Synthesis of Intermediate 26

Intermediate 26 was synthesized with a yield of 24% in the same manner as that of Intermediate 7, except that Intermediate 25, instead of Intermediate 6, and benzylphenylketone (5 equivalents) were used. This compound was identified using HR-MS.

Synthesis of Compound 76

Compound 76 was synthesized with a yield of 43% in the same manner as that of Compound 2, except that Intermediate 26 and 4-bromobenzene (5 equivalents) were used instead of Intermediate 7 and bromobenzene. This compound was identified using HR-MS. (1H-NMR, 400 MHz, CD2Cl2: δ8.20-7.69 (m, 4H), δ7.55-7.22 (m, 45H), 1.65 (s, 6H), 1.61 (s, 6H), 13C-NMR: 141.4, 140.6, 140.2, 139.1, 139.3, 138.5, 138.3, 137.3, 134.6, 134.2, 134.1, 133.2, 132.0, 129.2, 128.9, 128.7, 128.6, 128.4, 127.5, 126.8, 124.7, 124.5, 124.3, 123.7, 123.1, 122.4, 122.2, 121.2, 121.9, 121.4, 121.1, 120.5, 120.4, 120.0, 116.3, 115.8, 37.6, 36.5, 32.4, 31.3).

Example 1

An anode was prepared by cutting a Corning 15 Ωcm² (1200 Å) ITO glass substrate to a size of 50 mm×50 mm×0.7 mm, ultrasonically cleaning the glass substrate using isopropyl alcohol and pure water for 5 minutes each, and then irradiating UV light for 30 minutes and exposing to ozone to clean. Then, the anode was mounted in a vacuum deposition apparatus.

2-TNATA was vacuum-deposited on the glass substrate to form a HIL having a thickness of 600 Å, and then Compound 2 as a hole transport compound was vacuum deposited on the HIL to form a HTL having a thickness of 300 Å.

Then, a green fluorescent host (Alq$_3$) and a green fluorescent dopant (C545T) were simultaneously deposited in a weight ratio of 98:2 on the HTL, to form an EML having a thickness of 300 Å.

Then, Alq$_3$ was deposited on the EML to form an ETL having a thickness of 300 Å, and then LiF (which is halogenated alkali metal) was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

The organic light-emitting device had a driving voltage of 6.23V at a current density of 50 mA/cm², a high emission brightness of 8330 cd/m², color coordinates of (0.310, 0.643), and an emission efficiency of 16.66 cd/A.

Example 2

An organic light-emitting device was manufactured as in Example 1, except that Compound 14 was used instead of Compound 2 to form the HTL.

The organic light-emitting device had a driving voltage of 6.14 V at a current density of 50 mA/cm², a high emission brightness of 7,956 cd/m², and an emission efficiency of 18.52 cd/A.

Example 3

An organic light-emitting device was manufactured as in Example 1, except that Compound 23 was used instead of Compound 2 to form the HTL.

The organic light-emitting device had a driving voltage of 6.54 V at a current density of 50 mA/cm², a high emission brightness of 8,347 cd/m², and an emission efficiency of 18.04 cd/A.

Example 4

An organic light-emitting device was manufactured as in Example 1, except that Compound 32 was used instead of Compound 2 to form the HTL.

The organic light-emitting device had a driving voltage of 6.55 V at a current density of 50 mA/cm², a high emission brightness of 8,271 cd/m², and an emission efficiency of 18.14 cd/A.

Example 5

An organic light-emitting device was manufactured as in Example 1, except that Compound 42 was used instead of Alq$_3$ to form the ETL.

The organic light-emitting device had a driving voltage of 6.88 V at a current density of 50 mA/cm², a high emission brightness of 8,076 cd/m², and an emission efficiency of 16.91 cd/A.

Example 6

An organic light-emitting device was manufactured as in Example 1, except that Compound 76 was used instead of C545T as a green fluorescent dopant to form the EML.

The organic light-emitting device had a driving voltage of 7.32 V at a current density of 50 mA/cm², a high emission brightness of 7,236 cd/m², color coordinates of (0.321, 0.635), and an emission efficiency of 16.14 cd/A.

Comparative Example 1

An organic light-emitting device was manufactured as in Example 1, except that 4,4'-bis[N-(1-naphthyl)-N-phenylamino]biphenyl (NPB) was used instead of Compound 2 to form the HTL.

The organic light-emitting device had a driving voltage of 6.84V at a current density of 50 mA/cm², a high emission brightness of 6,730 cd/m², color coordinates of (0.320, 0.637), and an emission efficiency of 13.46 cd/A.

The organic light-emitting devices manufactured using the heterocyclic compounds of Formula 1 according to the present invention had a driving voltage that was lower by 1V or greater than devices manufactured using NPB, and thus had higher efficiency and good I-V-L characteristics. In particular, lifetime characteristics were markedly improved by 100% or greater in the organic light-emitting devices according to Examples 1 through 6 compared with the organic light-emitting device according to Comparative Example 1. The results are shown in Table 1 below.

TABLE 1

|  | Emitting material or electron transporting material | Driving voltage (V) | Current density (mA/cm²) | Luminance (cd/m²) | Efficiency (cd/A) | Color coordinates | Half-life span (hr @ 100 mA/cm²) |
| --- | --- | --- | --- | --- | --- | --- | --- |
| Example 1 | Compound 2 | 6.23 | 50 | 8,330 | 16.66 | (0.310, 0.643) | 473 hr |
| Example 2 | Compound 14 | 6.14 | 50 | 7,956 | 18.52 | (0.325, 0.653) | 512 hr |
| Example 3 | Compound 23 | 6.54 | 50 | 8,347 | 18.04 | (0.314, 1.634) | 518 hr |

TABLE 1-continued

| | Emitting material or electron transporting material | Driving voltage (V) | Current density (mA/cm$^2$) | Luminance (cd/m$^2$) | Efficiency (cd/A) | Color coordinates | Half-life span (hr @ 100 mA/cm$^2$) |
|---|---|---|---|---|---|---|---|
| Example 4 | Compound 32 | 6.55 | 50 | 8,271 | 18.14 | (0.320, 0.645) | 463 hr |
| Example 5 | Compound 42 | 6.88 | 50 | 8,076 | 16.91 | (0.314, 0.632) | 486 hr |
| Example 6 | Compound 76 | 7.32 | 50 | 7,236 | 16.14 | (0.321, 0.635) | 450 hr |
| Comparative Example 1 | NPB | 6.84 | 50 | 6,730 | 13.46 | (0.320, 0.637) | 237 hr |

The heterocyclic compounds according to embodiments of the present invention have good electrical characteristics and charge transporting capabilities, and thus may be used as at least one of a hole injecting material, a hole transporting material, and an emitting material for all-color fluorescent and phosphorescent devices, such as red, green, blue, and white fluorescent and phosphorescent devices. Thus, an organic light-emitting device with high-efficiency, low driving voltage, high luminance and long lifespan may be manufactured using the heterocylic compounds.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1:

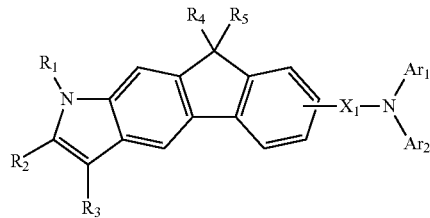

Formula 1 wherein:
each of $Ar_1$ and $Ar_2$ is independently selected from the group consisting of substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups;
$X_1$ is selected from the group consisting of single bonds, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups;
each of $R_1$, $R_2$, and $R_3$ is independently selected from hydrogen, heavy hydrogen, substituted and unsubstituted $C_1$-$C_{50}$ alkyl groups, substituted and unsubstituted $C_1$-$C_{50}$ alkoxy groups, substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups;
each of $R_4$ and $R_5$ is independently selected from the group consisting of hydrogen, heavy hydrogen, substituted and unsubstituted $C_1$-$C_{30}$ alkyl groups, substituted and unsubstituted $C_1$-$C_{30}$ alkoxy groups, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups.

2. The heterocyclic compound of claim 1, wherein the compound represented by Formula 1 is selected from the group consisting of compounds represented by Formulae 2 through 6:

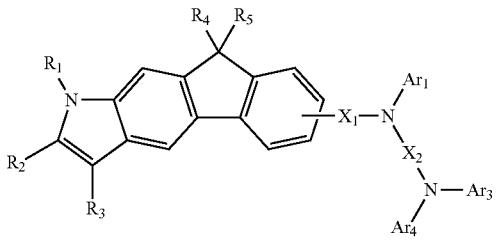

Formula 2

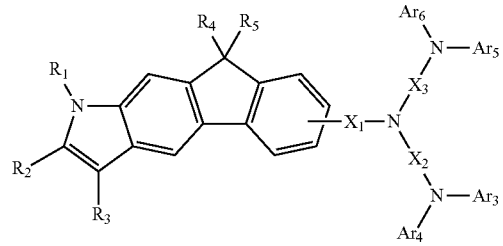

Formula 3

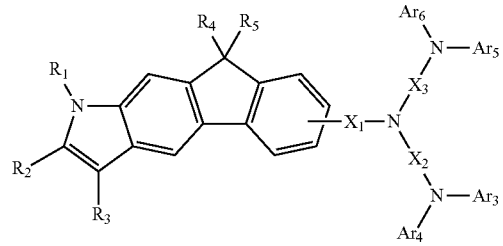

Formula 4

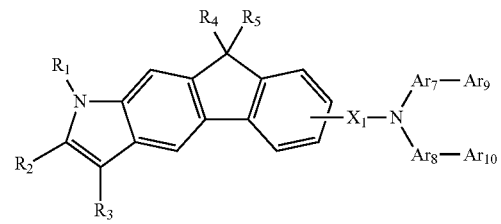

Formula 5

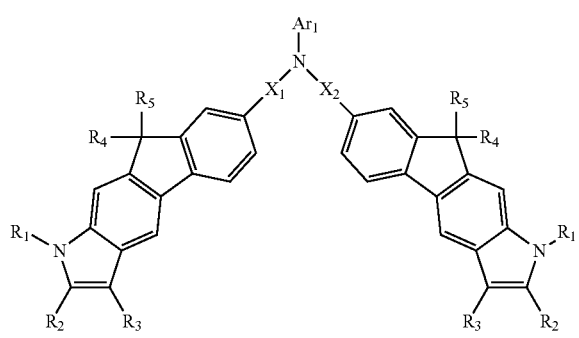

-continued

Formula 6

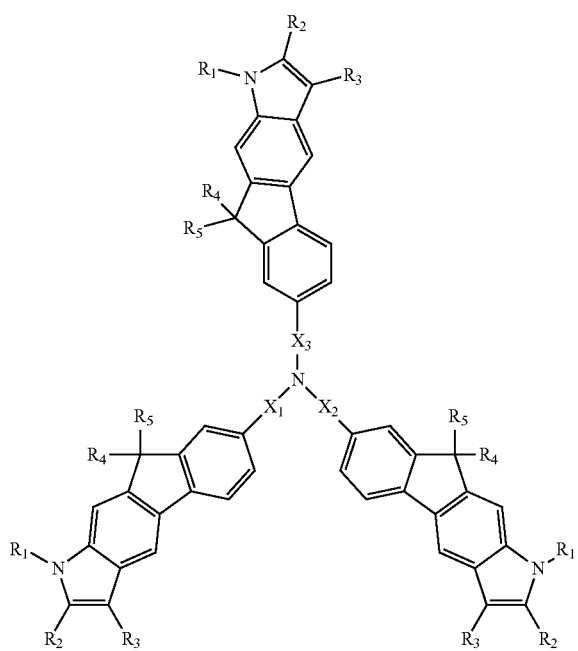

wherein:
each of $Ar_1$ and $Ar_3$ through $Ar_{10}$ is independently selected from the group consisting of substituted and unsubstituted $C_6$-$C_{60}$ aryl groups, substituted unsubstituted $C_4$-$C_{60}$ heteroaryl groups, and substituted and unsubstituted $C_6$-$C_{60}$ condensed polycyclic groups;
each of $X_1$ through $X_3$ is independently selected from the group consisting of single bonds, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups;
each of $R_1$, $R_2$, and $R_3$ is independently selected from the group consisting of hydrogen, heavy hydrogen, substituted and unsubstituted $C_1$-$C_{50}$ alkyl groups, substituted and unsubstituted $C_1$-$C_{50}$ alkoxy groups, substituted and unsubstituted $C_6$-$C_{60}$ aryl groups, substituted and unsubstituted $C_4$-$C_{60}$ heteroaryl groups, and substituted and unsubstituted $C_6$-$C_{60}$ condensed polycyclic groups;
each of $R_4$ and $R_5$ is independently selected from the group consisting of hydrogen, heavy hydrogen, substituted and unsubstituted $C_1$-$C_{30}$ alkyl groups, substituted and unsubstituted $C_1$-$C_{30}$ alkoxy groups, substituted and unsubstituted $C_6$-$C_{30}$ aryl groups, substituted and unsubstituted $C_4$-$C_{30}$ heteroaryl groups, and substituted and unsubstituted $C_6$-$C_{30}$ condensed polycyclic groups.

3. The heterocyclic compound of claim 1, wherein $Ar_1$ and $Ar_2$ are identical to each other, or $R_2$ and $R_3$ are identical to each other, or $R_4$ and $R_5$ are identical to each other.

4. The heterocyclic compound of claim 2, wherein $Ar_1$, $Ar_3$, $Ar_4$, $Ar_5$, $Ar_6$, $Ar_7$, $Ar_8$, $Ar_9$ and $Ar_{10}$ are identical to each other, or $X_1$, $X_2$, and $X_3$ are identical to each other, or $R_2$ and $R_3$ are identical to each other, or $R_4$ and $R_5$ are identical to each other.

5. The heterocyclic compound of claim 1, wherein each of $R_1$ through $R_3$ or $X_1$ is independently selected from the group consisting of phenyl groups, naphthyl groups, biphenyl groups, fluorene groups, and phenanthrene groups.

6. The heterocyclic compound of claim 2, wherein each of $R_1$ through $R_3$ or each of $X_1$ through $X_3$ is independently selected from the group consisting of phenyl groups, naphthyl groups, biphenyl groups, fluorene groups, and phenanthrene groups.

7. The heterocyclic compound of claim 1, wherein each of $R_4$ and $R_5$ is a methyl group.

8. The heterocyclic compound of claim 2, wherein each of $R_4$ and $R_5$ is a methyl group.

9. The heterocyclic compound of claim 2, wherein each of $Ar_3$ through $Ar_{10}$ is independently selected from the group consisting of:
unsubstituted monocyclic to tricyclic aryl groups selected from the group consisting of phenyl groups, naphthyl groups, biphenyl groups, terphenyl groups, anthracenyl groups, fluorenyl groups and carbazolyl groups;
unsubstituted $C_4$-$C_{30}$ heteroaryl groups;
substituted monocyclic to tricyclic aryl groups selected from the group consisting of phenyl groups, naphthyl groups, biphenyl groups, terphenyl groups, anthracenyl groups, fluorenyl groups, and carbazolyl groups having at least one substituent selected from the group consisting of $C_1$-$C_5$ alkyl groups, $C_1$-$C_5$ alkoxy groups, cyano groups, amine groups, phenoxy groups, phenyl groups, naphthyl groups, and halogen groups; and
substituted $C_4$-$C_{30}$ heteroaryl groups having at least one substituent selected from the group consisting of $C_1$-$C_5$ alkyl groups, $C_1$-$C_4$ alkoxy groups, cyano groups, amine groups, phenoxy groups, phenyl groups, naphthyl groups, and halogen groups.

10. The heterocyclic compound of claim 1, wherein the compound represented by Formula 1 is selected from the group consisting of Compounds 2, 14, 23, 32, 42 and 76:

2

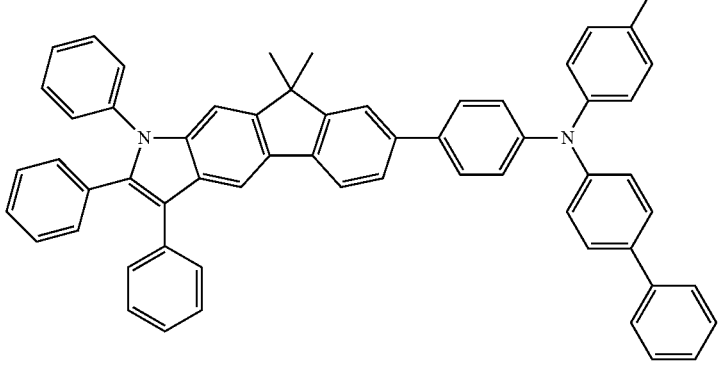

14
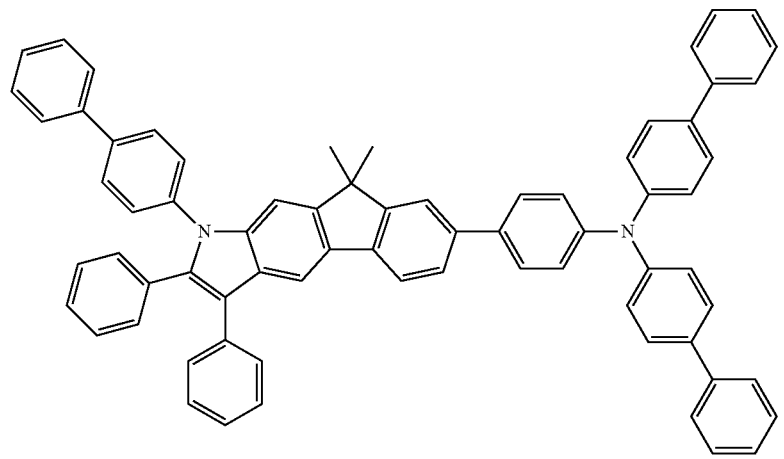
23
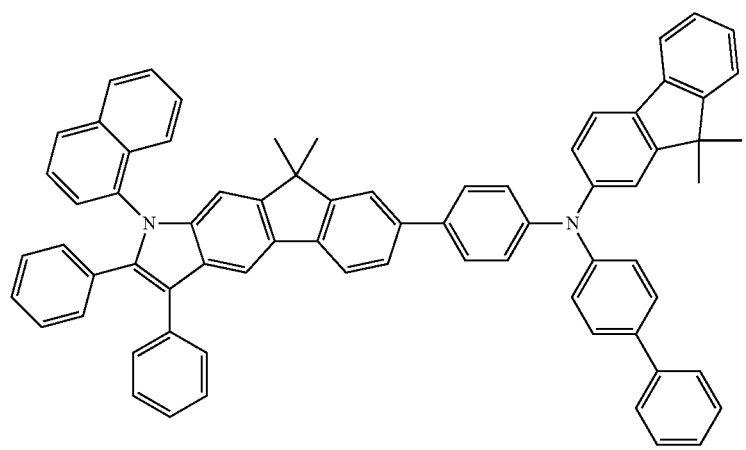
32
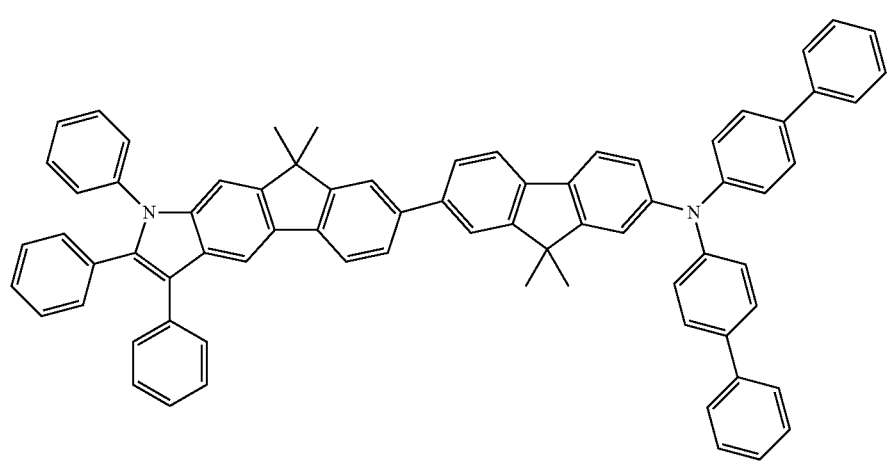

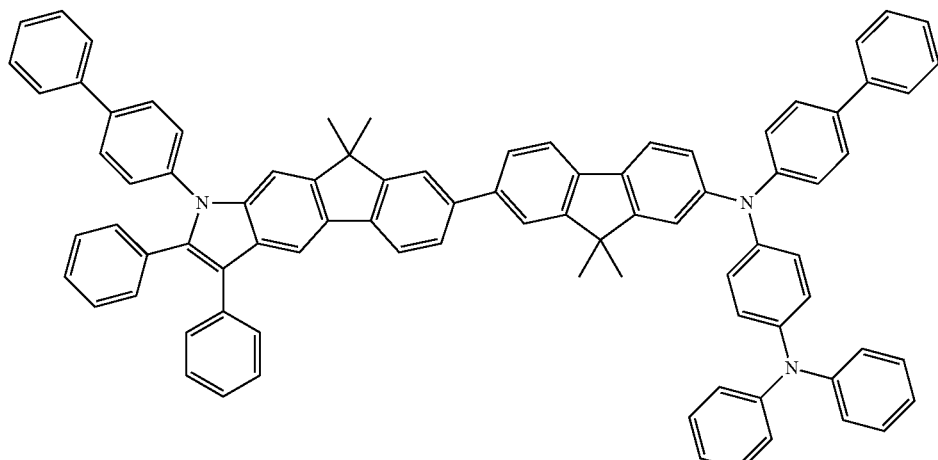

42

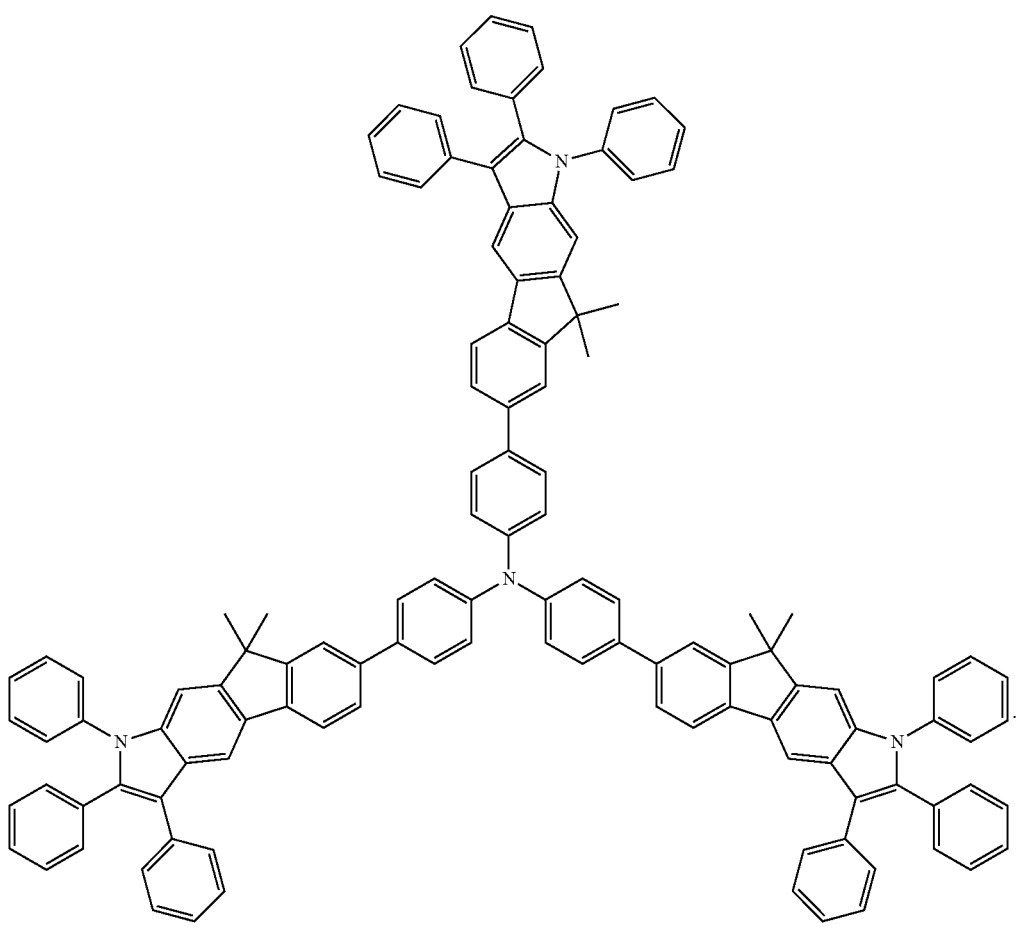

76

11. An organic light-emitting device comprising:
   a first electrode;
   a second electrode; and
   an organic layer between the first electrode and the second electrode, wherein the organic layer comprises the heterocyclic compound of claim 1.

12. The organic light-emitting device of claim 11, wherein the organic layer comprises a hole injection layer or a hole transport layer.

13. The organic light-emitting device of claim 11, wherein the organic layer comprises a single film configured for hole injection and hole transport.

14. The organic light-emitting device of claim 11, wherein the organic layer comprises an emission layer.

15. The organic light-emitting device of claim 11, wherein the organic layer comprises an emission layer, and the heterocylic compound is a host for a fluorescent or phosphorescent device.

16. The organic light-emitting device of claim 11, wherein the organic layer comprises an emission layer, and the heterocylic compound is a fluorescent dopant.

17. The organic light-emitting device of claim 11, wherein the organic layer comprises a hole injection layer or a hole transport layer, and an emission layer comprising an anthracene compound or an arylamine compound or a styryl compound.

18. The organic light-emitting material of claim 11, wherein the organic layer comprises an emission layer, and a hole injection layer or a hole transport layer, wherein the emission layer comprises a red emission layer, a green emission layer, a blue emission layer or a white emission layer that comprises a phosphorescent compound.

19. The organic light-emitting device of claim 11, wherein the organic layer comprises at least one of a hole injection layer, a hole transport layer, an electron blocking layer, an emission layer, a hole blocking layer, an electron transport layer, or an electron injection layer.

20. The organic light-emitting device of claim 19, wherein the device comprises a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

21. A flat panel display device comprising the organic light-emitting device of claim 11, wherein the first electrode of the organic light-emitting device is electrically connected to a source electrode or a drain electrode of a thin-film transistor.

22. An organic light-emitting device comprising:
a first electrode;
a second electrode; and
an organic layer between the first electrode and the second electrode,
wherein the organic layer comprises at least one layer comprising the heterocyclic compound of claim 1, the at least one layer being formed using a wet process.

* * * * *